United States Patent
Almansa-Rosales et al.

(10) Patent No.: US 11,401,270 B2
(45) Date of Patent: Aug. 2, 2022

(54) ALCOXYAMINO DERIVATIVES FOR TREATING PAIN AND PAIN RELATED CONDITIONS

(71) Applicant: ESTEVE PHARMACEUTICALS, S.A., Barcelona (ES)

(72) Inventors: Carmen Almansa-Rosales, Barcelona (ES); Félix Cuevas-Cordobés, Valdemoro (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 16/755,992

(22) PCT Filed: Oct. 26, 2018

(86) PCT No.: PCT/EP2018/079367
§ 371 (c)(1),
(2) Date: Apr. 14, 2020

(87) PCT Pub. No.: WO2019/081691
PCT Pub. Date: May 2, 2019

(65) Prior Publication Data
US 2020/0299297 A1    Sep. 24, 2020

(30) Foreign Application Priority Data

Oct. 27, 2017 (EP) .................................. 17382721

(51) Int. Cl.
| | |
|---|---|
| *C07D 471/04* | (2006.01) |
| *C07D 409/12* | (2006.01) |
| *C07D 487/02* | (2006.01) |
| *C07D 487/04* | (2006.01) |
| *C07D 243/14* | (2006.01) |
| *C07D 243/08* | (2006.01) |
| *C07D 223/10* | (2006.01) |
| *A61P 29/00* | (2006.01) |

(52) U.S. Cl.
CPC ......... *C07D 487/04* (2013.01); *C07D 223/10* (2013.01); *C07D 243/08* (2013.01); *C07D 243/14* (2013.01); *C07D 409/12* (2013.01); *C07D 471/04* (2013.01)

(58) Field of Classification Search
CPC .. C07D 471/04; C07D 409/12; C07D 487/02; C07D 487/04; C07D 243/14; C07D 243/08; C07D 223/10; A61P 29/00
See application file for complete search history.

(56) References Cited

U.S. PATENT DOCUMENTS 4,829,061 A    5/1989    Wolf

FOREIGN PATENT DOCUMENTS

| | | |
|---|---|---|
| EP | 2163554 | 3/2010 |
| WO | WO2004069256 | 8/2004 |
| WO | WO2017191304 | 11/2017 |

OTHER PUBLICATIONS

Isomer, 2021, https://en.wikipedia.org/wiki/Isomer.*
VoltageGatedCalciumChannel, 2021, https://en.wikipedia.org/wiki/Voltage-gated_calcium_channel.*
Cuervas-Cordobes-et al., 2017, caplus an 1780574.*
Chabot-Doré, Anne-Julie, et al., "Dual allosteric modulation of opioid antinociceptive potency by α2A-adrenoceptors", Neuropharmacology 99, 2015, pp. 285-300.
Davies, Anthony, et al., "Functional biology of the α2δ subunits of voltage-gated calcium channels", Trends in Pharmacological Sciences, vol. 28, No. 5, 2007, pp. 220-228.
Dolphin, Annette, C., "Calcium channel auxiliary α2δ and β subunits: trafficking and one step beyond", Nature Reviews Neuroscience AOP, Jul. 18, 2012, pp. 542-555.
Dolphin, Annette, C., "The α2δ subunits of voltage-gated calcium channels", Biochimica et Biophysica Acta, 1828, 2013, pp. 1541-1549.
Fairbanks, Carolyn, A., "Pharmacological profiles of Alpha 2 adrenergic receptor agonists identified using genetically altered Mice and isobolographic analysis", Pharmacol. Ther., 123(2), Aug. 2009, pp. 224-238.
Goldberg, Daniel. S., et a!., "Pain as a global public health priority", BMC Public Health, 11:770, 2011, pp. 1-5.
Hayashida, Ken-ichiro, et al., "Multiplicative interactions to enhance gabapentin to treat neuropathic pain", European Journal of Pharmacology, 598, 2008, pp. 21-26.
Hopkins, Andrew, L., "Network pharmacology: the next paradigm in drug discovery", Nature Chemical Biology, vol. 4, No. 11. Nov. 2008, pp. 682-690.
International Search Report for PCT/EP2018/079367 dated Jan. 9, 2019.
Irie, O., et al., "Discovery of orally bioavailabie cathepsin S inhibitors for the reversal of neuropathic pain", J Med Chem, 51(18), Sep. 25, 2008, pp. 5502-5505. https://www.ncbi.nlm.nih.gov/pubmed/18754655.

(Continued)

*Primary Examiner* — Sun Jae Yoo
(74) *Attorney, Agent, or Firm* — Hueschen and Sage

(57) ABSTRACT

The present invention relates to new compounds of formula (I) that show great affinity and activity towards the subunit α2δ of voltage-gated calcium channels (VGCC), or dual activity towards the subunit α2δ of voltage-gated calcium channels (VGCC) and the noradrenaline transporter (NET). The invention is also related to the process for the preparation of said compounds as well as to compositions comprising them, and to their use as medicaments.

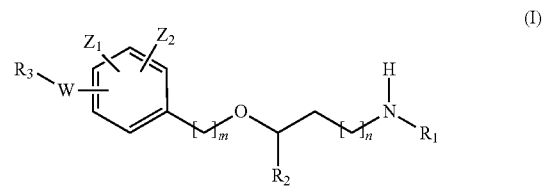

25 Claims, No Drawings

(56) References Cited

OTHER PUBLICATIONS

Lehàr, Joseph, et al., "Synergistic drug combinations improve therapeutic selectivity", Nat Biotechnol., 27(7), Jul. 2009, pp. 659-666.

Mason, Stepphen, T., "Designing a non-neuroleptic antischizophrenic drug: the noradrenergic strategy", Treands in Pharmacological Sciences, vol. 4, 1983, pp. 353-355. https://www.sciencedirect.com/science/article/abs/pii/0165614763904376.

Ossipov, Michael, H., et al., "Central modulation of pain", J Ciin Invest., 120(11), 2010, pp. 3779-3787.

Perret, Danielle, et al., "Targeting voltage-gated caicium channels for neuropathic pain management", Neurotherapeutics: The Journal of the American Society for Experimental NeuroTherapeutics, vol. 6, Oct. 2009, pp. 679-692.

Schröder, W., et al., "Synergistic interaction between the two mechanisms of action of tapentadol in analgesia", The Journal of Pharmacology and Experimental Therapeutics, vol. 337, No. 1, 2011, pp. 312-320.

Tanabe, Mitsuo, et al., "Pain relief by gabapentin and pregabalin via supraspinal mechanisms after peripheral nerve injury", Journal of Neuroscience Research, 86, 2008, pp. 3258-3264.

Turk, Dennis, C., et al., "Treatment of chronic non-cancer pain", Lancet, vol. 377, Jun. 25, 2011, pp. 2226-2235.

Wang, Ruizhong, et al, "Descending facilitation maintains long-term spontaneous neuropathic pain", J Pain., 14(8), Aug. 2013, pp. 845-853.

Zamponi, Gerald, W., et al., "The physiology, pathology, and pharmacology of voltage-gated calcium channels and their future therapeutic potential", Pharmacol Rev, 67, Oct. 2015, pp. 821-870.

\* cited by examiner

ALCOXYAMINO DERIVATIVES FOR TREATING PAIN AND PAIN RELATED CONDITIONS

FIELD OF THE INVENTION

The present invention relates to new compounds that show great affinity and activity towards the subunit α2δ of voltage-gated calcium channels (VGCC), especially the α2δ-1 subunit of voltage-gated calcium channels or dual activity towards the subunit α2δ of voltage-gated calcium channels (VGCC), especially the α2δ-1 subunit of voltage-gated calcium channels, and the noradrenaline transporter (NET). The invention is also related to the process for the preparation of said compounds as well as to compositions comprising them, and to their use as medicaments.

BACKGROUND OF THE INVENTION

The adequate management of pain represents an important challenge, since currently available treatments provide in many cases only modest improvements, leaving many patients unrelieved (Turk, D. C., Wilson, H. D., Cahana, A.; 2011; *Lancet;* 377; 2226-2235). Pain affects a big portion of the population with an estimated prevalence of 20% and its incidence, particularly in the case of chronic pain, is increasing due to the population ageing. Additionally, pain is clearly correlated to comorbidities, such as depression, anxiety and insomnia, which leads to important productivity losses and socio-economical burden (Goldberg, D. S., McGee, S. J.; 2011; *BMC Public Health;* 11; 770). Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

Voltage-gated calcium channels (VGCC) are required for many key functions in the body. Different subtypes of voltage-gated calcium channels have been described (Zamponi et al.; *Pharmacol. Rev.;* 2015; 67; 821-870). The VGCC are assembled through interactions of different subunits, namely α1 ($Ca_v\alpha1$), β ($Ca_v\beta$) α2δ ($Ca_v\alpha2\delta$) and γ ($Ca_v\gamma$). The α1 subunits are the key porous forming units of the channel complex, being responsible for $Ca^{2+}$ conduction and generation of $Ca^{2+}$ influx. The α2δ, β, and γ subunits are auxiliary, although they are very important for the regulation of the channel since they increase the expression of the α1 subunits in the plasma membrane as well as modulate their function resulting in functional diversity in different cell types. Based on their physiological and pharmacological properties, VGCC can be subdivided into low voltage-activated T-type ($Ca_v3.1$, $Ca_v3.2$, and $Ca_v3.3$), and high voltage-activated L-($Ca_v1.1$ through $Ca_v1.4$), N—($Ca_v2.2$), P/Q-($Ca_v2.1$), and R—($Ca_v2.3$) types, depending on the channel forming Cava subunits. All of these five subclasses are found in the central and peripheral nervous systems. Regulation of intracellular calcium through activation of these VGCC plays obligatory roles in: 1) neurotransmitter release, 2) membrane depolarization and hyperpolarization, 3) enzyme activation and inactivation, and 4) gene regulation (Perret and Luo; Neurotherapeutics; 2009; 6; 679-692; Zamponi et al., 2015; Neumaier et al.; Prog. Neurobiol.; 2015; 129; 1-36). A large body of data has clearly indicated that VGCC are implicated in mediating various disease states including pain processing. Drugs interacting with the different calcium channel subtypes and subunits have been developed. Current therapeutic agents include drugs targeting the L-type $Ca_v1.2$ calcium channels, particularly 1,4-dihydropyridines, which are widely used in the treatment of hypertension. T-type ($Ca_v3$) channels are the target of ethosuximide, widely used in absence epilepsy. Ziconotide, a peptide blocker of the N-type ($Ca_v2.2$) calcium channels, has been approved as a treatment of intractable pain.

The $Ca_v1$ and $Ca_v2$ subfamilies contain an auxiliary α2δ subunit which is the therapeutic target of the gabapentinoid drugs of value in certain epilepsies and chronic neuropathic pain (Perret and Luo, 2009; Vink and Alewood; British J. Pharmacol.; 2012; 167; 970-989). To date, there are four known α2δ subunits, each encoded by a unique gene and all possessing splice variants. Each α2δS protein is encoded by a single messenger RNA and is post-translationally cleaved and then linked by disulfide bonds. Four genes encoding the α2δ subunits have now been cloned. The α2δ-1 was initially cloned from skeletal muscle and shows a fairly ubiquitous distribution. The α2δ-2 and α2δ-3 subunits were subsequently cloned from brain. The most recently identified subunit, the α2δ-4, is largely non-neuronal. The human α2δ-4 protein sequence shares 30, 32 and 61% identity with the human α2δ-1, α2δ-2 and α2δ-3 subunits, respectively. The gene structure of all the α2δ subunits is similar. All the α2δ subunits show several splice variants (Davies et al.; Trends Pharmacol. Sci.; 2007; 28; 220-228; Dolphin, A. C.; Nat. Rev. Neurosci.; 2012; 13; 542-555; Dolphin, A. C.; Biochim. Biophys. Acta; 2013; 1828; 1541-1549).

The $Ca_v\alpha2\delta$-1 subunit may play an important role in neuropathic pain development (Perret and Luo, 2009; Vink and Alewood, 2012). Biochemical data have indicated a significant $Ca_v\alpha2\delta$-1, but not a $Ca_v\alpha2\delta$-2, subunit upregulation in the spinal dorsal horn, and DRG (dorsal root ganglia) after nerve injury that correlates with neuropathic pain development. In addition, blocking axonal transport of injury-induced DRG $Ca_v\alpha2\delta$-1 subunit to the central presynaptic terminals diminishes tactile allodynia in nerve injured animals, suggesting that elevated DRG $Ca_v\alpha2\delta$-1 subunit contributes to neuropathic allodynia.

The $Ca_v\alpha2\delta$-1 subunit (and the $Ca_v\alpha2\delta$-2, but not the $Ca_v\alpha2\delta$-3 and the $Ca_v\alpha2\delta$-4, subunits) is the binding site for gabapentin which has anti-allodynic/hyperalgesic properties in patients and animal models. Because the injury-induced $Ca_v\alpha2\delta$-1 expression correlates with neuropathic pain, development and maintenance, and various calcium channels are known to contribute to spinal synaptic neurotransmission and DRG neuron excitability, the injury-induced $Ca_v\alpha2\delta$-1 subunit upregulation may contribute to the initiation and maintenance of neuropathic pain by altering the properties and/or distribution of VGCC in the subpopulation of DRG neurons and their central terminals, therefore modulating excitability and/or synaptic neuroplasticity in the dorsal horn. Intrathecal antisense oligonucleotides against the $Ca_v\alpha2\delta$-1 subunit can block nerve injury-induced $Ca_v\alpha2\delta$-1 upregulation and prevent the onset of allodynia and reserve established allodynia.

As above mentioned, the α2δ subunits of VGCC form the binding site for gabapentin and pregabalin which are structural derivatives of the inhibitory neurotransmitter GABA although they do not bind to GABAA, GABAB, or benzodiazepine receptors, or alter GABA regulation in animal brain preparations. The binding of gabapentin and pregabalin to the $Ca_v\alpha2\delta$-1 subunit results in a reduction in the calcium-dependent release of multiple neurotransmitters, leading to efficacy and tolerability for neuropathic pain management. Gabapentinoids may also reduce excitability by inhibiting synaptogenesis (Perret and Luo, 2009; Vink and Alewood, 2012, Zamponi et al., 2015).

Thus, the present invention relates to compounds with inhibitory effect towards the α2δ subunits of voltage-gated calcium channels, preferably towards the α2δ-1 subunit of voltage-gated calcium channels.

It is also known that Noradrenaline (NA), also called norepinephrine, functions in the human brain and body as a hormone and neurotransmitter. Noradrenaline exerts many effects and mediates a number of functions in living organisms. The effects of noradrenaline are mediated by two distinct super-families of receptors, named alpha- and beta-adrenoceptors. They are further divided into subgroups exhibiting specific roles in modulating behavior and cognition of animals. The release of the neurotransmitter noradrenaline throughout the mammalian brain is important for modulating attention, arousal, and cognition during many behaviors (Mason, S. T.; Prog. Neurobiol.; 1981; 16; 263-303).

The noradrenaline transporter (NET, SLC6A2) is a monoamine transporter mostly expressed in the peripheral and central nervous systems. The NET recycles primarily NA, but also serotonin and dopamine, from synaptic spaces into presynaptic neurons.

The NET is a target of drugs treating a variety of mood and behavioral disorders, such as depression, anxiety, and attention-deficit/hyperactivity disorder (ADHD). Many of these drugs inhibit the uptake of NA into the presynaptic cells through NET. These drugs therefore increase the availability of NA for binding to postsynaptic receptors that regulate adrenergic neurotransmission. The NET inhibitors can be specific. For example, the ADHD drug atomoxetine is a NA reuptake inhibitor (NRI) that is highly selective for NET. Reboxetine was the first NRI of a new antidepressant class (Kasper et al.; Expert Opin. Pharmacother.; 2000; 1; 771-782). Some NET inhibitors also bind multiple targets, increasing their efficacy as well as their potential patient population.

Endogenous, descending noradrenergic fibers impose analgesic control over spinal afferent circuitry mediating the transmission of pain signals (Ossipov et al.; J. Clin. Invest.; 2010; 120; 3779-3787). Alterations in multiple aspects of noradrenergic pain processing have been reported, especially in neuropathic pain states (Ossipov et a., 2010; Wang et al.; J. Pain; 2013; 14; 845-853). Numerous studies have demonstrated that activation of spinal α2δ-adrenergic receptors exerts a strong antinociceptive effect. Spinal clonidine blocked thermal and capsaicin-induced pain in healthy human volunteers (Ossipov et al., 2010). Noradrenergic reuptake inhibitors have been used for the treatment of chronic pain for decades: most notably the tricyclic antidepressants, amitriptyline, and nortriptyline. Once released from the presynaptic neuron, NA typically has a short-lived effect, as much of it is rapidly transported back into the nerve terminal. In blocking the reuptake of NA back into the presynaptic neurons, more neurotransmitter remains for a longer period of time and is therefore available for interaction with pre- and postsynaptic α2δ-adrenergic receptors (AR). Tricyclic antidepressants and other NA reuptake inhibitors enhance the antinociceptive effect of opioids by increasing the availability of spinal NA. The $α_2$A-AR subtype is necessary for spinal adrenergic analgesia and synergy with opioids for most agonist combinations in both animal and humans (Chabot-Doré et al.; Neuropharmacology; 2015; 99; 285-300). A selective upregulation of spinal NET in a rat model of neuropathic pain with concurrent downregulation of serotonin transporters has been shown (Fairbanks et al.; Pharmacol. Ther.; 2009; 123; 224-238). Inhibitors of NA reuptake such as nisoxetine, nortriptyline and maprotiline and dual inhibitors of the noradrenaline and serotonin reuptake such as imipramine and milnacipran produce potent anti-nociceptive effects in the formalin model of tonic pain. Neuropathic pain resulting from the chronic constriction injury of the sciatic nerve was prevented by the dual uptake inhibitor, venlafaxine. In the spinal nerve ligation model, amitriptyline, a non-selective serotonin and noradrenaline reuptake blocker, the preferential noradrenaline reuptake inhibitor, desipramine and the selective serotonin and noradrenaline reuptake inhibitors, milnacipran and duloxetine, produce a decrease in pain sensitivity whereas the selective serotonin reuptake inhibitor, fluoxetine, is ineffective (Mochizucki, D.; Psychopharmacol.; 2004; Supplm. 1; S15-S19; Hartrick, C. T.; Expert Opin. Investig. Drugs; 2012; 21; 1827-1834). A number of nonselective investigational agents focused on noradrenergic mechanisms with the potential for additive or even synergistic interaction between multiple mechanisms of action are being developed (Hartrick, 2012).

Polypharmacology is a phenomenon in which a drug binds multiple rather than a single target with significant affinity. The effect of polypharmacology on therapy can be positive (effective therapy) and/or negative (side effects). Positive and/or negative effects can be caused by binding to the same or different subsets of targets; binding to some targets may have no effect. Multi-component drugs or multi-targeting drugs can overcome toxicity and other side effects associated with high doses of single drugs by countering biological compensation, allowing reduced dosage of each compound or accessing context-specific multitarget mechanisms. Because multitarget mechanisms require their targets to be available for coordinated action, one would expect synergies to occur in a narrower range of cellular phenotypes given differential expression of the drug targets than would the activities of single agents. In fact, it has been experimentally demonstrated that synergistic drug combinations are generally more specific to particular cellular contexts than are single agent activities, such selectivity is achieved through differential expression of the drugs' targets in cell types associated with therapeutic, but not toxic, effects (Lehar et al.; Nat. Biotechnol.; 2009; 27; 659-666).

In the case of chronic pain, which is a multifactorial disease, multi-targeting drugs may produce concerted pharmacological intervention of multiple targets and signaling pathways that drive pain. Because they actually make use of biological complexity, multi-targeting (or multi-component drugs) approaches are among the most promising avenues toward treating multifactorial diseases such as pain (Gilron et al.; Lancet Neurol.; 2013; 12(11); 1084-1095). In fact, positive synergistic interaction for several compounds, including analgesics, has been described (Schröder et al; J. Pharmacol. Exp. Ther.; 2011; 337; 312-320; Zhang et al.; Cell Death Dis.; 2014; 5; e1138; Gilron et al., 2013).

Given the significant differences in pharmacokinetics, metabolisms and bioavailability, reformulation of drug combinations (multi-component drugs) is challenging. Further, two drugs that are generally safe when dosed individually cannot be assumed to be safe in combination. In addition to the possibility of adverse drug-drug interactions, if the theory of network pharmacology indicates that an effect on phenotype may derive from hitting multiple targets, then that combined phenotypic perturbation may be efficacious or deleterious. The major challenge to both drug combination strategies is the regulatory requirement for each individual drug to be shown to be safe as an individual agent and in combination (Hopkins, A. L.; Nat. Chem. Biol.; 2008; 4; 682-690).

An alternative strategy for multitarget therapy is to design a single compound with selective polypharmacology (multi-targeting drug). It has been shown that many approved drugs act on multiple targets. Dosing with a single compound may have advantages over a drug combination in terms of equitable pharmacokinetics and biodistribution. Indeed, troughs in drug exposure due to incompatible pharmacokinetics between components of a combination therapy may create a low-dose window of opportunity where a reduced selection pressure can lead to drug resistance. In terms of drug registration, approval of a single compound acting on multiple targets faces significantly lower regulatory barriers than approval of a combination of new drugs (Hopkins, 2008).

Thus, in a preferred embodiment, the compounds of the present invention having affinity for the α2δ subunits of voltage-gated calcium channels, preferably towards the α2δ-1 subunit of voltage-gated calcium channels, additionally have inhibitory effect towards the noradrenaline transporter (NET) and are, thus, more effective to treat chronic pain.

There are two potentially important interactions between the NET and the α2δ-1 subunit inhibition: 1) synergism in analgesia, thus reducing the risk of specific side effects; and 2) inhibition of pain-related affective comorbidities such as anxiety and/or depressive-like behaviors (Nicolson et al.; Harv. Rev. Psychiatry; 2009; 17; 407-420).

1) Preclinical research has demonstrated that gabapentinoids attenuated pain-related behaviors through supraspinal activation of the descending noradrenergic system (Tanabe et al.; J. Neuroosci. Res.; 2008; Hayashida, K.; Eur. J. Pharmacol.; 2008; 598; 21-26). In consequence, the α2δ-1-related analgesia mediated by NA-induced activation of spinal α$_2$-adrenergic receptors can be potentiated by the inhibition of the NET. Some evidence from combination studies in preclinical models of neuropathic pain exist. Oral duloxetine with gabapentin was additive to reduce hypersensitivity induced by nerve injury in rats (Hayashida; 2008). The combination of gabapentin and nortriptyline drugs was synergic in mice submitted to orofacial pain and to peripheral nerve injury model (Miranda, H. F. et al.; J. Orofac. Pain; 2013; 27; 361-366; Pharmacology; 2015; 95; 59-64), 2) Drug modulation of the NET and the α2δ-1 subunit has been shown to produce antidepressant and anti-anxiety effects respectively (Frampton, J. E.; CNS Drugs; 2014; 28; 835-854; Hajós, M. et al.; CNS Drug Rev.; 2004; 10; 23-44). In consequence, a dual drug that inhibited the NET and α2δ-1 subunit of VGCC may also stabilize pain-related mood impairments by acting directly on both physical pain and the possible mood alterations.

SUMMARY OF THE INVENTION

The present invention discloses novel compounds with great affinity to the α2δ subunit of voltage-gated calcium channels, more specifically to the α2δ-1 subunit, and which in preferred embodiments also have inhibitory effect towards the noradrenaline transporter (NET), thus resulting in a dual activity for treating pain and pain related disorders.

The main object of the present invention is related to compounds of general formula (I):

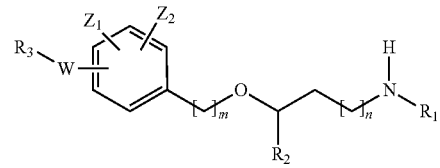

(I)

wherein:

$R_1$ is a branched or unbranched $C_{1-6}$ alkyl radical or a $C_{1-6}$ haloalkyl radical; $R_2$ is a 6-membered aryl optionally substituted by a halogen atom, a branched or unbranched $C_{1-6}$-alkyl radical, a branched or unbranched $C_{1-6}$-alkoxy radical, a $C_{1-6}$-haloalcoxy radical, a $C_{1-6}$-haloalkyl radical or a hydroxyl radical; or 5 or 6-membered heteroaryl having at least one heteroatom selected from N, O and S;

n and m are independently 0 or 1;

$Z_1$ and $Z_2$ are independently selected from a hydrogen atom; a branched or unbranched $C_{1-6}$-alkyl radical; a halogen atom; a branched or unbranched $C_{1-6}$-alkoxy radical; a $C_{3-6}$ cycloalkyl radical; a $C_{1-6}$-haloalkyl radical; and a $C_{1-6}$-haloalcoxy radical;

—W—$R_3$ is in meta or para position;

W is —$(CH_2)_p$—; —C(O)—; or a bond;

p is 1 or 2;

$R_3$ represents one of the following moieties:

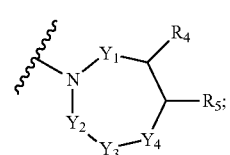

(IA)

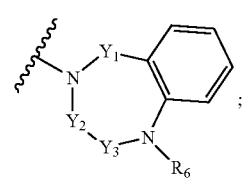

(IB)

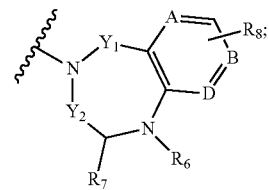

(IC)

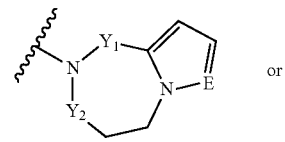

(ID)

or

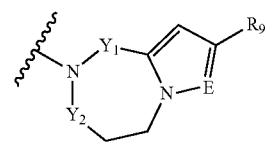

(IE)

wherein
Y$_1$ and Y$_2$ are independently —CH$_2$— or —C(O)—;
Y$_3$ is —CHR$_7$— or —C(O)—;
Y$_4$ is —CH— or —N—R$_6$;
R$_4$ and R$_5$ are independently a hydrogen atom, a branched or unbranched C$_{1-6}$ alkyl radical or a —(CH$_2$)$_q$—NRR' radical where q is 0 or 1 and R and R' independently represent a hydrogen atom or a branched or unbranched C$_{1-6}$-alkyl radical; one or two from A, B and D represent —N— and the others are —CH—;
E represents —N— or —CH—;
R$_6$ is a hydrogen atom; a branched or unbranched C$_{1-6}$ alkyl radical; or a —C(O)—CH$_2$—NR$_{6a}$R$_{6b}$ radical where R$_{6a}$ and R$_{6b}$ independently represent a hydrogen atom or a branched or unbranched C$_{1-6}$-alkyl radical;
R$_7$ is a hydrogen atom;
or alternatively, R$_6$ and R$_7$ may form a 5 or 6-membered heterocycloalkyl group;
R$_8$ is a hydrogen atom, a branched or unbranched C$_{1-6}$-alkyl radical; a halogen atom; a branched or unbranched C$_{1-6}$-alkoxy radical; a hydroxyl radical; a C$_{1-6}$-haloalkyl radical; or a —NR$_{8a}$R$_{8b}$ radical where R$_{8a}$ and R$_{8b}$ are independently a hydrogen atom or a branched or unbranched C$_{1-6}$-alkyl radical;
R$_9$ is a branched or unbranched C$_{1-6}$-alkyl radical; or a branched or unbranched C$_{1-6}$-alkoxy radical;
or a pharmaceutically acceptable salt, isomer, prodrug or solvate thereof.

It is also an object of the invention different processes for the preparation of compounds of formula (I).

Another object of the invention refers to the use of such compounds of general formula (I) for the treatment and/or prophylaxis of the α2δ-1 subunit mediated disorders and more preferably for the treatment and/or prophylaxis of disorders mediated by the α2δ-1 subunit of voltage-gated calcium channels and/or the noradrenaline transporter (NET). The compounds of the present invention are particularly suited for the treatment of pain, specially neuropathic pain, and pain related or pain derived conditions.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenteral, such as pulmonary, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to compounds of general formula (I)

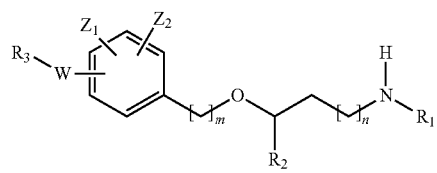

(I)

wherein:
R$_1$ is a branched or unbranched C$_{1-6}$ alkyl radical or a C$_{1-6}$ haloalkyl radical; R$_2$ is a 6-membered aryl optionally substituted by a halogen atom, a branched or unbranched C$_{1-6}$-alkyl radical, a branched or unbranched C$_{1-6}$-alkoxy radical, a C$_{1-6}$-haloalcoxy radical, a C$_{1-6}$-haloalkyl radical or a hydroxyl radical; or a 5 or 6-membered heteroaryl having at least one heteroatom selected from N, O and S;
n and m are independently 0 or 1;
Z$_1$ and Z$_2$ are independently selected from a hydrogen atom; a branched or unbranched C$_{1-6}$-alkyl radical; a halogen atom; a branched or unbranched C$_{1-6}$-alkoxy radical; a C$_{3-6}$ cycloalkyl radical; a C$_{1-6}$-haloalkyl radical; and a C$_{1-6}$-haloalcoxy radical;
—W—R$_3$ is in meta or para position;
W is —(CH$_2$)$_p$—; —C(O)—; or a bond;
p is 1 or 2; R$_3$ represents one of the following moieties:

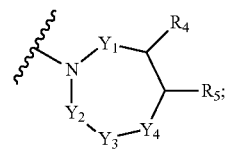

(IA)

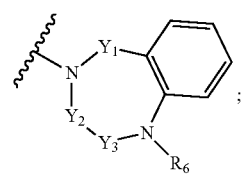

(IB)

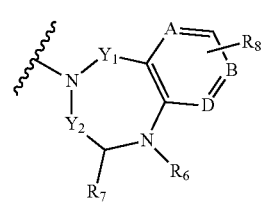

(IC)

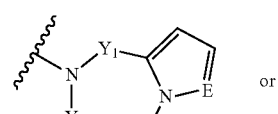

(ID)

or

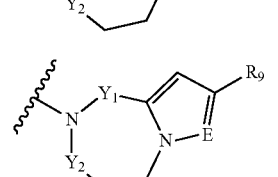

(IE)

wherein
Y$_1$ and Y$_2$ are independently —CH$_2$— or —C(O)—;
Y$_3$ is —CHR$_7$— or —C(O)—;
Y$_4$ is —CH— or —N—R$_6$;
R$_4$ and R$_5$ are independently a hydrogen atom, a branched or unbranched C$_{1-6}$ alkyl radical or a —(CH$_2$)$_q$—NRR' radical where q is 0 or 1 and R and R' independently represent a hydrogen atom or a branched or unbranched C$_{1-6}$-alkyl radical;
one or two from A, B and D represent —N— and the others are —CH—;
E represents —N— or —CH—;

$R_6$ is a hydrogen atom; a branched or unbranched $C_{1-6}$ alkyl radical; or a —C(O)—CH$_2$—NR$_{6a}$R$_{6b}$ radical where $R_{6a}$ and $R_{6b}$ independently represent a hydrogen atom or a branched or unbranched $C_{1-6}$-alkyl radical;

$R_7$ is a hydrogen atom;

or alternatively, $R_6$ and $R_7$ may form an 5 or 6-membered heterocycloalkyl group;

$R_8$ is a hydrogen atom, a branched or unbranched $C_{1-6}$-alkyl radical; a halogen atom; a branched or unbranched $C_{1-6}$-alkoxy radical; a hydroxyl radical; a $C_{1-6}$-haloalkyl radical; or a —NR$_{8a}$R$_{8b}$ radical where $R_{8a}$ and $R_{8b}$ are independently a hydrogen atom or a branched or unbranched $C_{1-6}$-alkyl radical;

$R_9$ is a branched or unbranched $C_{1-6}$-alkyl radical; or a branched or unbranched $C_{1-6}$-alkoxy radical;

or a pharmaceutically acceptable salt, isomer, prodrug or solvate thereof.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

Any compound referred to herein is intended to represent such specific compound as well as certain variations or forms. In particular, compounds referred to herein may have asymmetric centers and therefore may exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

"Halogen" or "halo" as referred in the present invention represent fluorine, chlorine, bromine or iodine. When the term "halo" is combined with other substituents, such as for instance "$C_{1-6}$ haloalkyl" or "$C_{1-6}$ haloalkoxy" it means that the alkyl or alkoxy radical can respectively contain at least one halogen atom.

A "leaving group" is a group that in a heterolytic bond cleavage keeps the electron pair of the bond. Suitable leaving groups are well known in the art and include Cl, Br, I and —O—SO$_2$R$^{14}$, wherein R$^{14}$ is F, $C_{1-4}$-alkyl, $C_{1-4}$-haloalkyl, or optionally substituted phenyl.

The preferred leaving groups are Cl, Br, I, tosylate, mesylate, triflate, nonaflate and fluorosulphonate.

"$C_{1-6}$ alkyl", as referred to in the present invention, are saturated aliphatic radicals. They may be linear (unbranched) or branched and are optionally substituted. $C_{1-6}$ alkyl as expressed in the present invention means an alkyl radical of 1, 2, 3, 4, 5 or 6 carbon atoms. Preferred alkyl radicals according to the present invention include but are not restricted to methyl, ethyl, propyl, n-propyl, isopropyl, butyl, n-butyl, tert-butyl, isobutyl, sec-butyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl or 1-methylpentyl. The most preferred alkyl radical are $C_{1-4}$ alkyl, such as methyl, ethyl, propyl, n-propyl, isopropyl, butyl, n-butyl, tert-butyl, isobutyl, sec-butyl, 1-methylpropyl, 2-methylpropyl or 1,1-dimethylethyl. Alkyl radicals, as defined in the present invention, may be optionally mono- or polysubstituted by substitutents independently selected from a halogen atom, a branched or unbranched $C_{1-6}$-alkoxy radical, a branched or unbranched $C_{1-6}$-alkyl radical, a $C_{1-6}$-haloalcoxy radical, a $C_{1-6}$-haloalkyl radical, a trihaloalkyl radical, a hydroxyl radical and an amino radical such as —NR$_{4a}$R$_{4b}$ radical.

"$C_{1-6}$ alkoxy" as referred to in the present invention, is understood as meaning an alkyl radical as defined above attached via oxygen linkage to the rest of the molecule. Examples of alkoxy include, but are not limited to methoxy, ethoxy, propoxy, butoxy or tert-butoxy.

"$C_{3-6}$ Cycloalkyl" as referred to in the present invention, is understood as meaning saturated and unsaturated (but not aromatic), cyclic hydrocarbons having from 3 to 6 carbon atoms which can optionally be unsubstituted, mono- or polysubstituted.

Examples for cycloalkyl radical preferably include but are not restricted to cyclopropyl, cyclobutyl, cyclopentyl, or cyclohexyl. Cydoalkyl radicals, as defined in the present invention, are optionally mono- or polysubstituted by substitutents independently selected from a halogen atom, a branched or unbranched $C_{1-6}$-alkyl radical, a branched or unbranched $C_{1-6}$-alkoxy radical, a $C_{1-6}$-haloalcoxy radical, a $C_{1-6}$-haloalkyl radical, a trihaloalkyl radical or a hydroxyl radical.

"Heterocycloalkyl" as referred to in the present invention, are understood as meaning saturated and unsaturated (but not aromatic), generally 5 or 6 membered cyclic hydrocarbons which can optionally be unsubstituted, mono- or polysubstituted and which have at least one heteroatom in their structure selected from N, O and S. Examples for heterocycloalkyl radical preferably include but are not restricted to pyrroline, pyrrolidine, pyrazoline, aziridine, azetidine, tetrahydropyrrole, oxirane, oxetane, dioxetane, tetrahydropyrane, tetrahydrofurane, dioxane, dioxolane, oxazolidine, piperidine, piperazine, morpholine, azepane or diazepane. Heterocycloalkyl radicals, as defined in the present invention, may be optionally mono- or polysubstituted by substitutents independently selected from a halogen atom, a branched or unbranched $C_{1-6}$-alkyl radical, a branched or unbranched $C_{1-6}$-alkoxy radical, a $C_{1-6}$-haloalkoxy radical, a $C_{1-6}$-haloalkyl radical, a trihaloalkyl radical and a hydroxyl radical. More preferably heterocycloalkyl in the context of the present invention are 5 or 6-membered ring systems optionally at least monosubstituted.

"Aryl" as referred to in the present invention, is understood as meaning ring systems with at least one aromatic ring but without heteroatoms even in only one of the rings. These aryl radicals may optionally be mono- or polysubstituted by substituents independently selected from a halogen atom, a branched or unbranched $C_{1-6}$-alkyl radical, a branched or unbranched $C_{1-6}$-alkoxy radical, a $C_{1-6}$-haloalcoxy radical, a $C_{1-6}$-haloalkyl radical and a hydroxyl radical. Preferred examples of aryl radicals include but are not restricted to phenyl, naphthyl, fluoranthenyl, fluorenyl, tetralinyl, indanyl or anthracenyl radicals, which may optionally be mono- or polysubstituted, if not defined otherwise. More preferably aryl in the context of the present invention is a 6-membered ring system optionally at least monosubstituted.

"Heteroaryl" as referred to in the present invention, is understood as meaning heterocyclic ring systems which have at least one aromatic ring and may optionally contain one or more heteroatoms selected from the group consisting of N, O and S and may optionally be mono- or polysubstituted by substituents independently selected from a halogen atom, a branched or unbranched $C_{1-6}$-alkyl radical, a branched or unbranched $C_{1-6}$-alkoxy radical, a $C_{1-6}$-haloalkoxy radical, a $C_{1-6}$-haloalkyl radical, a trihaloalkyl radical and a hydroxyl radical. Preferred examples of heteroaryls include but are not restricted to furan, benzofuran, pyrrole, pyridine, pyrimidine, pyridazine, pyrazine, thiophene, quinoline, isoquinoline, phthalazine, triazole, pyrazole, isoxazole, indole, benzotriazole, benzodioxolane, benzodioxane, benzimidazole, carbazole or quinazoline. More preferably heteroaryl in the context of the present invention are 5 or 6-membered ring systems optionally at least monosubstituted.

"Heterocyclic system", as defined in the present invention, comprises any saturated, unsaturated or aromatic carbocyclic ring systems which are optionally at least monosubstituted and which contain at least one heteroatom as ring member. Preferred heteroatoms for these heterocyclyl radicals are N, S or O. Preferred substituents for heterocyclyl radicals, according to the present invention, are F, Cl, Br, I, $NH_2$, SH, OH, $SO_2$, $CF_3$, carboxy, amido, cyano, carbamyl, nitro, phenyl, benzyl, $-SO_2NH_2$, branched or unbranched $C_{1-6}$ alkyl and/or branched or unbranched $C_{1-6}$-alkoxy.

The term "ring system" according to the present invention refers to a system consisting of at least one ring of connected atoms but including also systems in which two or more rings of connected atoms are joined with "joined" meaning that the respective rings are sharing one (like a spiro structure), two or more atoms being a member or members of both joined rings. The "ring system" thus defined comprises saturated, unsaturated or aromatic carbocyclic rings which contain optionally at least one heteroatom as ring member and which are optionally at least mono-substituted and may be joined to other carbocyclic ring systems such as aryl radicals, heteroaryl radicals, cycloalkyl radicals etc.

The terms "condensed", "annulated" or "annelated" are also used by those skilled in the art to designate this kind of join.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition particularly includes physiologically acceptable salts, this term must be understood as equivalent to "pharmacologically acceptable salts".

The term "pharmaceutically acceptable salts" in the context of this invention means any salt that is tolerated physiologically (normally meaning that it is not toxic, particularly as a result of the counter-ion) when used in an appropriate manner for a treatment, particularly applied or used in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids-particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, or amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular and preferred embodiment of the invention, $R_2$ is a phenyl radical optionally substituted by a halogen atom, a branched or unbranched $C_{1-6}$-alkyl radical, a branched or unbranched $C_{1-6}$-alkoxy radical, a $C_{1-6}$haloalcoxy radical, a $C_{1-f}$-haloalkyl radical or a hydroxyl radical; or an optionally substituted thiophene radical. More preferably, the phenyl radical is unsubstituted or substituted by a halogen atom, preferably F, and the thiophene radical is unsubstituted.

In another particular and preferred embodiment of the invention, $R_3$ is selected from:

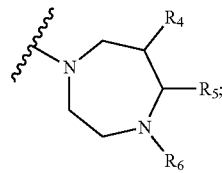
(IA$_1$)

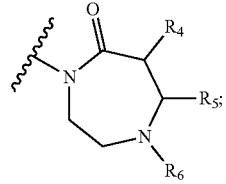
(IA$_2$)

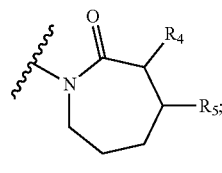
(IA$_3$)

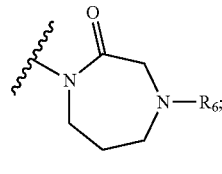
(IA$_4$)

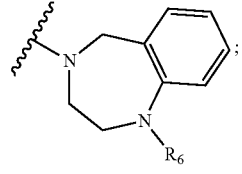
(IB$_1$)

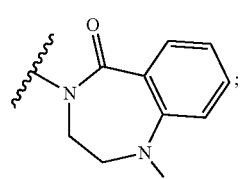
(IB$_2$)

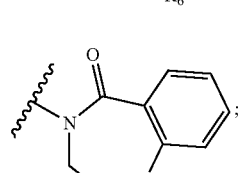
(IB$_3$)

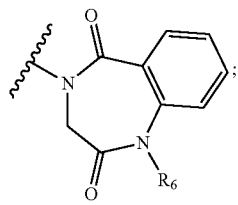
(IB$_4$)

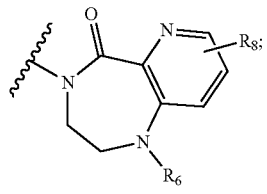
(IC$_1$)

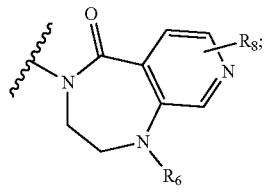
(IC$_2$)

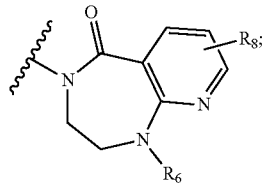
(IC$_3$)

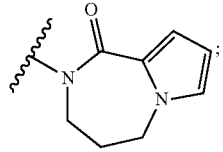
(ID$_1$)

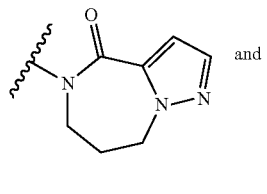
(ID$_2$) and (IE$_1$)

wherein $R_4$, $R_5$, $R_6$, $R_8$ and $R_9$ are as defined before.

In another particular and preferred embodiment of the invention, $R_3$ is selected from:

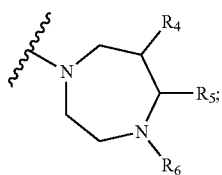 (IA₁)

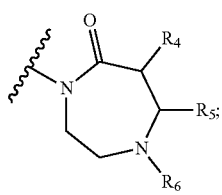 (IA₂)

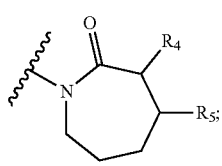 (IA₃)

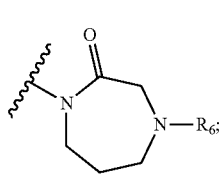 (IA₄)

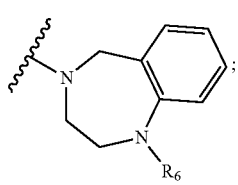 (IB₁)

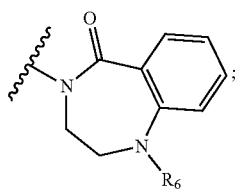 (IB₂)

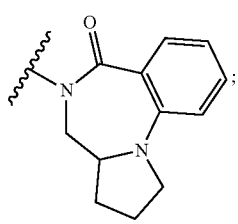 (IB₃)

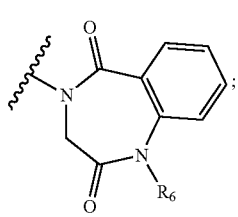 (IB₄)

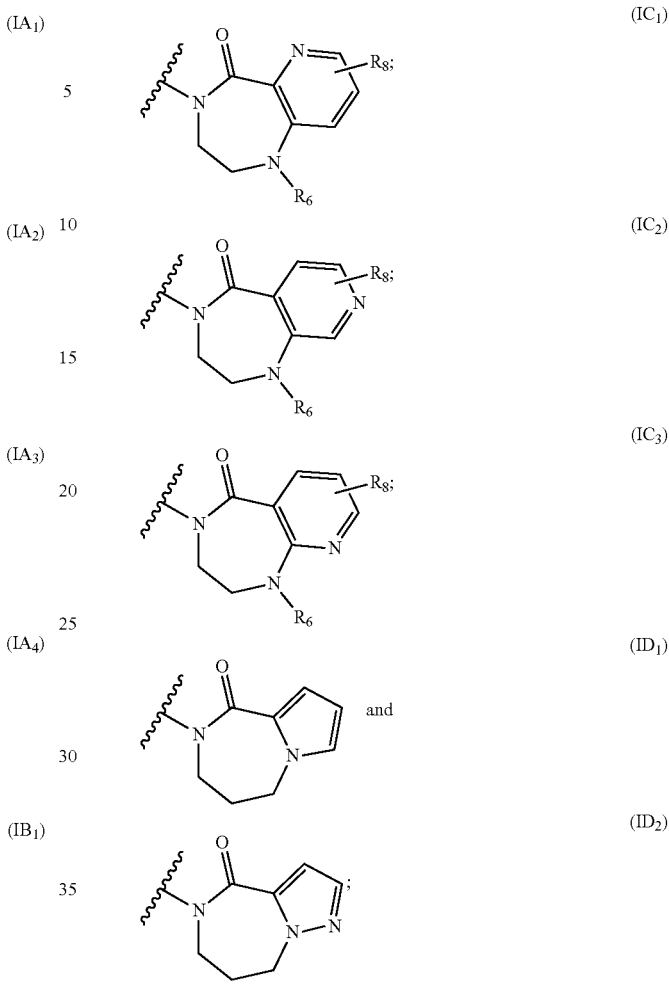

wherein $R_4$, $R_5$, $R_6$ and $R_8$ are as defined before.

In a still particular embodiment of the invention, $Z_1$ and $Z_2$ are independently selected from a hydrogen atom; a branched or unbranched $C_{1-6}$-alkyl radical; a $C_{3-6}$ cycloalkyl radical; and a halogen atom. In a preferred embodiment of the invention, $Z_1$ and $Z_2$ independently represent hydrogen atom, F, cyclopropyl or methyl. In another still particular embodiment of the invention. $Z_1$ and $Z_2$ are independently selected from a hydrogen atom; a branched or unbranched $C_{1-6}$-alkyl radical; and a halogen atom. In a preferred embodiment of the invention, $Z_1$ and $Z_2$ independently represent hydrogen atom, F or methyl. In a more preferred embodiment of the invention, $Z_1$ and $Z_2$ represent a hydrogen atom.

Another particular embodiment of the invention is that where $R_4$ and $R_5$ are independently a hydrogen atom or a —$(CH_2)_q$—NRR' radical where q is 0 or 1 and R and R' are independently a hydrogen atom or a branched or unbranched $C_{1-6}$-alkyl radical, preferably ethyl. In a preferred embodiment of the invention $R_4$ and $R_5$ independently represent hydrogen atom or a —$(CH_2)_q$—NRR' radical where q is 1 and R and R' are independently hydrogen atom or ethyl. In the preferred embodiment of the invention both $R_4$ and $R_5$ represent hydrogen atom or one of them represents hydrogen atom and the other a —$(CH_2)_p$—NRR' radical where q is 1, R is hydrogen atom and R' is ethyl.

Yet another particular embodiment is that in which $R_6$ is a hydrogen atom; a branched or unbranched $C_{1-6}$ alkyl radical, preferably methyl, ethyl or isopropyl; or a —C(O)—CH$_2$—NR$_{6a}$R$_{6b}$ radical where R$_{6a}$ and R$_{6b}$ are independently a hydrogen atom or a branched or unbranched C$_{1-6}$-alkyl radical, preferably ethyl; and R$_7$ is a hydrogen atom. In a preferred embodiment of the invention R$_6$ is methyl, ethyl, isopropyl or a —C(O)—CH$_2$—NR$_{6a}$R$_{6b}$ radical, being R$_{6a}$ hydrogen atom and R$_{6b}$ ethyl; and R$_7$ is a hydrogen atom.

In a further particular embodiment of the invention, R$_6$ and R$_7$ form a pyrrolidine ring.

Another particular embodiment of the invention contemplates that R is a hydrogen atom; a branched or unbranched C$_{1-6}$-alkyl radical, preferably methyl; a halogen atom, preferably F; a branched or unbranched C$_{1-6}$-alkoxy radical, preferably methoxy; a hydroxyl radical; a C$_{1-6}$-haloalkyl radical, preferably trifluoromethyl; or a —NR$_{8a}$R$_{8b}$ radical where R$_{8a}$ and R$_{8b}$ are independently a hydrogen atom or a branched or unbranched C$_{1-6}$-alkyl radical, preferably methyl or ethyl. Another particular embodiment of the invention contemplates that R$_8$ is a hydrogen atom; a branched or unbranched C$_{1-6}$-alkyl radical, preferably methyl; a halogen atom, preferably F; a branched or unbranched C$_{1-6}$-alkoxy radical, preferably methoxy; a C$_{1-6}$-haloalkyl radical, preferably trifluoromethyl; or a —NR$_{8a}$R$_{8b}$ radical where R$_{8a}$ and R$_{8b}$ are independently a hydrogen atom or a branched or unbranched C$_{1-6}$-alkyl radical, preferably methyl or ethyl. In a preferred embodiment of the invention R$_8$ is a hydrogen atom, methyl, F, methoxy, trifluoromethyl or a —NR$_{8a}$R$_{8b}$ radical where R$_{8a}$, and R$_{8b}$ independently represent a hydrogen atom, methyl or ethyl. In the preferred embodiment R$_8$ is a hydrogen atom.

Another particular embodiment of the invention contemplates that R$_9$ is a methyl or a methoxy.

A particularly preferred embodiment of the invention is represented by compounds of general formula (I) where:

R$_1$ is a branched or unbranched C$_{1-6}$ alkyl radical or a C$_{1-6}$ haloalkyl radical;

R$_2$ is a phenyl radical optionally substituted by a halogen atom, a branched or unbranched C$_{1-6}$-alkyl radical, a branched or unbranched C$_{1-6}$-alkoxy radical, a C$_{1-6}$-haloalcoxy radical, a C$_{1-6}$-haloalkyl radical or a hydroxyl radical; or a unsubstituted thiophene radical;

n and m are independently 0 or 1;

Z$_1$ and Z$_2$ are independently selected from a hydrogen atom; a branched or unbranched C$_{1-6}$-alkyl radical, preferably methyl; a C$_{3-6}$ cycloalkyl radical, preferably cyclopropyl; and a halogen atom, preferably F;

—W—R$_3$ is in meta or para position;

W is —(CH$_2$)$_p$—; —C(O)—; or a bond;

p is 1 or 2;

R$_3$ represents one of the following moieties:

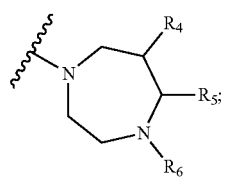
(IA$_1$)

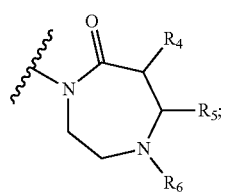
(IA$_2$)

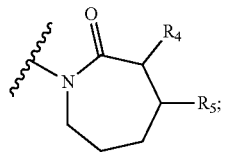
(IA$_3$)

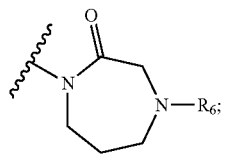
(IA$_4$)

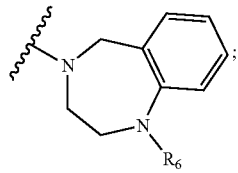
(IB$_1$)

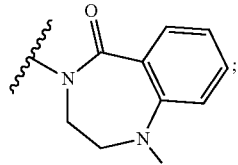
(IB$_2$)

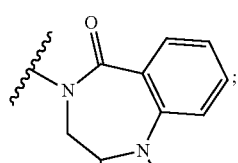
(IB$_3$)

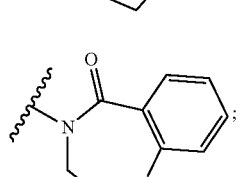
(IB$_4$)

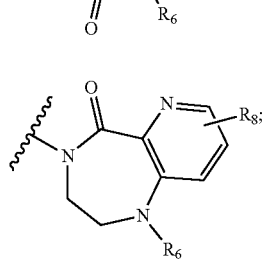
(IC$_1$)

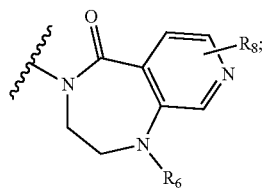
(IC$_2$)

-continued

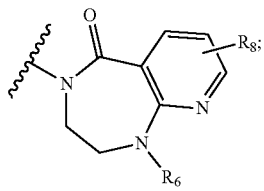
(IC₃)

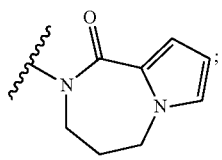
(ID₁)

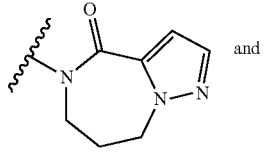
(ID₂)
and

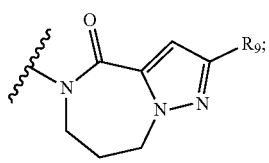
(IE₁)

R₄ and R₅ are independently a hydrogen atom or a —(CH₂)$_q$—NRR' radical where q is 0 or 1 and R and R' are independently a hydrogen atom or a branched or unbranched C$_{1-6}$-alkyl radical, preferably ethyl;

R₆ is a hydrogen atom; a branched or unbranched C$_{1-6}$ alkyl radical, preferably methyl, ethyl or isopropyl; or a —C(O)—CH₂—NR$_{6a}$R$_{6b}$ radical where R$_{6a}$ and R$_{6b}$ are independently a hydrogen atom or a branched or unbranched C$_{1-6}$-alkyl radical, preferably ethyl;

R₇ is a hydrogen atom;

or alternatively, R₆ and R₇ form a pyrrolidine ring;

R₈ is a hydrogen atom; a branched or unbranched C$_{1-6}$-alkyl radical, preferably methyl; a halogen atom, preferably F; a branched or unbranched C$_{1-6}$-alkoxy radical, preferably methoxy; a hydroxyl radical; a C$_{1-6}$-haloalkyl radical, preferably trifluoromethyl; or a —NR$_{8a}$R$_{8b}$ radical where R$_{8a}$ and R$_{8b}$ are independently a hydrogen atom or a branched or unbranched C$_{1-6}$-alkyl radical, preferably methyl or ethyl;

R₉ is a methyl or a methoxy;

or a pharmaceutically acceptable salt, isomer, prodrug or solvate thereof.

Another particularly preferred embodiment of the invention is represented by compounds of general formula (I) where:

R₁ is a branched or unbranched C$_{1-6}$ alkyl radical or a C$_{1-6}$ haloalkyl radical;

R₂ is a phenyl radical optionally substituted by a halogen atom, a branched or unbranched C$_{1-6}$-alkyl radical, a branched or unbranched C$_{1-6}$-alkoxy radical, a C$_{1-6}$-haloalkoxy radical, a C$_{1-6}$-haloalkyl radical or a hydroxyl radical; or a unsubstituted thiophene radical;

n and m are independently 0 or 1;

Z₁ and Z₂ are independently selected from a hydrogen atom; a branched or unbranched C$_{1-6}$-alkyl radical, preferably methyl; and a halogen atom, preferably F;

—W—R₃ is in meta or para position;

W is —(CH₂)—; —C(O)—; or a bond;

p is 1 or 2;

R₃ represents one of the following moieties:

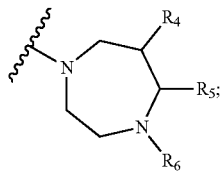
(IA₁)

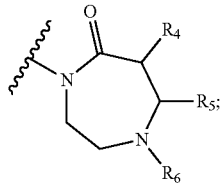
(IA₂)

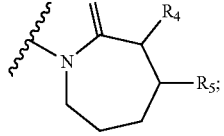
(IA₃)

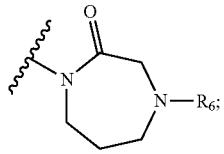
(IA₄)

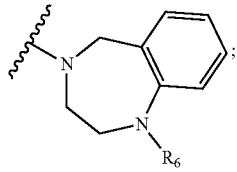
(IB₁)

(IB₂)

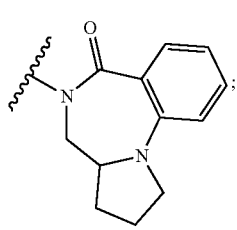
(IB₃)

-continued

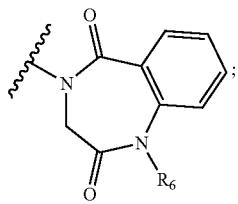
(IB₄)

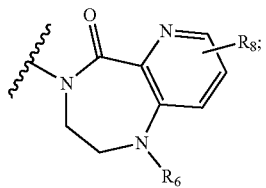
(IC₁)

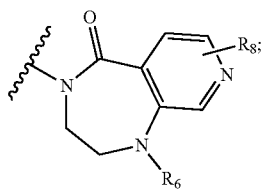
(IC₂)

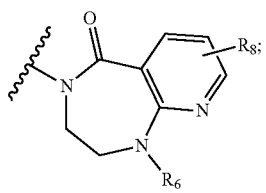
(IC₃)

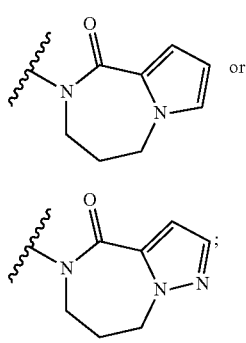
(ID₁) or (ID₂)

$R_4$ and $R_5$ are independently a hydrogen atom or a —(CH$_2$)$_q$—NRR' radical where q is 0 or 1 and R and R' are independently a hydrogen atom or a branched or unbranched $C_{1-6}$ alkyl radical, preferably ethyl;

$R_6$ is a hydrogen atom; a branched or unbranched $C_{1-6}$ alkyl radical, preferably methyl, ethyl or isopropyl; or a —C(O)—CH$_2$—NR$_{6a}$R$_{6b}$ radical where R$_{6a}$ and R$_{6b}$ are independently a hydrogen atom or a branched or unbranched $C_{1-6}$-alkyl radical, preferably ethyl;

$R_7$ is a hydrogen atom;
or alternatively, $R_6$ and $R_7$ form a pyrrolidine ring;

$R_8$ is a hydrogen atom; a branched or unbranched $C_{1-6}$-alkyl radical, preferably methyl; a halogen atom, preferably F; a branched or unbranched $C_{1-6}$-alkoxy radical, preferably methoxy; a $C_{1-6}$-haloalkyl radical, preferably trifluoromethyl; or a —NR$_{8a}$R$_{8b}$ radical where R$_{8a}$ and R$_{8b}$ are independently a hydrogen atom or a branched or unbranched $C_{1-6}$-alkyl radical, preferably methyl or ethyl;

or a pharmaceutically acceptable salt, isomer, prodrug or solvate thereof.

Another particularly preferred embodiment of the invention is represented by compounds of formula (I) having the following subformulas (I$_{1a}$), (I$_{1b}$), (I$_{1c}$), (I$_{2a1}$), (I$_{2a2}$), (I$_{2a3}$), (I$_{2a4}$), (I$_{2b1}$), (I$_{2b2}$), (I$_{2b3}$), (I$_{2b4}$), (I$_{2c1}$), (I$_{2c2}$), (I$_{2c3}$), (I$_{2d1}$), (I$_{2d2}$), (I$_{2d3}$) (I$_{3a}$), (I$_{3b}$) or (I$_{3c}$):

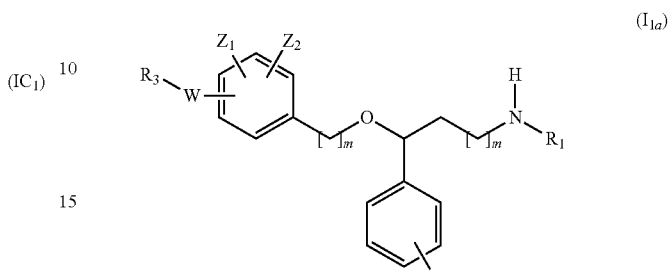
(I₁ₐ)

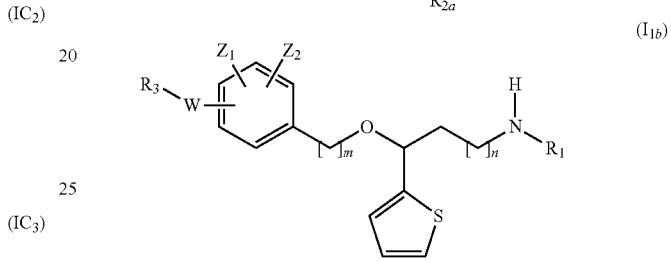
(I₁ᵦ)

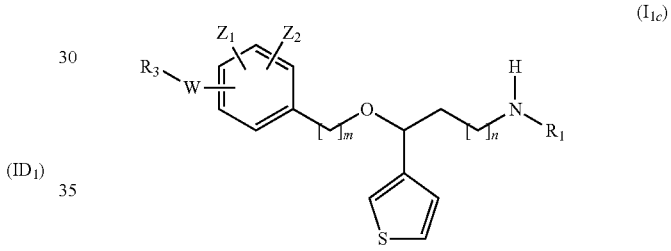
(I₁c)

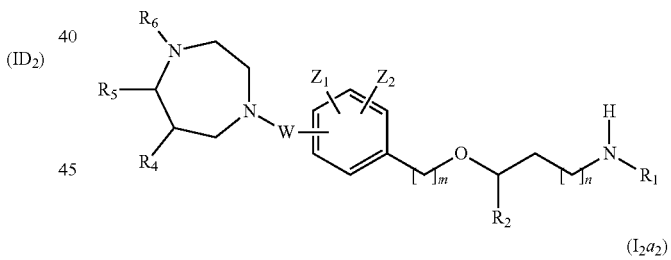
(I₂ₐ₁)

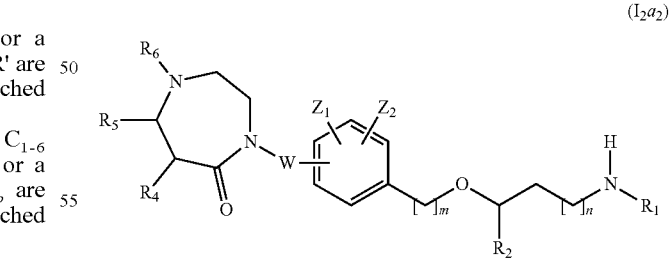
(I₂ₐ₂)

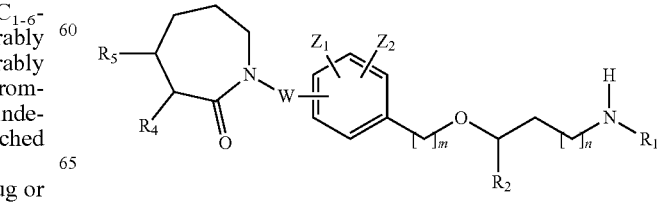
(I₂ₐ₃)

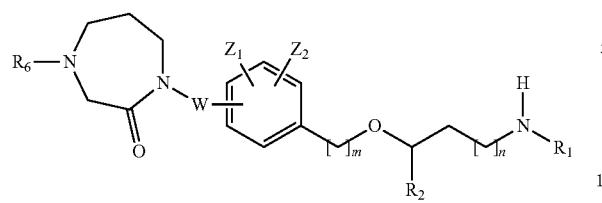
(I2a4)
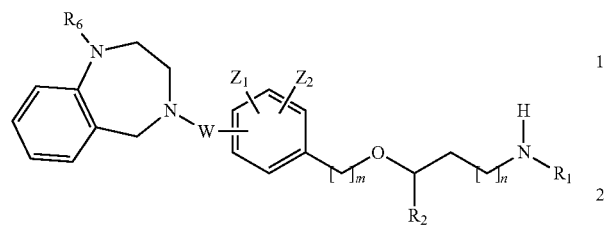
(I2b1)
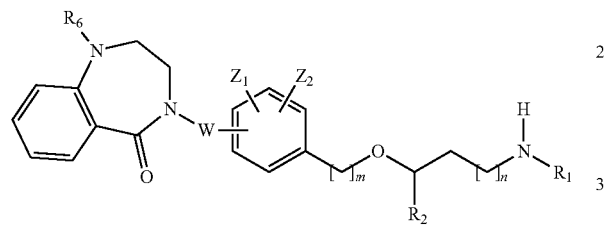
(I2b2)
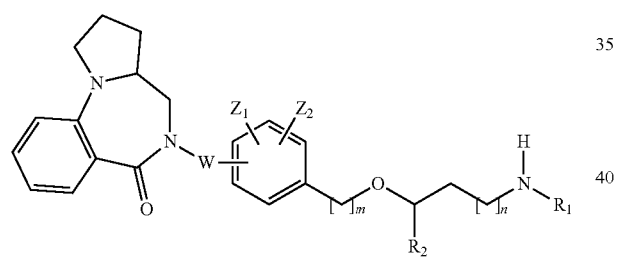
(I2b3)
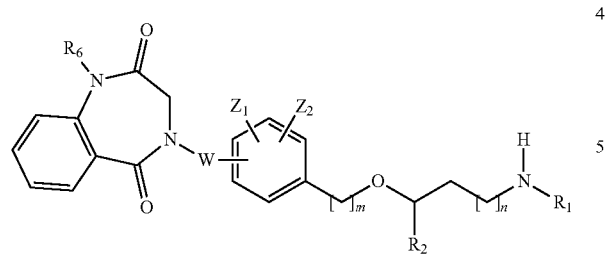
(I2b4)
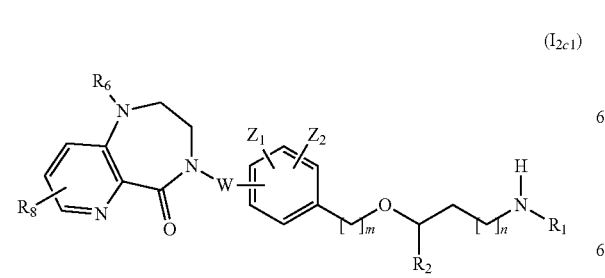
(I2c1)
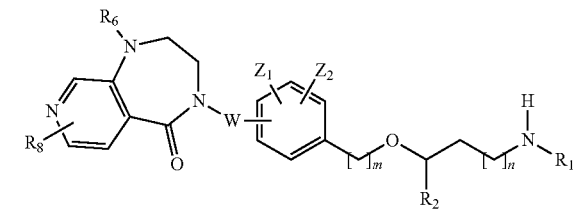
(I2c2)
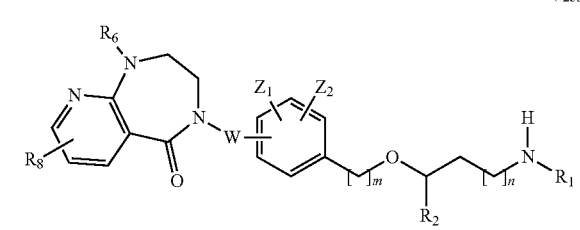
(I2c3)
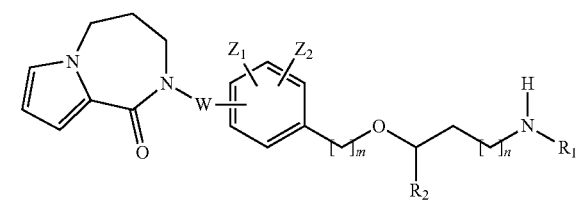
(I2d1)
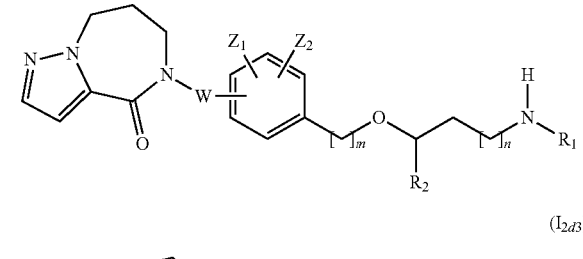
(I2d2)
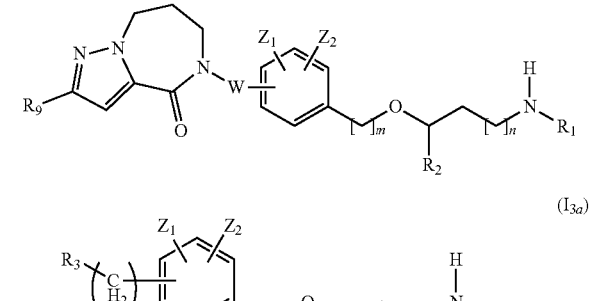
(I2d3)
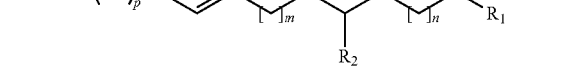
(I3a)
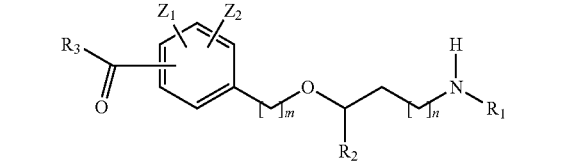
(I3b)

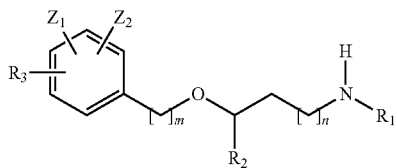

(I3c)

wherein $R_1$, $R_2$, $R_3$, $R_4$, $R_5$, $R_6$, $R_8$, $R_9$, W, $Z_1$, $Z_2$, n and m are as defined before and $R_{2a}$ is a hydrogen atom; a halogen atom; a branched or unbranched $C_{1-6}$-alkyl radical; a branched or unbranched $C_{1-6}$-alkoxy radical; a $C_{1-6}$-haloalcoxy radical or a $C_{1-6}$-haloalkyl radical, more preferably a hydrogen atom or a halogen atom, especially F;

or a pharmaceutically acceptable salt, isomer, prodrug or solvate thereof.

Another particularly preferred embodiment of the invention is represented by compounds of formula (I) having the above described subformulas ($I_{1a}$), ($I_{1b}$), ($I_{1c}$), ($I_{2a1}$), ($I_{2a2}$), ($I_{2a3}$), ($I_{2a4}$), ($I_{2b1}$), ($I_{2b2}$), ($I_{2b3}$), ($I_{2b4}$), ($I_{2c1}$), ($I_{2c2}$), ($I_{2c3}$), ($I_{2d1}$), ($I_{2d2}$), ($I_{3a}$), ($I_{3b}$) or ($I_{3c}$); wherein $R_1$, $R_2$, $R_3$, $R_4$, $R_5$, $R_6$, $R_8$, W, $Z_1$, $Z_2$, n and m are as defined before and $R_{2a}$ is a hydrogen atom; a halogen atom; a branched or unbranched $C_{1-6}$-alkyl radical; a branched or unbranched $C_{1-6}$-alkoxy radical; a $C_{1-6}$-haloalcoxy radical or a $C_{1-6}$-haloalkyl radical, more preferably a hydrogen atom or a halogen atom, especially F;

or a pharmaceutically acceptable salt, isomer, prodrug or solvate thereof.

The compounds of the present invention represented by the above described formula (I), ($I_{1a}$), ($I_{1b}$), ($I_{1c}$), ($I_{2a1}$), ($I_{2a2}$), ($I_{2a3}$), ($I_{2a4}$), ($I_{2b1}$), ($I_{2b2}$), ($I_{2b3}$), ($I_{2b4}$), ($I_{2c1}$), ($I_{2c2}$), ($I_{2c3}$), ($I_{2d1}$), ($I_{2d2}$), ($I_{2d3}$) ($I_{3a}$), ($I_{3b}$) or ($I_{3c}$) may include enantiomers depending on the presence of chiral centers or isomers depending on the presence of double bonds (e.g. Z, E). The single isomers, enantiomers or diastereoisomers and mixtures thereof fall within the scope of the present invention.

Among all the compounds described in the general formula (I), the following compounds are preferred for showing and intense inhibitory effect towards the α2δ-1 subunit of voltage-gated calcium channels (VGCC):

[1] N-methyl-3-(3-((1-methyl-1,2,3,5-tetrahydro-4H-benzo[e][1,4]diazepin-4-yl)methyl)phenoxy)-3-(thiophen-2-yl)propan-1-amine;
[2] (4-Methyl-1,4-diazepan-1-yl)(3-(3-(methylamino)-1-(thiophen-2-yl)propoxy)phenyl)methanone;
[3] (4-Methyl-1,4-diazepan-1-yl)(3-(3-(methylamino)-1-phenylpropoxy)phenyl)methanone;
[4] (1-Methyl-1,2,3,5-tetrahydro-4H-benzo[e][1,4]diazepin-4-yl)(3-(3-(methylamino)-1-(thiophen-2-yl)propoxy)phenyl)methanone;
[5] N-methyl-3-(3-(4-methyl-1,4-diazepan-1-yl)phenoxy)-3-phenylpropan-1-amine;
[6] N-methyl-3-((3-(4-methyl-1,4-diazepan-1-yl)benzyl)oxy)-3-phenylpropan-1-amine;
[7] N-methyl-3-((3-(1-methyl-1,2,3,5-tetrahydro-4H-benzo[e][1,4]diazepin-4-yl)benzyl)oxy)-3-phenylpropan-1-amine;
[8] N-methyl-3-(3-(4-methyl-1,4-diazepan-1-yl)phenoxy)-3-(thiophen-2-yl)propan-1-amine;
[9] N-methyl-3-(3-(1-methyl-1,2,3,5-tetrahydro-4H-benzo[e][1,4]diazepin-4-yl)phenoxy)-3-(thiophen-2-yl)propan-1-amine;
[10] N-methyl-3-((3-(4-methyl-1,4-diazepan-1-yl)benzyl)oxy)-3-(thiophen-2-yl)propan-1-amine;
[11] 2-(Ethylamino)-1-(4-(3-(3-(methylamino)-1-(thiophen-2-yl)propoxy)phenyl)-1,4-diazepan-1-yl)ethan-1-one;
[12] (S)—N-methyl-3-((3-(4-methyl-1,4-diazepan-1-yl)benzyl)oxy)-3-phenylpropan-1-amine;
[13] (R)—N-methyl-3-((3-(4-methyl-1,4-diazepan-1-yl)benzyl)oxy)-3-phenylpropan-1-amine;
[14] (R)-1-methyl-4-(3-((3-(methylamino)-1-(thiophen-2-yl)propoxy)methyl)phenyl)-1,2,3,4-tetrahydro-5H-benzo[e][1,4]diazepin-5-one;
[15] (S)-1-methyl-4-(3-((3-(methylamino)-1-(thiophen-2-yl)propoxy)methyl)phenyl)-1,2,3,4-tetrahydro-5H-benzo[e][1,4]diazepin-5-one;
[16] 1-(3-((3-(Methylamino)-1-(thiophen-2-yl)propoxy)methyl)phenyl)azepan-2-one;
[17] 1-(3-(3-(Methylamino)-1-(thiophen-2-yl)propoxy)phenyl)azepan-2-one;
[18] (R)-3-(ethylamino)-1-(3-((S)-3-(methylamino)-1-(thiophen-2-yl) propoxy)phenyl)azepan-2-one;
[19] (S)-3-(ethylamino)-1-(3-((S)-3-(methylamino)-1-(thiophen-2-yl)propoxy)phenyl)azepan-2-one;
[20] (R)-3-((ethylamino)methyl)-1-(3-((S)-3-(methylamino)-1-phenylpropoxy)phenyl)azepan-2-one;
[21] (S)-3-((ethylamino)methyl)-1-(3-((S)-3-(methylamino)-1-phenylpropoxy)phenyl)azepan-2-one;
[22] (R)-7-((ethylamino)methyl)-1-methyl-4-(3-((S)-3-(methylamino)-1-phenylpropoxy)phenyl)-1,4-diazepan-5-one;
[23] (S)-7-((ethylamino)methyl)-1-methyl-4-(3-((S)-3-(methylamino)-1-phenylpropoxy)phenyl)-1,4-diazepan-5-one;
[24] (S)-6-((ethylamino)methyl)-1-methyl-4-(3-((S)-3-(methylamino)-1-phenylpropoxy)phenyl)-1,4-diazepan-5-one;
[25] (R)-6-((ethylamino)methyl)-1-methyl-4-(3-((S)-3-(methylamino)-1-phenylpropoxy)phenyl)-1,4-diazepan-5-one;
[26] 1-Methyl-4-(3-((3-(methylamino)-1-phenylpropoxy)methyl)phenyl)-1,2,3,4-tetrahydro-5H-pyrido[3,2-e][1,4]diazepin-5-one;
[27] 8-Fluoro-1-methyl-4-(3-((3-(methylamino)-1-phenylpropoxy)methyl)phenyl)-1,2,3,4-tetrahydro-5H-pyrido[3,2-e][1,4]diazepin-5-one;
[28] 1-Methyl-4-(3-((3-(methylamino)-1-phenylpropoxy)methyl)phenyl)-1,2,3,4-tetrahydro-5H-pyrido[3,4-e][1,4]diazepin-5-one;
[29] 8-(Ethylamino)-1-methyl-4-(3-((3-(methylamino)-1-phenylpropoxy)methyl)phenyl)-1,2,3,4-tetrahydro-5H-pyrido[2,3-e][1,4]diazepin-5-one;
[30] (S)-5-(((S)-3-(methylamino)-1-phenylpropoxy)methyl)phenyl)-1,2,3,3a,4,5-hexahydro-6H-benzo[f]pyrrolo[1,2-a][1,4]diazepin-6-one;
[31] (S)-5-(((R)-3-(methylamino)-1-phenylpropoxy)methyl)phenyl)-1,2,3,3a,4,5-hexahydro-6H-benzo[f]pyrrolo[1,2-a][1,4]diazepin-6-one;
[32] 1-Methyl-4-(3-(3-(methylamino)-1-phenylpropoxy)phenyl)-1,4-diazepan-5-one,
[33] 1-(3-(3-(Methylamino)-1-phenylpropoxy)phenyl)azepan-2-one;
[34] 1-Methyl-4-(3-((3-(methylamino)-1-phenylpropoxy)methyl)phenyl)-1,4-diazepan-5-one;
[35] 1-(3-((3-(Methylamino)-1-phenylpropoxy)methyl)phenyl)azepan-2-one;
[36] 4-Methyl-1-(3-((3-(methylamino)-1-phenylpropoxy)methyl)phenyl)-1,4-diazepan-2-one;

[37] 4-(3-((3-(Methylamino-1-phenylpropoxy)methyl)phenyl)-1,4-diazepan-5-one;
[38] 1-Methyl-4-(3-((3-(methylamino)-1-phenylpropoxy)methyl)phenyl)-1,2,3,4-tetrahydro-5H-benzo[e][1,4]diazepin-5-one;
[39] 4-(3-((1-(2-Fluorophenyl)-3-(methylamino)propoxy)methyl)phenyl)-1-methyl-1,2,3,4-tetrahydro-5H-benzo[e][1,4]diazepin-5-one;
[40] 4-(3-((1-(3-Fluorophenyl)-3-(methylamino)propoxy)methy)phenyl)-1-methyl-1,2,3,4-tetrahydro-5H-benzo[e][1,4]diazepin-5-one;
[41] (R)-4-(3-((1-(3-fluorophenyl)-3-(methylamino)propoxy)methyl)phenyl)-1-methyl-1,2,3,4-tetrahydro-5H-benzo[e][1,4]diazepin-5-one;
[42] (S)-4-(3-((1-(3-fluorophenyl)-3-(methylamino)propoxy)methyl)phenyl)-1-methyl-1,2,3,4-tetrahydro-5H-benzo[e][1,4]diazepin-5-one;
[43] 4-(3-((3-(Ethylamino)-1-phenylpropoxy)methyl)phenyl)-1-methyl-1,2,3,4-tetrahydro-5H-benzo[e][1,4]diazepin-5-one;
[44] 4-(3-((3-((2-Fluoroethyl)amino)-1-phenylpropoxy)methyl)phenyl)-1-methyl-1,2,3,4-tetrahydro-5H-benzo[e][1,4]diazepin-5-one;
[45] 1-Methyl-4-(3-((3-(methylamino)-1-phenylpropoxy)methyl)phenyl)-1,2,3,4-tetrahydro-5H-pyrido[2,3-e][1,4]diazepin-5-one;
[46] 1-Methyl-4-(4-((3-(methylamino)-1-phenylpropoxy)methyl)phenyl)-1,2,3,4-tetrahydro-5H-benzo[e][1,4]diazepin-5-one;
[47] (R)-1-methyl-4-(3-((3-(methylamino)-1-phenylpropoxy)methyl)phenyl)-1,2,3,4-tetrahydro-5H-benzo[e][1,4]diazepin-5-one;
[48] 1,8-Dimethyl-4-(3-((3-(methylamino)-1-phenylpropoxy)methyl)phenyl)-1,2,3,4-tetrahydro-5H-pyrido[2,3-e][1,4]diazepin-5-one;
[49] (S)-1-methyl-4-(3-((3-(methylamino)-1-phenylpropoxy)methyl)phenyl)-1,2,3,4-tetrahydro-5H-benzo[e][1,4]diazepin-5-one;
[50] 1-Methyl-4-(3-(3-(methylamino)-1-(thiophen-2-yl)propoxy)phenyl)-1,4-diazepan-5-one;
[51] 1-Methyl-4-(3-(3-(methylamino)-1-(thiophen-2-yl)propoxy)phenyl)-3,4-dihydro-1H-benzo[e][1,4]diazepine-2,5-dione;
[52] 4-Methyl-1-(3-(3-(methylamino)-1-(thiophen-2-yl)propoxy)phenyl)-1,4-diazepan-2-one;
[53] 1-Methyl-4-(3-(3-(methylamino)-1-(thiophen-2-yl)propoxy)phenyl)-1,2,3,4-tetrahydro-5H-benzo[e][1,4]diazepin-5-one;
[54] (S)-8-(ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[55] (S)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[56] (R)-8-(ethylamino)-1-methyl-4-(3-(3-(methylamino)-1-(thiophen-2-yl)propoxy)phenyl)-1,2,3,4-tetrahydro-5H-pyrido[2,3-][1,4]diazepin-5-one;
[57] 1-Methyl-4-(3-(3-(methylamino)-1-(thiophen-2-yl)propoxy)phenyl)-1,2,3,4-tetrahydro-5H-pyrido[3,2-e][1,4]diazepin-5-one;
[58] 1-Ethyl-4-(3-(3-(methylamino)-1-(thiophen-2-yl)propoxy)phenyl)-1,4-diazepan-5-one;
[59] 4-(3-3-(Methylamino)-1-(thiophen-2-yl)propoxy)phenyl)-1,4-diazepan-5-one;
[60] 1-Isopropyl-4-(3-(3-(methylamino)-1-(thiophen-2-yl)propoxy)phenyl)-1,4-diazepan-5-one;
[60] 1-Isopropyl-4-(3-3-(methylamino)-1-(thiophen-2-yl)propoxy)phenyl)-1,4-diazepan-5-one;
[61] (S)-1-methyl-4-(3-(3-(methylamino)-1-(thiophen-2-yl)propoxy)phenyl)-1,4-diazepan-5-one;
[62] (R)-1-methyl-4-(3-(3-(methylamino)-1-(thiophen-2-yl)propoxy)phenyl)-1,4-diazepan-5-one;
[63] (R)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[64] (R)-1,8-dimethyl-4-(3-(3-(methylamino)-1-(thiophen-2-yl)propoxy)phenyl)-1,2,3,4-tetrahydro-5H-pyrido[2,3-e][1,4]diazepin-5-one;
[65] (S)-1,8-dimethyl-4-(3-(3-(methylamino)-1-(thiophen-2-yl)propoxy)phenyl)-1,2,3,4-tetrahydro-5H-pyrido[2,3-e][1,4]diazepin-5-one;
[66] (S)-1-isopropyl-4-(3-(3-(methylamino)-1-(thiophen-2-yl)propoxy)phenyl)-1,4-diazepan-5-one;
[67] (R)-1-isopropyl-4-(3-(3-(methylamino)-1-(thiophen-2-yl)propoxy)phenyl)-1,4-diazepan-5-one;
[68] 1-(Ethylglycyl)-4-(3-(3-(methylamino)-1-(thiophen-2-yl)propoxy)phenyl)-1,4-diazepan-5-one;
[69] 8-(Ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[70] 8-(Dimethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[71] 1-Methyl-4-(3-(3-(methylamino)-1-(thiophen-2-yl)propoxy)phenyl)-1,2,3,4-tetrahydro-5H-pyrido[2,3-e][1,4]diazepin-5-one;
[72] 1,8-Dimethyl-4-(3-(3-(methylamino)-1-(thiophen-2-yl)propoxy)phenyl)-1,2,3,4-tetrahydro-5H-pyrido[2,3-e][1,4]diazepin-5-one;
[73] 1-Methyl-4-(3-(3-(methylamino)-1-(thiophen-2-yl)propoxy)phenyl)-1,2,3,4-tetrahydro-5H-pyrido[3,4-e][1,4]diazepin-5-one;
[74] 8-Fluoro-1-methyl-4-(3-(3-(methylamino)-1-(thiophen-2-yl)propoxy)phenyl)-1,2,3,4-tetrahydro-5H-pyrido[3,2-e][1,4]diazepin-5-one;
[75] 1-Isopropyl-4-(3-(3-(methylamino)-1-(thiophen-3-yl)propoxy)phenyl)-1,4-diazepan-5-one;
[76] (R)-1-isopropyl-4-(3-(3-(methylamino)-1-(thiophen-3-yl)propoxy)phenyl)-1,4-diazepan-5-one;
[77] (S)-1-isopropyl-4-(3-(3-(methylamino)-1-(thiophen-3-yl)propoxy)phenyl)-1,4-diazepan-5-one;
[78] 1,8-Dimethyl-4-(3-(3-(methylamino)-1-(thiophen-3-yl)propoxy)phenyl)-1,2,3,4-tetrahydro-5H-pyrido[2,3-e][1,4]diazepin-5-one;
[79] (R)-1,8-dimethyl-4-(3-(3-(methylamino)-1-(thiophen-3-yl)propoxy)phenyl)-1,2,3,4-tetrahydro-5H-pyrido[2,3-e][1,4]diazepin-5-one;
[80] (S)-1,8-dimethyl-4-(3-(3-(methylamino)-1-(thiophen-3-yl)propoxy)phenyl)-1,2,3,4-tetrahydro-5H-pyrido[2,3-e][1,4]diazepin-5-one;
[81] (S)-1-methyl-4-(3-(3-(methylamino)-1-(thiophen-2-yl)propoxy)phenyl)-8-(trifluoromethyl)-1,2,3,4-tetrahydro-5H-pyrido[2,3-e][1,4]diazepin-5-one;
[82] (S)-8-methoxy-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[83] (S)-8-amino-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[84] 1-Methyl-4-(3-((3-(methylamino)-1-(thiophen-2-yl)propoxy)methyl)phenyl)-1,4-diazepan-5-one;

1-Methyl-4-(4-((2-(methylamino) 1-phenylethoxy)methy) phenyl)-1,2,3,4-tetrahydro-5H-benzo[e][1,4]diazepin-5-one;

[86] (R)-7-((ethylamino)methyl)-1-methyl-4-(3-((S)-3-(methylamino)-1-(thiophen-2-yl)propoxy)phenyl)-1,4-diazepan-5-one;

[87] (S)-7-((ethylamino)methyl)-1-methyl-4-(3-((S)-3-(methylamino)-1-(thiophen-2-yl)propoxy)phenyl)-1,4-diazepan-5-one;

[88] 1-Methyl-4-(4-((3-(methylamino)-1-phenylpropoxy) methyl)benzyl)-1,2,3,4-tetrahydro-5H-benzo[e][1,4]diazepin-5-one;

[89] 1-Methyl-4-(3-((3-(methylamino)-1-phenylpropoxy) methyl)benzyl)-1,2,3,4-tetrahydro-5H-benzo[e][1,4]diazepin-5-one;

[90] (S)-1-methyl-4-(4-(3-(methylamino)-1-(thiophen-2-yl) propoxy)benzyl)-1,2,3,4-tetrahydro-5H-pyrido[2,3-e][1, 4]diazepin-5-one;

[91] (S)-1,8-dimethyl-4-(4-(3-(methylamino-1-(thiophen-2-yl)propoxy)benzyl)-1,2,3,4-tetrahydro-5H-pyrido[2,3-e] [1,4]diazepin-5-one;

[92] (S)-8-(ethylamino)-1-methyl-4-(4-(3-(methylamino)-1-(thiophen-2-yl)propoxy)benzyl)-1,2,3,4-tetrahydro-5H-pyrido[2,3-e][1,4]diazepin-5-one;

[93] (S)-1-methyl-4-(4-(3-(methylamino)-1-(thiophen-2-yl) propoxy)benzyl)-8-(trifluoromethyl)-1,2,3,4-tetrahydro-5H-pyrido[2,3-e][1,4]diazepin-5-one;

[94] (S)-8-methoxy-1-methyl-4-(4-(3-(methylamino)-1-(thiophen-2-yl)propoxy)benzyl)-1,2,3,4-tetrahydro-5H-pyrido[2,3-e][1,4]diazepin-5-one;

[95] (S)-8-(dimethylamino)-1-methyl-4-(4-(3-(methylamino)-1-(thiophen-2-yl)propoxy)benzyl)-1,2,3,4-tetrahydro-5H-pyrido[2,3-e][1,4]diazepin-5-one;

[96] (S)-1-methyl-4-(4-(3-(methylamino)-1-(thiophen-2-yl) propoxy)benzyl)-1,2,3,4-tetrahydro-5H-pyrido[3,4-e][1, 4]diazepin-5-one;

[97] (S)-1-methyl-4-(4-(3-(methylamino)-1-(thiophen-2-yl) propoxy)benzyl)-1,2,3,4-tetrahydro-5H-pyrido[3,2-e][1, 4]diazepin-5-one;

[98] (S)-1-methyl-4-(4-(3-(methylamino)-1-(thiophen-2-yl) propoxy)benzyl)-1,2,3,4-tetrahydro-5H-benzo[e][1,4]diazepin-5-one;

[99] 1-Methyl-4-(4-(3-(methylamino)-1-(thiophen-2-yl) propoxy)benzyl)-1,2,3,4-tetrahydro-5H-pyrido[2,3-e][1, 4]diazepin-5-one;

[100] 1,8-Dimethyl-4-(4-(3-(methylamino)-1-(thiophen-2-yl)propoxy)benzyl)-1,2,3,4-tetrahydro-5H-pyrido[2,3-e] [1,4]diazepin-5-one;

[101] 1-Methyl-4-(4-(3-(methylamino)-1-(thiophen-2-yl) propoxy)benzyl)-1,4-diazepan-5-one;

[102] N-methyl-3-(4-((4-methyl-1,4-diazepan-1-yl)methyl) phenoxy)-3-(thiophen-2-yl)propan-1-amine;

[103] (S)-8-amino-1-methyl-4-(4-(3-(methylamino)-1-(thiophen-2-yl)propoxy)benzyl)-1,2,3,4-tetrahydro-5H-pyrido[2,3-e][1,4]diazepin-5-one;

[104] (S)-5-(4-(3-(methylamino)-1-(thiophen-2-yl)propoxy) benzyl)-5,6,7,8-tetrahydro-4H-pyrazolo[1,5-a][1,4]diazepin-4-one;

[105] (S)-2-(4-(3-(methylamino)-1-(thiophen-2-yl)propoxy) benzyl)-2,3,4,5-tetrahydro-1H-pyrrolo[1,2-a][1,4]diazepin-1-one;

[106] 1-Methyl-4-(3-(3-(methylamino)-1-(thiophen-2-yl) propoxy)benzyl)-1,2,3,4-tetrahydro-5H-benzo[e][1,4]diazepin-5-one;

[107] (S)-1-methyl-4-(2-methyl-4-(3-(methylamino)-1-(thiophen-2-yl)propoxy)benzyl)-1,2,3,4-tetrahydro-5H-pyrido[2,3-e][1,4]diazepin-5-one:

[108] (S)-4-(2-fluoro-4-(3-(methylamino)-1-(thiophen-2-yl) propoxy)benzyl)-1-methyl-1,2,3,4-tetrahydro-5H-pyrido [2,3-e][1,4]diazepin-5-one;

[109] 1-Methyl-4-(4-((2-(methylamino)-1-phenylethoxy) methyl)benzyl)-1,2,3,4-tetrahydro-5H-benzo[e][1,4]diazepin-5-one;

[110] 1,8-Dimethyl-4-(4-(3-(methylamino)-1-phenylpropoxy)benzyl)-1,2,3,4-tetrahydro-5H-pyrido[2,3-e][1, 4]diazepin-5-one;

[111] 8-(Ethylamino)-1-methyl-4-(4-(3-(methylamino)-1-phenylpropoxy)benzyl)-1,2,3,4-tetrahydro-5H-pyrido[2, 3-e][1,4]diazepin-5-one;

[112] 1-Methyl-4-(4-(3-(methylamino)-1-phenylpropoxy) benzyl)-1,2,3,4-tetrahydro-5H-benzo[e][1,4]diazepin-5-one;

[113] 1-Methyl-4-(3-(3-(methylamino)-1-phenylpropoxy) benzyl)-1,2,3,4-tetrahydro-5H-benzo[e][1,4]diazepin-5-one;

[114] (S)-1-methyl-4-(2-methyl-4-(3-(methylamino)-1-phenylpropoxy)benzyl)-1,2,3,4-tetrahydro-5H-pyrido[2,3-e] [1,4]diazepin-5-one;

[115] 4-(4-(1-(4-Fluorophenyl)-3-(methylamino)propoxy) benzyl)-1-methyl-1,2,3,4-tetrahydro-5H-pyrido[2,3-e][1, 4]diazepin-5-one;

[116] (S)-4-(2-fluoro-4-(3-(methylamino)-1-phenylpropoxy)benzyl)-1-methyl-1,2,3,4-tetrahydro-5H-pyrido [2,3-e][1,4]diazepin-5-one;

[117] 4-(4-(1-(3-Fluorophenyl)-3-(methylamino)propoxy) benzyl)-1-methyl-1,2,3,4-tetrahydro-5H-pyrido[2,3-e][1, 4]diazepin-5-one;

[118a] (R)-4-(ethylamino)-1-(3-((S)-3-(methylamino)-1-(thiophen-2-yl) propoxy)phenyl)azepan-2-one:

[118b] (S)-4-(ethylamino)-1-(3-((S)-3-(methylamino)-1-(thiophen-2-yl) propoxy)phenyl)azepan-2-one:

[119] 4-(2-Fluoro-5-(1-(3-fluorophenyl)-3-(methylamino) propoxy)phenyl)-1-methyl-1,2,3,4-tetrahydro-5H-pyrido [2,3-e][1,4]diazepin-5-one;

[120] (S)-4-(3-fluoro-5-(3-(methylamino)-1-(thiophen-2-yl) propoxy)phenyl)-1-methyl-1,2,3,4-tetrahydro-5H-pyrido [2,3-e][1,4]diazepin-5-one;

[121] 4-(3-Fluoro-5-(1-(3-fluorophenyl)-3-(methylamino) propoxy)phenyl)-1-methyl-1,2,3,4-tetrahydro-5H-pyrido [2,3-e][1,4]diazepin-5-one;

[122] 4-(2-Fluoro-4-(3-(methylamino)-1-(thiophen-2-yl) propoxy)benzyl)-1-methyl-1,4-diazepan-5-one;

[123] 4-(2-Fluoro-4-(1-(3-fluorophenyl)-3-(methylamino) propoxy)benzyl)-1-methyl-1,2,3,4-tetrahydro-5H-pyrido [2,3-e][1,4]diazepin-5-one;

[124] (S)-2-methyl-5-(2-methyl-4-(3-(methylamino)-1-(thiophen-2-yl)propoxy)benzyl)-5,6,7,8-tetrahydro-4H-pyrazolo[1,5-a][1,4]diazepin-4-one;

[126] (S)-7-fluoro-1-methyl-4-(2-methyl-4-(3-(methylamino)-1-(thiophen-2-yl)propoxy)benzyl)-1,2,3,4-tetrahydro-5H-pyrido[2,3-e][1,4]diazepin-5-one;

[126] (S)-4-(2-chloro-4-(3-(methylamino)-1-(thiophen-2-yl)propoxy)benzyl)-1-methyl-1,2,3,4-tetrahydro-5H-pyrido[2,3-e][1,4]diazepin-5-one;

[127] (S)-1-methyl-4-(4-(3-(methylamino)-1-(thiophen-2-yl)propoxy)-2-(trifluoromethyl)benzyl)-1,2,3,4-tetrahydro-5H-pyrido[2,3-e][1,4]diazepin-5-one;

[128] (S) 4-(2-cyclopropyl-4-(3-(methylamino)-1-(thiophen-2-yl)propoxy)benzyl)-1-methyl-1,2,3,4-tetrahydro-5H-pyrido[2,3-e][1,4]diazepin-5-one;

[129] 4-(2-Fluoro-4-(1-(2-fluorophenyl)-3-(methylamino) propoxy)benzyl)-1-methyl-1,2,3,4-tetrahydro-5H-pyrido [2,3-e][1,4]diazepin-5-one;

[130] (S)-1-methyl-4-(4-(3-(methylamino)-1-phenylpropoxy)-2-(trifluoromethyl)benzyl)-1,2,3,4-tetrahydro-5H-pyrido[2,3-e][1,4]diazepin-5-one;

[131] 8-Amino-4-(2-fluoro-4-(1 (3-fluorophenyl)-3-(methylamino)propoxy)benzyl)-1-methyl-1,2,3,4-tetrahydro-5H-pyrido[2,3-e][1,4]diazepin-5-one;

[132] (S)-4(2-fluoro-3(methylamino)-1-phenylpropoxy)benzyl)-8-methoxy-1-methyl-1,2,3,4-tetrahydro-5H-pyrido[2,3-e][1,4]diazepin-5-one;

[133] (S)-4-(2-cyclopropyl-4-(3-(methylamino)-1-phenylpropoxy)benzyl)-1-methyl-1,2,3,4-tetrahydro-5H-pyrido[2,3-e][1,4]diazepin-5-one;

[134] (S)-2-methoxy-5-(2-methyl-4-(3-(methylamino)-1-(thiophen-2-yl)propoxy)benzyl)-5,6,7,8-tetrahydro-4H-pyrazolo[1,5-a][1,4]diazepin-4-one;

[135] (R)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

[136] (S)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

[137] (S)-8-amino-4-(2-fluoro-4-(3-(methylamino)-1-phenylpropoxy)benzyl)-1-methyl-1,2,3,4-tetrahydro-5H-pyrido[2,3-e][1,4]diazepin-5-one;

[138] (S)-8-amino-4-(2-fluoro-4-(3-(methylamino)-1-phenylpropoxy)benzyl)-1-methyl-1,2,3,4-tetrahydro-5H-pyrido[2,3-e][1,4]diazepin-5-one;

[139] (S)-5-(2-fluoro-4-(3-(methylamino)-1-phenylpropoxy)benzyl)-2-methyl-5,6,7,8-tetrahydro-4H-pyrazolo[1,5-a][1,4]diazepin-4-one;

[140] (S)-4-(2-fluoro-4-(3-(methylamino)-1-phenylpropoxy)benzyl)-7-methoxy-1-methyl-1,2,3,4-tetrahydro-5H-pyrido[3,4-e][1,4]diazepin-5-one:

[141] (S)-4-(2-chloro-4-(3-(methylamino)-1-phenylpropoxy)benzyl)-1-methyl-1,2,3,4-tetrahydro-5H-pyrido[2,3-e][1,4]diazepin-5-one;

[142] (S)-4-(2-fluoro-4-(3-(methylamino)-1-phenylpropoxy)benzyl)-8-hydroxy-1-methyl-1,2,3,4-tetrahydro-5H-pyrido[2,3-e][1,4]diazepin-5-one;

[143] (S)-7-fluoro-4-(2-fluoro-4-(3-(methylamino)-1-phenylpropoxy)benzyl)-1-methyl-1,2,3,4-tetrahydro-5H-pyrido[2,3-e][1,4]diazepin-5-one;

[144] (S)-5-(2-fluoro-4-(3-(methylamino)-1-phenylpropoxy)benzyl)-2-methoxy-5,6,7,8-tetrahydro-4H-pyrazolo[1,5-a][1,4]diazepin-4-one;

[145] (S)-5-(2-fluoro-4-(3-(methylamino)-1-phenylpropoxy)benzyl)-5,6,7,8-tetrahydro-4H-pyrazolo[1,5-a][1,4]diazepin-4-one;

[146] (S)-4-(2-fluoro-4-(3-(methylamino)-1-phenylpropoxy)benzyl)-9-methoxy-1-methyl-1,2,3,4-tetrahydro-5H-pyrido[3,4-e][1,4]diazepin-5-one;

[147] (R)-8-(ethylamino)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

[148] (S)-8-(ethylamino)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

[149] (S)-4-(2-chloro-4-(1-(3-fluorophenyl)-3-(methylamino)propoxy)benzyl)-1-methyl-1,2,3,4-tetrahydro-5H-pyrido[2,3-e][1,4]diazepin-5-one;

[150] (R)-4-(4-(1-(3-fluorophenyl)-3-(methylamino)propoxy)benzyl)-1-methyl-1,2,3,4-tetrahydro-5H-pyrido[2,3-e][1,4]diazepin-5-one;

[151] (S)-4-(4-(1-(3-fluorophenyl)-3-(methylamino)propoxy)benzyl)-1-methyl-1,2,3,4-tetrahydro-5H-pyrido[2,3-e][1,4]diazepin-5-one;

[152] (S)-4-(2-fluoro-4-(1-(2-fluorophenyl)-3-(methylamino)propoxy)benzyl)-1-methyl-1,2,3,4-tetrahydro-5H-pyrido[2,3-e][1,4]diazepin-5-one and

[153] (S)-8-amino-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

or a pharmaceutically acceptable salt, prodrug or solvate thereof.

Among compounds of general formula (I) some subgroups of compounds have shown in addition a dual affinity towards the α2δ-1 subunit of voltage-gated calcium channels (VGCC) and the noradrenaline transporter (NET). These compounds having dual affinity represent the preferred embodiments of the invention and are represented among one of the following of formula (Ic), (Id), (Ie), (If), (Ig), (Ih), (Ii), (Ij), (Ik) or (Im):

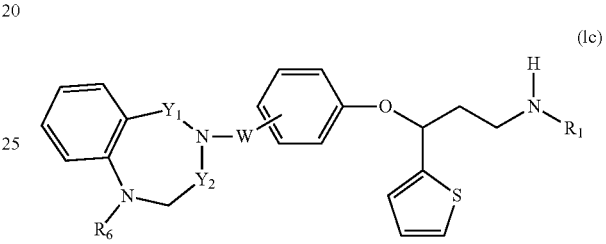
(Ic)

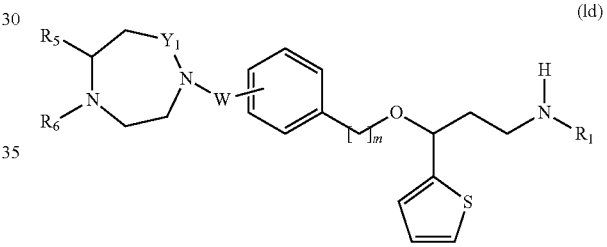
(Id)

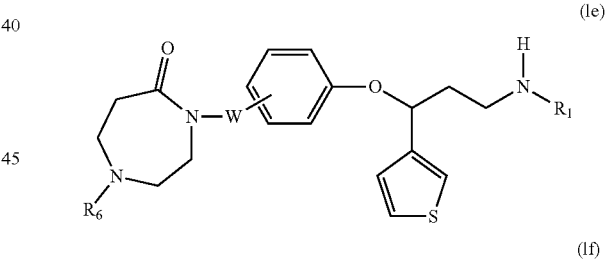
(Ie)

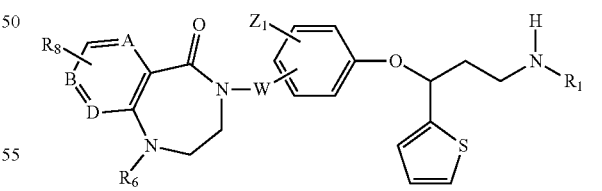
(If)

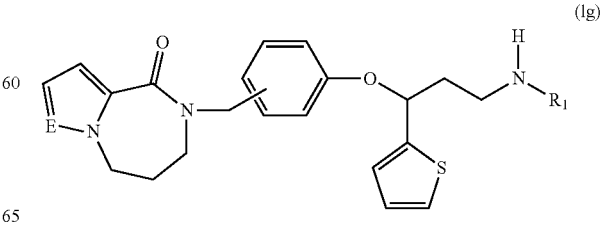
(Ig)

-continued

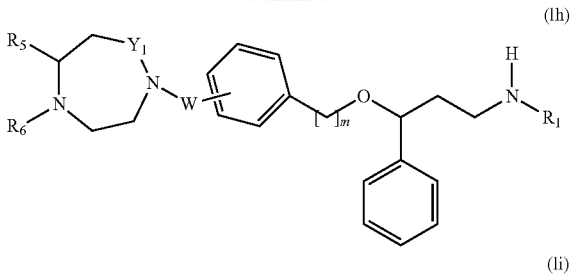
(Ih)

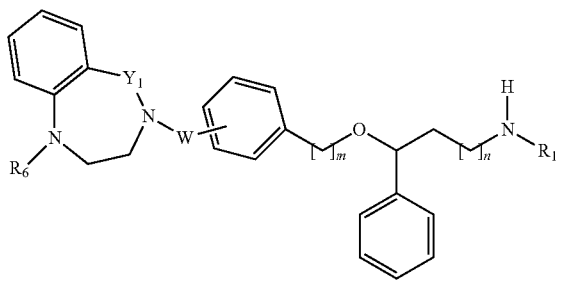
(Ii)

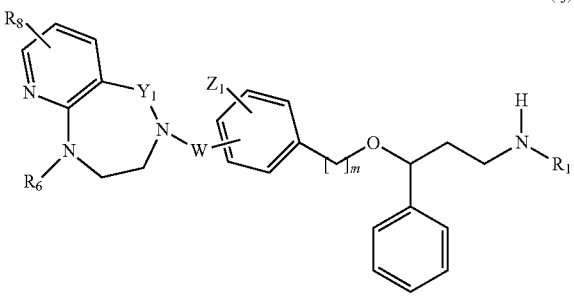
(Ij)

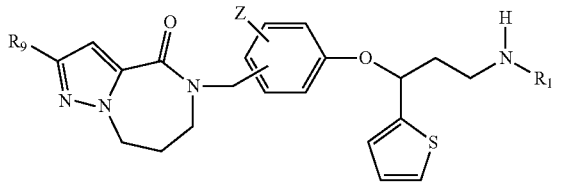
(Ik)

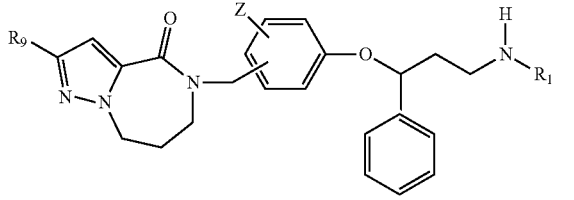
(Im)

wherein $R_1$, $R_5$, $R_6$, $R_8$, $R_9$, $Y_1$, $Y_2$, W, Z1, A, B, D, E n and m are as defined above.

The compounds having dual affinity towards the α2δ-1 subunit of voltage-gated calcium channels (VGCC) and the noradrenaline transporter (NET) which represent the preferred embodiments of the invention are preferably represented among one of the above described formulas (Ic), (Id), (Ie), (If), (Ig), (Ih), (Ii) or (Ij); wherein $R_1$, $R_5$, $R_6$, $R_8$, $Y_1$, $Y_2$, W, Z1, A, B, D, E n and m are as defined above.

The preferred compounds of the invention showing dual inhibitory effect towards the α2δ-1 subunit of voltage-gated calcium channels (VGCC) and the noradrenaline transporter (NET) are selected from the following group:

[1] N-methyl-3-(3-((1-methyl-1,2,3,5-tetrahydro-4H-benzo[e][1,4]diazepin-4-yl)methyl)phenoxy)-3-(thiophen-2-yl)propan-1-amine;
[3] (4-Methyl-1,4-diazepan-1-yl)(3-(3-(methylamino)-1-phenylpropoxy)phenyl)methanone;
[6] N-methyl-3-((3-(4-methyl-1,4-diazepan-1-yl)benzyl)oxy)-3-phenylpropan-1-amine;
[9] N-methyl-3-((3-(1-methyl-1,2,3,5-tetrahydro-4H-benzo[e][1,4]diazepin-4-yl)benzyl)oxy)-3-phenylpropan-1-amine;
[10] N-methyl-3-((3-(4-methyl-1,4-diazepan-1-yl)benzyl)oxy)-3-(thiophen-2-yl)propan-1-amine;
[29] 8-(Ethylamino)-1-methyl-4-(3-((3-(methylamino)-1-phenylpropoxy)methyl)phenyl)-1,2,3,4-tetrahydro-5H-pyrido[2,3-e][1,4]diazepin-5-one;
[34] 1-Methyl-4-(3-((3-(methylamino)-1-phenylpropoxy)methyl)phenyl)-1,4-diazepan-5-one;
[37] 4-(3-((3-(Methylamino)-1-phenylpropoxy)methyl)phenyl)-1,4-diazepan-5-one;
[50] 1-Methyl-4-(3-(3-(methylamino)-1-(thiophen-2-yl)propoxy)phenyl)-1,4-diazepan-5-one;
[54] (S)-8-(ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[55] (S)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[56] (R)-8-(ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[58] 1-Ethyl-4-(3-(3-(methylamino)-1-(thiophen-2-yl)propoxy)phenyl)-1,4-diazepan-5-one;
[60] 1-Isopropyl-4-(3-(3-(methylamino)-1-(thiophen-2-yl)propoxy)phenyl)-1,4-diazepan-5-one;
[61] (S)-1-methyl-4-(3-(3-(methylamino)-1-(thiophen-2-yl)propoxy)phenyl)-1,4-diazepan-5-one;
[65] (S)-1,8-dimethyl-4-(3-(3-(methylamino)-1-(thiophen-2-yl)propoxy)phenyl)-1,2,3,4-tetrahydro-5H-pyrido[2,3-e][1,4]diazepin-5-one;
[66] (S)-1-isopropyl-4-(3-(3-(methylamino)-1-(thiophen-2-yl)propoxy)phenyl)-1,4-diazepan-5-one;
[67] (R)-1-isopropyl-4-(3-(3-(methylamino)-1-(thiophen-2-yl)propoxy)phenyl-1,4-diazepan-5-one;
[69] 8-(Ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[70] 8-(Dimethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[71] 1-Methyl-4-(3-(3-(methylamino)-1-(thiophen-2-yl)propoxy)phenyl)-1,2,3,4-tetrahydro-5H-pyrido[2,3-e][1,4]diazepin-5-one;
[72] 1,8-Dimethyl-4-(3-(3-(methylamino)-1-(thiophen-2-yl)propoxy)phenyl)-1,2,3,4-tetrahydro-5H-pyrido[2,3-e][1,4]diazepin-5-one;
[75] 1-isopropyl-4-(3-(3-(methylamino)-1-(thiophen-3-yl)propoxy)phenyl)-1,4-diazepan-5-one;
[76] (R)-1-isopropyl-4-(3-(3-(methylamino)-1-(thiophen-3-yl)propoxy)phenyl)-1,4-diazepan-5-one;
[77] (S)-1-isopropyl-4-(3-(3-(methylamino)-1-(thiophen-3-yl)propoxy)phenyl)-1,4-diazepan-5-one;
[78] 1,8-Dimethyl-4-(3-(3-(methylamino)-1-(thiophen-3-yl)propoxy)phenyl)-1,2,3,4-tetrahydro-5H-pyrido[2,3-e][1,4]diazepin-5-one;
[80] (S)-1,8-dimethyl-4-(3-(3-(methylamino)-1-(thiophen-3-yl)propoxy)phenyl)-1,2,3,4-tetrahydro-5H-pyrido[2,3-e][1,4]diazepin-5-one;

[81] (S)-1-methyl-4-(3-(3-(methylamino)-1-(thiophen-2-yl)propoxy)phenyl)-8-(trifluoromethyl)-1,2,3,4-tetrahydro-5H-pyrido[2,3-e][1,4]diazepin-5-one;
[82] (S)-8-methoxy-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[83] (S)-8-amino-1-methyl-4-(3-(3-(methylamino)-1-(thiophen-2-yl)propoxy)phenyl)-1,2,3,4-tetrahydro-5H-pyrido[2,3-e][1,4]diazepin-5-one;
[84] 1-Methyl-4-(3-((3-(methylamino)-1-(thiophen-2-yl)propoxy)methyl)phenyl)-1,4-diazepan-5-one;
[86] (R)-7-((ethylamino)methyl)-1-methyl-4-(3-((S)-3-(methylamino)-1-(thiophen-2-yl)propoxy)phenyl)-1,4-diazepan-5-one;
[90] (S)-1-methyl-4-(4-(3-(methylamino)-1-(thiophen-2-yl)propoxy)benzyl)-1,2,3,4-tetrahydro-5H-pyrido[2,3-e][1,4]diazepin-5-one;
[91] (S)-1,8-dimethyl-4-(4-(3-(methylamino)-1-(thiophen-2-yl)propoxy)benzyl)-1,2,3,4-tetrahydro-5H-pyrido[2,3-e][1,4]diazepin-5-one;
[92] (S)-8-(ethylamino)-1-methyl-4-(4-(3-(methylamino)-1-(thiophen-2-yl)propoxy)benzyl)-1,2,3,4-tetrahydro-5H-pyrido[2,3-e][1,4]diazepin-5-one;
[93] (S)-1-methyl-4-(4-(3-(methylamino)-1-(thiophen-2-yl)propoxy)benzyl)-8-(trifluoromethyl)-1,2,3,4-tetrahydro-5H-pyrido[2,3-e][1,4]diazepin-5-one;
[94] (S)-8-methoxy-1-methyl-4-(4-(3-(methylamino)-1-(thiophen-2-yl)propoxy)benzyl)-1,2,3,4-tetrahydro-5H-pyrido[2,3-e][1,4]diazepin-5-one;
[96] (S)-1-methyl-4-(4-(3-(methylamino)-1-(thiophen-2-yl)propoxy)benzyl)-1,2,3,4-tetrahydro-5H-pyrido[3,4-e][1,4]diazepin-5-one;
[97] (S)-1-methyl-4-(4-(3-(methylamino)-1-(thiophen-2-yl)propoxy)benzyl)-1,2,3,4-tetrahydro-5H-pyrido[3,2-e][1,4]diazepin-5-one;
[98] (S)-1-methyl-4-(4-(3-(methylamino)-1-(thiophen-2-yl)propoxy)benzyl)-1,2,3,4-tetrahydro-5H-benzo[e][1,4]diazepin-5-one;
[99] 1-Methyl-4-(4-(3-(methylamino)-1-(thiophen-2-yl)propoxy)benzyl)-1,2,3,4-tetrahydro-5H-pyrido[2,3-e][1,4]diazepin-5-one;
[100] 1,8-Dimethyl-4-(4-(3-(methylamino)-1-(thiophen-2-yl)propoxy)benzyl)-1,2,3,4-tetrahydro-5H-pyrido[2,3-e][1,4]diazepin-5-one;
[103] (S)-8-amino-1-methyl-4-(4-(3-(methylamino)-1-(thiophen-2-yl)propoxy)benzyl)-1,2,3,4-tetrahydro-5H-pyrido[2,3-e][1,4]diazepin-5-one;
[104] (S)-5-(4-(3-(methylamino)-1-(thiophen-2-yl)propoxy)benzyl)-5,6,7,8-tetrahydro-4H-pyrazolo[1,5-a][1,4]diazepin-4-one;
[105] (S)-2-(4-(3-(methylamino)-1-(thiophen-2-yl)propoxy)benzyl)-2,3,4,5-tetrahydro-1H-pyrrolo[1,2-a][1,4]diazepin-1-one;
[108] (S)-4-(2-fluoro-4-(3-(methylamino)-1-(thiophen-2-yl)propoxy)benzyl)-1-methyl-1,2,3,4-tetrahydro-5H-pyrido[2,3-e][1,4]diazepin-5-one;
[110] 1,8-Dimethyl-4-(4-(3-(methylamino)-1-phenylpropoxy)benzyl)-1,2,3,4-tetrahydro-5H-pyrido[2,3-e][1,4]diazepin-5-one;
[111] 8-(Ethylamino)-1-methyl-4-(4-(3-(methylamino)-1-phenylpropoxy)benzyl)-1,2,3,4-tetrahydro-5H-pyrido[2,3-e][1,4]diazepin-5-one;
[114] (S)-1-methyl-4-(2-methyl-4-(3-(methylamino)-1-phenylpropoxy)benzyl)-1,2,3,4-tetrahydro-5H-pyrido[2,3-e][1,4]diazepin-5-one;
[115] 4-(4-(1-(4-Fluorophenyl)-3-(methylamino)propoxy)benzyl)-1-methyl-1,2,3,4-tetrahydro-5H-pyrido[2,3-e][1,4]diazepin-5-one;
[116] (S)-4-(2-fluoro-4-(3-(methylamino)-1-phenylpropoxy)benzyl)-1-methyl-1,2,3,4-tetrahydro-5H-pyrido[2,3-e][1,4]diazepin-5-one;
[117] 4-(4-(1-(3-Fluorophenyl)-3-(methylamino)propoxy)benzyl)-1-methyl-1,2,3,4-tetrahydro-5H-pyrido[2,3-e][1,4]diazepin-5-one;
[119] 4-(2-Fluoro-5-(1-(3-fluorophenyl)-3-(methylamino)propoxy)phenyl)-1-methyl-1,2,3,4-tetrahydro-5H-pyrido[2,3-e][1,4]diazepin-5-one;
[120] (S)-4-(3-fluoro-5-(3-(methylamino)-1-(thiophen-2-yl)propoxy)phenyl)-1-methyl-1,2,3,4-tetrahydro-5H-pyrido[2,3-e][1,4]diazepin-5-one;
[121] 4-(3-Fluoro-5-(1-(3-fluorophenyl)-3-(methylamino)propoxy)phenyl)-1-methyl-1,2,3,4-tetrahydro-5H-pyrido[2,3-e][1,4]diazepin-5-one;
[123] 4-(2-Fluoro-4-(1-(3-fluorophenyl)-3-(methylamino)propoxy)benzyl)-1-methyl-1,2,3,4-tetrahydro-5H-pyrido[2,3-e][1,4]diazepin-5-one;
[126] (S)-4-(2-chloro-4-(3-(methylamino)-1-(thiophen-2-yl)propoxy)benzyl)-1-methyl-1,2,3,4-tetrahydro-5H-pyrido[2,3-e][1,4]diazepin-5-one;
[129] 4-(2-Fluoro-4-(1-(2-fluorophenyl)-3-(methylamino)propoxy)benzyl)-1-methyl-1,2,3,4-tetrahydro-5H-pyrido[2,3-e][1,4]diazepin-5-one;
[131] 8-Amino-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;
[132] (S)-4-(2-fluoro-4-(3-(methylamino)-1-phenylpropoxy)benzyl)-8-methoxy-1-methyl-1,2,3,4-tetrahydro-5H-pyrido[2,3-e][1,4]diazepin-5-one;
[134] (S)-2-methoxy-5-(2-methyl-4-(3-(methylamino)-1-(thiophen-2-yl)propoxy)benzyl)-5,6,7,8-tetrahydro-4H-pyrazolo[1,5-a][1,4]diazepin-4-one;
[136] (S)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;
[137] (S)-8-amino-4-(2-fluoro-4-(3-(methylamino)-1-phenylpropoxy)benzyl)-1-methyl-1,2,3,4-tetrahydro-5H-pyrido[2,3-e][1,4]diazepin-5-one;
[138] (S)-8-amino-4-(2-fluoro-4-(3-(methylamino)-1-phenylpropoxy)benzyl)-1-methyl-1,2,3,4-tetrahydro-5H-pyrido[2,3-e][1,4]diazepin-5-one;
[139] (S)-5-(2-fluoro-4-(3-(methylamino)-1-phenylpropoxy)benzyl)-2-methyl-5,6,7,8-tetrahydro-4H-pyrazolo[1,5-a][1,4]diazepin-4-one;
[140] (S)-4-(2-fluoro-4-(3-(methylamino)-1-phenylpropoxy)benzyl)-7-methoxy-1-methyl-1,2,3,4-tetrahydro-5H-pyrido[3,4-e][1,4]diazepin-5-one;
[141] (S)-4-(2-chloro-4-(3-(methylamino)-1-phenylpropoxy)benzyl)-1-methyl-1,2,3,4-tetrahydro-5H-pyrido[2,3-e][1,4]diazepin-5-one;
[142] (S)-4-(2-fluoro-4-(3-(methylamino)-1-phenylpropoxy)benzyl)-8-hydroxy-1-methyl-1,2,3,4-tetrahydro-5H-pyrido[2,3-e][1,4]diazepin-5-one;
[143] (S)-7-fluoro-4-(2-fluoro-4-(3-(methylamino)-1-phenylpropoxy)benzyl)-1-methyl-1,2,3,4-tetrahydro-5H-pyrido[2,3-e][1,4]diazepin-5-one;
[144] (S)-5-(2-fluoro-4-(3-(methylamino)-1-phenylpropoxy)benzyl)-2-methoxy-5,6,7,8-tetrahydro-4H-pyrazolo[1,5-a][1,4]diazepin-4-one;
[145] (S)-5-(2-fluoro-4-(3-(methylamino)-1-phenylpropoxy)benzyl)-5,6,7,8-tetrahydro-4H-pyrazolo[1,5-a][1,4]diazepin-4-one;

[148] (S)-8-(ethylamino)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

[149] (S)-4-(2-chloro-4-(1-(3-fluorophenyl)-3-(methylamino)propoxy)benzyl)-1-methyl-1,2,3,4-tetrahydro-5H-pyrido[2,3-e][1,4]diazepin-5-one;

[150] (R)-4-(4-(1-(3-fluorophenyl)-3-(methylamino)propoxy)benzyl)-1-methyl-1,2,3,4-tetrahydro-5H-pyrido[2,3-e][1,4]diazepin-5-one;

[151] (S)-4-(4-(1-(3-fluorophenyl)-3-(methylamino)propoxy)benzyl)-1-methyl-1,2,3,4-tetrahydro-5H-pyrido[2,3-e][1,4]diazepin-5-one;

[152] (S)-4-(2-fluoro-4-(1-(2-fluorophenyl)-3-(methylamino)propoxy)benzyl)-1-methyl-1,2,3,4-tetrahydro-5H-pyrido[2,3-e][1,4]diazepin-5-one and

[153] (S)-8-amino-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

or a pharmaceutically acceptable salt, prodrug or solvate thereof.

In another aspect, the invention refers to the processes for obtaining the compounds of general formula (I). Several procedures have been developed for obtaining all the compounds of the invention. Some of them will be explained below in methods A, B and C.

The obtained reaction products may, if desired, be purified by conventional methods, such as crystallization and chromatography. Where the processes described below for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

Method A

Method A represents a first process for synthesizing compounds according to general formula (I). Method A allows the preparation of compounds of general formula (Ia) that is compounds of formula (I) where m is 0. There are described two methods for obtaining compounds of formula (Ia), namely method A1 and A2.

Method A1

A process is described for the preparation of a compound of general formula (Ia):

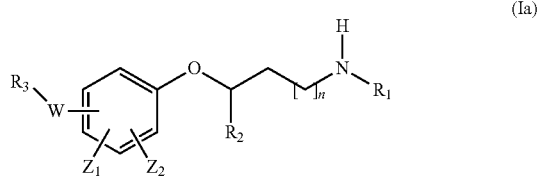
(Ia)

comprising:
the reaction of a compound of formula (IIa):

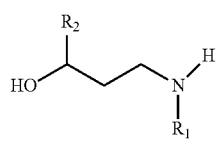
(IIa)

with a compound of formula (IIIa) or (IIIb):

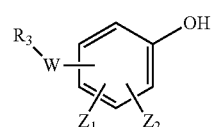
(IIIa)

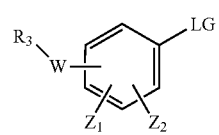
(IIIb)

wherein $R_1$, $R_2$, $R_3$, W, $Z_1$, $Z_2$ and n are as defined before and LG is a suitable leaving group such as chloro, bromo, iodo, mesylate, tosylate, nosylate or triflate.

In the case where the reaction is carried out between a compound of formula (IIa) with an hydroxyl compound of formula (IIIa), the reaction is performed under conventional Mitsunobu conditions by treating an alcohol of formula (IIa) with a compound of formula (IIa) in the presence of an azo compound such as, 1,1'-(azodicarbonyl)dipiperidine (ADDP), diisopropylazodicarboxylate (DIAD) or diethyl azodicarboxylate (DEAD) and a phosphine such as tributylphosphine or triphenylphoshine. The Mitsunobu reaction is carried out in a suitable solvent, such as toluene or tetrahydrofuran (THF); at a suitable temperature comprised between 0° C. and the reflux temperature, preferably at room temperature, or alternatively, the reactions can be carried out in a microwave reactor.

Whenever the reaction is carried out between a compound of formula (IIa) and a compound of formula (IIIb), the reaction is performed under conventional aromatic nucleophilic substitution conditions by treating an alcohol of formula (IIa) with a compound of formula (IIIb) wherein LG represents a leaving group (preferably fluoro), in the presence of a strong base such as sodium hydride. The reaction is preferably carried out in a suitable solvent, such as a polar aprotic solvent, preferably dimethylformamide (DMF) or dimethylacetamide; at a suitable temperature comprised between room temperature and the reflux temperature, preferably heating, or alternatively, the reactions can be carried out in a microwave reactor. Alternatively, when LG is triflate, bromo or iodo, the compound of formula (IIIb) can be introduced under cross-coupling conditions, using a Pd or Cu catalyst and a suitable ligand.

Compound of formula (IIa) is commercially available or can be obtained by reduction of the corresponding ketones, preferably using a hydride source. In addition, the reduction can be performed under asymmetric conditions described in the literature to render chiral compounds of formula (IIa) in enantiopure form. As a way of example, the chiral reduction can be performed using a hydride source such as borane-tetrahydrofuran complex or borane-dimethyl sulfide complex, in the presence of a Corey-Bakshi-Shibata oxazaborolidine catalyst, in a suitable solvent such as tetrahydrofuran or toluene, at a suitable temperature, preferably comprised between 0° C. and room temperature.

Alternatively compound of formula (IIa) can be obtained by deprotection of a compound of formula (IIa)-P (see scheme 1) protected with any suitable protecting group (P), such as for example Boc (tert-butoxycarbonyl) or Teoc (2-(trimethylsilyl)ethoxycarbonyl). Boc or Teoc deprotection can be effected by any suitable method, such as treatment with an acid, preferably HCl or trifluoroacetic acid in an appropriate solvent such as 1,4-dioxane, dichloromethane (DCM), ethyl acetate or a mixture of an organic solvent and water; alternatively by treatment with $ZnBr_2$ in an organic solvent, preferably DCM. Alternatively, for Teoc deprotection, by reaction with CsF in an organic solvent, preferably DMF at a temperature range of 20-130° C., alternatively under microwaves irradiation.

Also compound (IIa) can be obtained by incorporation of the amino group into a compound of formula (IIa)-LG by an alkylation reaction with compound (VI) (see scheme 1). The alkylation reaction is carried out in a suitable solvent, such as ethanol, dimethylformamide, dimethylsulfoxide (DMSO), acetonitrile (ACN) or a mixture of an organic solvent and water, preferably ethanol; optionally in the presence of a base such as $K_2CO_3$ or triethylamine (TEA); at a suitable temperature comprised between room temperature and the reflux temperature, preferably heating, or alternatively, the reactions can be carried out in a microwave reactor. Additionally, an activating agent such as sodium iodide or potassium iodide can be used.

Compounds of formula (IIIa), (IIIb) or (VI) are commercially available or can be prepared by conventional methods described in the bibliography.

Method A2

A further alternative process for the preparation of a compound of general formula (Ia) comprises the reaction of a compound of formula (IV-LG):

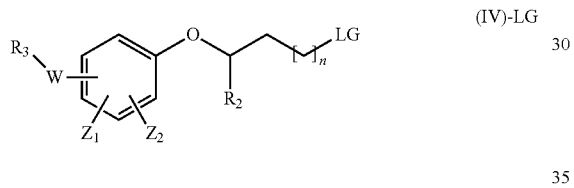

(IV)-LG with a compound of formula (VI):

(VI)

wherein $R_1$, $R_2$, $R_3$, W, $Z_1$, $Z_2$ and n are as defined before and LG represents a suitable leaving group such as chloro, bromo, iodo, mesylate, tosylate, nosylate or triflate.

The alkylation reaction is carried out in a suitable solvent, such as ethanol, dimethylformamide, dimethylsulfoxide, acetonitrile or a mixture of an organic solvent and water, preferably ethanol; optionally in the presence of a base such as $K_2CO_3$ or triethylamine; at a suitable temperature comprised between room temperature and the reflux temperature, preferably heating, or alternatively, the reactions can be carried out in a microwave reactor. Additionally, an activating agent such as sodium iodide or potassium iodide can be used.

Compound of formula (IV)-LG can be prepared by reaction of a compound of formula (IIb)-LG where LG represents a leaving group (such as chloro, bromo, iodo, mesylate, tosylate, nosylate or triflate) with a compound of formula (IIIa) (see scheme 1). The reaction is carried out preferably in the presence of a base, such as sodium hydride. The alkylation reaction is carried out in a suitable solvent, such as tetrahydrofuran or dimethylformamide, at a suitable temperature comprised between 0° C. and the reflux temperature, preferably at room temperature.

Method B

Method B represents a process for synthesizing compounds according to general formula (Ib), namely compounds of general formula (I) where m is 1. There are described two methods for obtaining compounds of formula (Ib), namely method B1 and B2.

Method B1

A first process is described preparation of a compound of general formula (Ib):

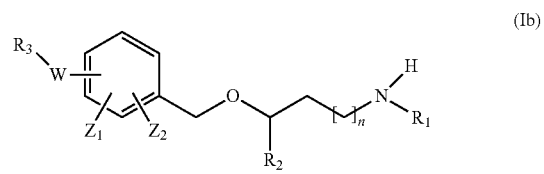

(Ib)

comprising:
a) the reaction between a compound of formula (IIa):

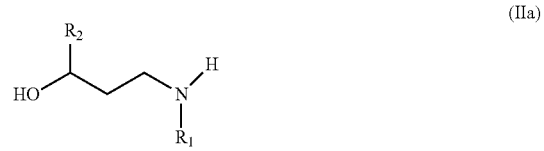

(IIa)

with a compound of formula (IIIc):

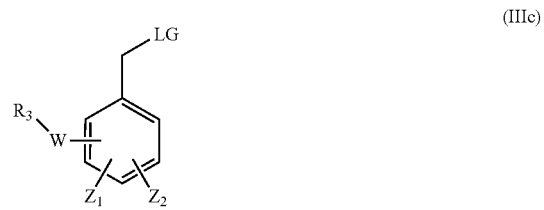

(IIIc)

wherein $R_1$, $R_2$, $R_3$, W, $Z_1$, $Z_2$ and n are as defined before and LG represents a suitable leaving group such as chloro, bromo, iodo, mesylate, tosylate, nosylate or triflate.

The reaction between the compound of formula (IIa) with an alkylating agent of formula (II Ic) is carried out in the presence of a strong base such as sodium hydride or potassium tert-butoxide. The alkylation reaction is preferably carried out in a suitable solvent, such as tetrahydrofuran or dimethylformamide, at a suitable temperature comprised between 0° C. and the reflux temperature, preferably room temperature, or alternatively, the reactions can be carried out in a microwave reactor. Additionally, an activating agent such as sodium iodide or a phase transfer catalyst such as tetrabutylammonium iodide can be used.

Method B2

The second method for preparing compounds of formula (Ib) comprises the deprotection of a compound of formula (V)—P:

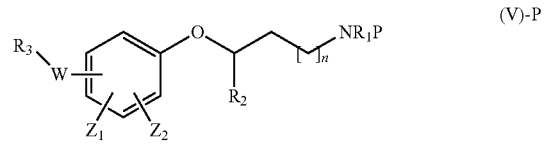

(V)-P wherein $R_1$, $R_2$, $R_3$, W, $Z_1$, $Z_2$ and n are as defined before and P represents a protecting group such as, for example, Boc (tert-butoxycarbonyl) or Teoc (2-(trimethylsilyl) ethoxycarbonyl).

Boc or Teoc deprotection can be effected by any suitable method, such as treatment with an acid, preferably HCl or trifluoroacetic acid in an appropriate solvent such as 1,4-dioxane, DCM, ethyl acetate or a mixture of an organic solvent and water; alternatively by treatment with $ZnBr_2$ in an organic solvent, preferably DCM. Alternatively, for Teoc deprotection, by reaction with CsF in an organic solvent, preferably DMF at a temperature range of 20-130° C., alternatively under microwaves irradiation.

Scheme 1 below summarizes the synthetic routes of methods A (including A1 and A2) and B (including B1 and B2).

starting from a compound of formula (VII):

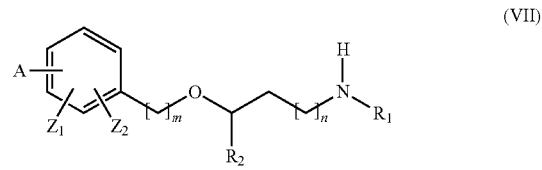

(VII)

Scheme 1

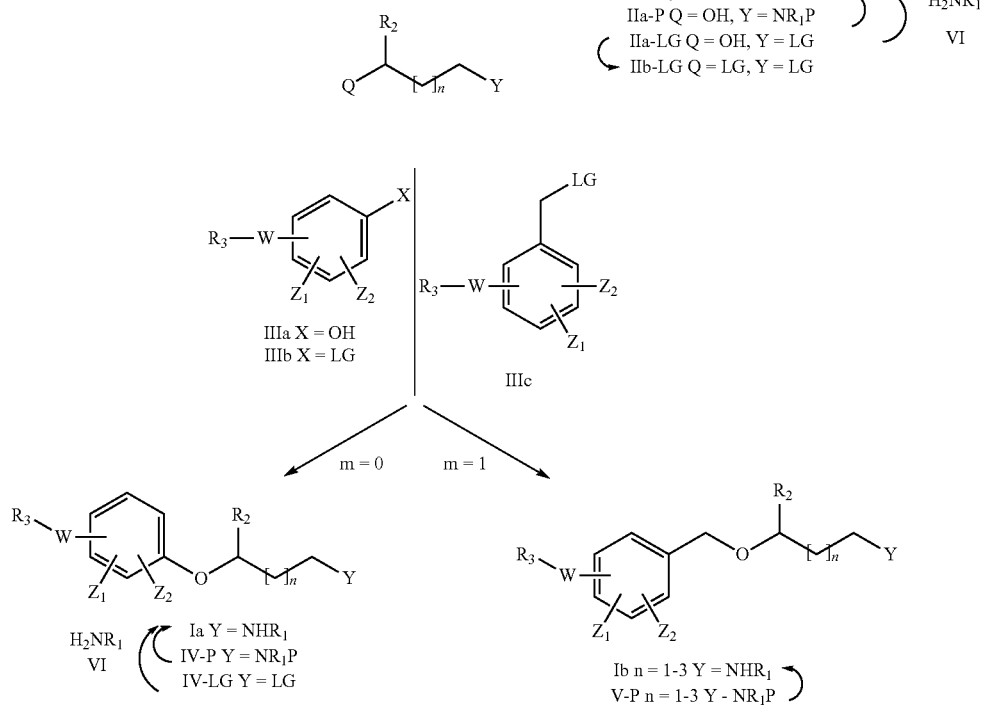

Method C

Method C represents the third process for synthesizing compounds according to general formula (I).

In this sense, there is provided a process for the preparation of a compound of general formula (I):

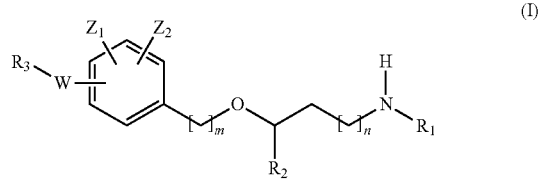

(I)

wherein $R_1$, $R_2$, $R_3$, W, $Z_1$, $Z_2$, m and n are as defined before and where A may represent an aldehyde, a carboxylic acid, a suitable leaving group or a —$(CH_2)_p$-LG group wherein LG represents a suitable leaving group and p is 1 or 2 and where the reaction is dependent on the nature of A and W resulting in that the reaction comprises:

- a reductive amination reaction in the presence of a reductive agent, when A is an aldehyde and W is —$(CH_2)_p$—;
- the reaction in the presence of a carboxylic acid activating reagent, when A is a carboxylic acid and W is a —C(O)— group;
- a coupling reaction in the presence of a metal catalyst, when A is a good leaving group and W is a bond; or
- a reaction in the presence of a base, when A is —$(CH_2)_p$-LG group and W is a —$(CH_2)_p$— group.

As explained above, the reaction of an intermediate of general formula (VII) or its counterparts (VII)-P and (VII)-LG (see scheme 2 below) to give a compound of formula (I) (or its counterparts (IV/V)-P and (IV/V)-LG, respectively) may be carried out under different reaction conditions, depending on the nature of the groups A and $R_3$—W:

When A is an aldehyde and W is —(CH$_2$)$_p$—, by reductive amination reaction in the presence of a reductive reagent, preferably sodium triacetoxyborohydride, in the presence of a base, preferably diisopropylethylamine (DIPEA) or triethylamine (TEA), in an organic solvent, preferably 1,2-dichloroethane (DCE).

When A is a carboxylic acid and W is —C(O)—, in the presence of a carboxylic acid activating reagent, preferably HATU (2-(7-Aza-1H-benzotriazole-1-yl)-1,1,3,3-tetramethyluronium) or EDCl (N-(3-Dimethylaminopropyl)-N'-ethylcarbodiimide hydrochloride), in the presence of a base, preferably DIPEA (N,N-Diisopropylethylamine) or TEA, in an organic solvent, preferably dichloromethane (DCM). Alternatively, by conversion to the acid chloride intermediate using any suitable method.

When A is a good leaving group as a halogen atom and W is a bond, using a metal catalyzed coupling, for example, in the presence of a copper salt as catalyst, preferably CuI, an appropriate ligand, preferably N1,N2-dimethylethane-1,2-diamine or proline, and an inorganic base, preferably K$_3$PO$_4$ or K$_2$CO$_3$ in an organic solvent, preferably 1,4-dioxane, N,N-dimethylformamide (DMF) or DMSO, at a temperature range of 80-130° C. Alternatively, in the presence of copper powder, in a polar solvent, preferably water, at a temperature range 80° C. and the reflux temperature. Alternatively, in the presence of a Pd catalyst, preferably Pd$_2$(dba)$_3$ and a suitable ligand, preferably 2-dicyclohexylphosphino-2',4',6'-triisopropylbiphenyl (Xphos), in the presence of a base, preferably NaOtBu, in an organic solvent, preferably toluene or 1,4-dioxane, at a temperature range of 50-150° C.

When A is a —(CH$_2$)$_p$-LG group (where LG is a good leaving group as a halogen atom or sulfonate), and W is —(CH$_2$)$_p$—, the reaction may be carried out in the presence of a base, preferably NaH, DIPEA or TEA, in an organic solvent, preferably DMF or THF, at a suitable temperature, preferably in the range of 0-100° C. Alternatively, in the presence of tetrabutylammonium iodide (TBAI).

The different synthetic routes including method C as well as reactions for preparing the intermediate compounds for such reactions are depicted in scheme 2:

In scheme 2, R$_1$, R$_2$, R$_3$, W, Z$_1$, Z$_2$, m and n are as defined before for compounds of formula (I), LG represents a leaving group (such as chloro, bromo, iodo, mesylate, tosylate, nosylate or triflate), P represents a protecting group of the amino function, such as Boc (tert-butoxycarbonyl) or Teoc (2-(trimethylsilyl)ethoxycarbonyl) and A represents a suitable function to be converted to a group R$_3$—W—.

Intermediates of type (VII) can be obtained from compounds of formula (IIa) or (IIb) and reagents of formula (VIIIa), (VIIIb) or (VIIIc) using the same reaction conditions as described above in methods A and B.

In turn, intermediates of formula (IIa), (IIa)-P and (IIa)-LG are commercially available or can be obtained by reduction of the corresponding ketones, preferably using a hydride source. In addition, the reduction can be performed under asymmetric conditions described in the literature to render chiral compounds of formula (IIa) in enantiopure form. As a way of example, the chiral reduction can be performed using a hydride source such as borane-tetrahydrofuran complex or borane-dimethyl sulfide complex, in the presence of a Corey-Bakshi-Shibata oxazaborolidine catalyst, in a suitable solvent such as tetrahydrofuran or toluene, at a suitable temperature, preferably comprised between 0° C. and room temperature.

The compounds of general formula (IIb)-LG are commercially available or can be obtained from compounds of formula (IIa)-LG by conventional methods described in the bibliography. For example, using methanesulfonyl chloride in an organic solvent, preferably DCM, in the presence of a base, preferably TEA or DIPEA, at a temperature range of 00° C. and room temperature.

The compounds of general formula (VI), (VIIIa), (VIIIb) and (VIIIc) are commercially available or can be prepared by conventional methods described in the bibliography.

Moreover, certain compounds of the present invention can also be obtained starting from other compounds of formula (I) by appropriate conversion reactions of functional groups, in one or several steps, using well-known reactions in organic chemistry under standard experimental conditions.

In addition, a compound of formula (I) that shows chirality can also be obtained by resolution of a racemic compound of formula (I) either by chiral preparative HPLC

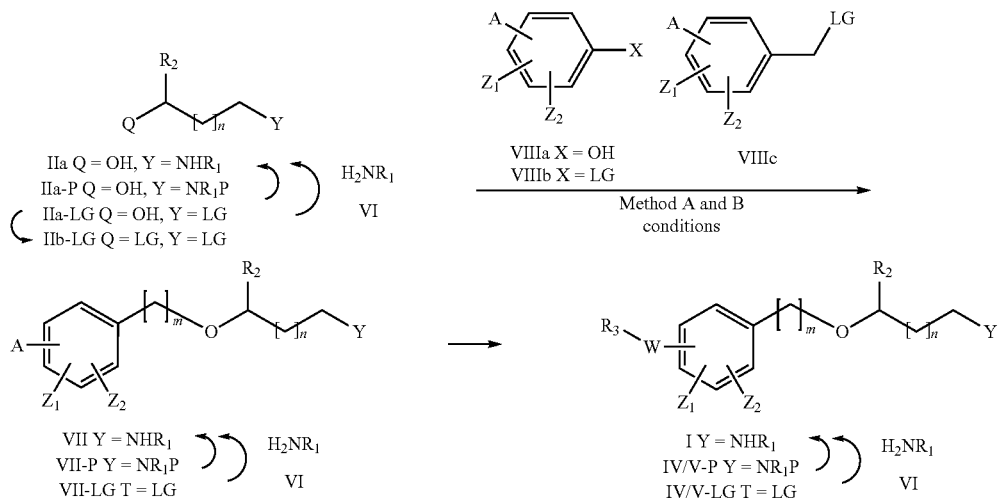

Scheme 2 or by crystallization of a diastereomeric salt or co-crystal. Alternatively, the resolution step can be carried out at a previous stage, using any suitable intermediate.

Turning to another aspect, the invention also relates to the therapeutic use of the compounds of general formula (I). As mentioned above, compounds of general formula (I) show a strong affinity to the subunit α2δ and more preferably to the α2δ-1 subunit of voltage-gated calcium channels. In a more preferred embodiment of the invention compounds of general formula (I) show a strong affinity both to the subunit α2δ and more preferably to the α2δ-1 subunit of voltage-gated calcium channels as well as to the noradrenaline transporter (NET) and can behave as agonists, antagonists, inverse agonists, partial antagonists or partial agonists thereof. Therefore, compounds of general formula (I) are useful as medicaments.

They are suitable for the treatment and/or prophylaxis of diseases and/or disorders mediated by the subunit α2δ, especially the α2δ-1 subunit of voltage-gated calcium channels and/or the noradrenaline transporter (NET). In this sense, compounds of formula (I) are suitable for the treatment and/or prophylaxis of pain, especially neuropathic pain, inflammatory pain, and chronic pain or other pain conditions involving allodynia and/or hyperalgesia, depression, anxiety and attention-deficit-/hyperactivity disorder (ADHD).

The compounds of formula (I) are especially suited for the treatment of pain, from medium to severe pain, visceral pain, chronic pain, cancer pain, migraine, inflammatory pain, acute pain or neuropathic pain, allodynia or hyperalgesia. This may include mechanical allodynia or thermal hyperalgesia.

PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and/or prophylaxis of allodynia and more specifically mechanical or thermal allodynia.

In another preferred embodiment compounds of the invention are used for the treatment and/or prophylaxis of hyperalgesia.

In yet another preferred embodiment compounds of the invention are used for the treatment and/or prophylaxis of neuropathic pain and more specifically for the treatment and/or prophylaxis of hyperpathia.

A related aspect of the invention refers to the use of compounds of formula (I) for the manufacture of a medicament for the treatment and/or prophylaxis of disorders and diseases mediated by the subunit α2δ, especially the α2δ-1 subunit of voltage-gated 30 calcium channels and/or the noradrenaline transporter (NET), as explained before.

Another related aspect of the invention refers to a method for the treatment and/or prophylaxis of disorders and diseases mediated by the subunit α2δ, especially the α2δ-1 subunit of voltage-gated calcium channels and/or the noradrenaline transporter (NET), as explained before comprising the administration of a therapeutically effective amount of a compound of general formula (I) to a subject in need thereof.

Another aspect of the invention is a pharmaceutical composition, which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the subunit α2δ, especially the α2δ-1 subunit of voltage-gated calcium channels and/or the noradrenaline transporter (NET) and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenteral, for example pulmonary, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, dragées, capsules, pills, chewing gums, powders, drops, gels, juices, syrups, solutions and suspensions. The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

In a preferred embodiment, the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the British and US Pharmacopoeias and similar reference texts.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The following examples are merely illustrative of certain embodiments of the invention and cannot be considered as restricting it in any way.

Examples

In the next preparation examples, the preparation of both intermediates compounds as well as compounds according to the invention is disclosed.

The following abbreviations are used:
ACN: Acetonitrile
Anh: Anhydrous
Aq: Aqueous
Conc: Concentration
CH: Cyclohexane
DCM: Dichloromethane
DCE: 1,2-Dichloroethane
DEA: Diethylamine
DIAD: Diisopropyl azodicarboxylate
DIBAL: Diisobutylaluminium hydride
DIPEA: N,N-Diisopropylethylamine
DMA: N,N-Dimethylacetamide
DMSO: Dimethylsulfoxide
EtOAc: Ethyl acetate
EtOH: Ethanol
Ex: Example
h: Hour/s
HATU: 2-(7-Aza-1H-benzotriazole-1-yl)-1,1,3,3-tetramethyluronium hexafluorophosphate
Hex: Hexane
HPLC: High-performance liquid chromatography
INT: Intermediate
IPA: Isopropanol
MeOH: Methanol
MS: Mass spectrometry
Min: Minutes
PPh$_3$: Triphenylphosphine
Quant: Quantitative
Ret: Retention
rt: Room temperature
Sat: Saturated
TBAF: Tetrabutylammonium fluoride
TBAI: Tetrabutylammonium iodide
TEA: Triethylamine
TFA: Trifluoroacetic acid
THF: Tetrahydrofuran
XPhos: 2-Dicyclohexylphosphino-2',4',6'-triisopropylbiphenyl
Wt: Weight The following methods were used to generate the HPLC or HPLC-MS data:

Method A: Column Eclipse XDB-C18 4.6×150 mm, 5 μm; flow rate 1 mL/min; A: H$_2$O (0.05% TFA); B: ACN; Gradient: 5% to 95% B in 7 min, isocratic 95% B 5 min.

Method B: Column Zorbax SB-C18 2.1×50 mm, 1.8 μm; flow rate 0.5 mL/min; A: H$_2$O (0.1% formic acid); B: ACN (0.1% formic acid); Gradient: 5% to 95% B in 4 min, isocratic 95% B 4 min.

Synthesis of Intermediates

INT 1: 1-Ethyl-1,4-diazepan-5-one

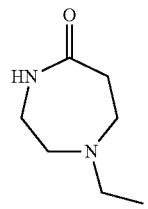

To a suspension of 1,4-diazepan-5-one trifluoroacetic acid salt (330 mg, 1.44 mmol), K$_2$CO$_3$ (800 mg, 5.79 mmol) in ACN (15 mL), iodoethane (250 mg, 1.60 mmol) was added and the mixture was heated at 55° C. for 14 h. The reaction mixture was cooled at rt and filtered. The filtrate was concentrated under vacuum, the residue was triturated with DCM and the solid was filtered to afford the title compound (132 mg, 64% yield) that was used in the next step without further purification. $^1$H-NMR (300 MHz, CDCl$_3$), δ ppm: 7.53 (bs, 1H), 3.17 (m, 2H), 2.49 (m, 4H), 2.46 (m, 2H), 2.41 (q. J=7 Hz, 2H), 0.94 (t, J=7 Hz, 3H).

INT 2: 1-Isopropyl-1,4-diazepan-5-one

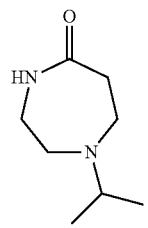

The compound was prepared in the conditions used in INT 1 using 2-iodopropane (60% yield). $^1$H-NMR (300 MHz, CDCl$_3$), δ ppm: 6.57 (bs, 1H), 3.28 (m, 2H), 2.91 (sept, J=6.7 Hz, 1H), 2.63 (m, 6H), 1.01 (d, J=6.7 Hz, 6H).

INT 3: 1-Methyl-1,2,3,4-tetrahydro-5H-benzo[e][1,4]diazepin-5-one

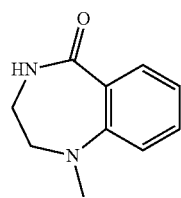

To a suspension of 1,2,3,4-tetrahydro-5H-benzo[e][1,4]diazepin-5-one (410 mg, 2.53 mmol) in DCE (20 mL), DIPEA (653 mg, 5.06 mmol), paraformaldehyde (296 mg, 9.35 mmol), NaBH(OAc)$_3$ (1.98 g, 9.35 mmol) and acetic acid (152 mg, 2.53 mmol) were added and the reaction mixture was stirred at rt for 48 h. NaHCO$_3$ sat solution was added and extracted with DCM. The organic layer was dried over Na$_2$SO$_4$, filtered and the solvent was removed under vacuum. The residue was tritured with diethylether and the solid was filtered and washed with diethylether to afford the title compound (410 mg, 92% yield) that was used in the next step without further purification.

$^1$H-NMR (500 MHz, CDCl$_3$), δ ppm: 8.37 (bs, 1H), 7.67 (m, 1H), 7.38 (m, 1H), 6.98 (m, 1H), 6.89 (m, 1H), 3.36 (m, 2H), 3.30 (m, 2H), 2.84 (s, 3H).

INT 4: 1-Methyl-1,2,3,4-tetrahydro-5H-pyrido[3,2-e][1,4]diazepin-5-one

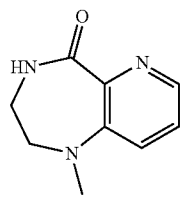

To a solution of ethyl 3-fluoropicolinate (190 mg, 1.12 mmol) in DMA (2.2 mL), K$_2$CO$_3$ (310 mg, 2.24 mmol) and N1-methylethane-1,2-diamine (83 mg, 1.12 mmol) were added and the mixture was heated at 150° C. in a sealed tube for 64 h. The reaction mixture was cooled at rt and concentrated under vacuum. Purification by flash chromatography, silica gel, gradient DCM to 20% MeOH afforded to title compound (56 g, 28% yield).

$^1$H-NMR (500 MHz, CDCl$_3$), δ ppm: 8.33 (m, 1H), 7.98 (bs, 1H), 7.32 (m, 1H), 7.27 (m, 1H), 3.45 (m, 2H), 3.37 (m, 2H), 2.89 (s, 3H).

INT 5: 8-Fluoro-1-methyl-1,2,3,4-tetrahydro-5H-pyrido[3,2-e][1,4]diazepin-5-one

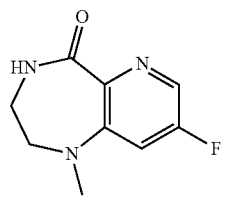

Methyl 3,5-difluoropicolinate was treated in the conditions used in INT 4 to afford the title compound (27% yield).

$^1$H-NMR (300 MHz, CDCl$_3$), δ ppm: 8.62 (bs, 1H), 8.13 (m, 1H), 6.93 (m, 1H), 3.45 (m, 4H), 3.00 (s, 3H).

INT 6: 1-Methyl-1,2,3,4-tetrahydro-5H-pyrido[3,4-e][1,4]diazepin-5-one

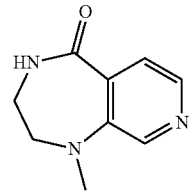

Methyl 3-fluoroisonicotinate was treated in the conditions used in INT 4 to afford the title compound (24% yield).

$^1$H-NMR (500 MHz, CDCl$_3$), δ ppm: 8.29 (s, 1H), 8.21 (m, 1H), 7.80 (bs, 1H), 7.54 (m, 1H), 3.43 (m, 4H), 2.99 (s, 3H).

INT 7: (S)-1,2,3,3a,4,5-hexahydro-6H-benzo[f]pyrrolo[1,2-a][1,4]diazepin-6-one

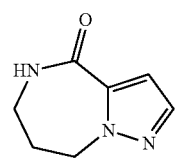 [SMILES: O=C1NCCCn2nccc21]

Methyl 2-fluorobenzoate was treated with (S)-pyrrolidin-2-ylmethanamine in the conditions used in INT 4 to afford the title compound (25% yield).

$^1$H-NMR (300 MHz, CDCl$_3$), δ ppm: 8.36 (bs, 1H), 8.06 (m, 1H), 7.30 (m, 1H), 6.71 (m, 1H), 6.60 (m, 1H), 3.75 (m, 1H), 3.35 (m, 4H), 2.09 (m, 2H), 1.74 (m, 2H).

INT 8: 5,6,7,8-Tetrahydro-4H-pyrazolo[1,5-a][1,4]diazepin-4-one

To a solution of methyl 1H-pyrazole-5-carboxylate (350 mg, 2.78 mmol) and 3-bromopropan-1-amine hydrobromide (1.0 g, 4.58 mol) in a mixture of ACN:THF (1:6, 7 mL), 1,8-diazabicyclo[5.4.0]undec-7-ene (2.11 g, 13.88 mmol) was added and the reaction mixture was stirred at rt for 18 h. The reaction mixture was cooled at 0° C. and NaCl (1.0 g), water (4.5 mL) and H$_3$PO$_4$ (85% w/w, 0.3 mL) were added and the mixture was stirred for 30 min. The organic solvent was removed under vacuum and the residue was extracted with DCM. Purification by flash chromatography, silica gel, gradient CH to 100% EtOAc afforded the title compound (115 mg, 27% yield).

¹H-NMR (500 MHz, CD₃OD), δ ppm: 7.58 (d, J=2.0 Hz, 1H), 6.88 (d, J=2 Hz, 1H), 4.56 (m, 2H), 3.39 (m, 2H), 2.34 (m, 2H).

INT 9: 2,3,4,5-Tetrahydro-1H-pyrrolo[1,2-a][1,4]diazepin-1-one

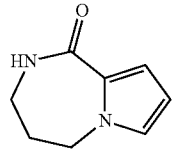

a) Methyl 1-(3-bromopropyl)-1H-pyrrole-2-carboxylate

To a solution of methyl 1H-pyrrole-2-carboxylate (440 mg, 3.52 mmol) in DMSO (12 mL), KOH (1.18 g, 21.10 mmol) was added and the mixture was stirred at rt for 1 h. 1,3-Dibromopropane (7.10 g, 35.2 mmol) was added and the mixture was stirred at rt for 24 h. Water was added, extracted with EtOAc and the organic layer was concentrated under vacuum. Purification by flash chromatography, silica gel, gradient CH to 100% EtOAc afforded the title compound (830 mg, 96% yield). HPLC (Method B): Ret, 5.15 min; ESI⁺-MS m/z, 246.0 (M+H).

b) Methyl 1-(3-azidopropyl)-1H-pyrrole-2-carboxylate

To a solution of the compound prepared in step a (805 mg, 3.27 mmol) in DMF (15 mL), NaN₃ (425 mg, 6.54 mmol) and TBAI (121 mg, 0.32 mmol) were added and the mixture was stirred at rt for 16 h. Water was added, the mixture was extracted with EtOAc and the organic layer was concentrated under vacuum. Purification by flash chromatography, silica gel, gradient CH to 100% EtOAc afforded the title compound (545 mg, 80% yield). HPLC (Method B): Ret, 4.96 min; ESI⁺-MS m/z, 209.1 (M+H).

c) Methyl 1-(3-aminopropyl)-1H-pyrrole-2-carboxylate

To a solution of the compound prepared in step b (500 mg, 2.40 mmol) in MeOH (6 mL), Pd on carbon (5% wt, 120 mg, 0.05 mmol) was added and the mixture was stirred at rt under H₂ atmosphere for 3 h. The reaction mixture was filtered through a pad of celite and the filtrate was concentrated under vacuum. Purification by flash chromatography, silica gel, gradient DCM to 40% MeOH afforded the title compound (335 mg, 77% yield). HPLC (Method B): Ret, 0.40 min; ESI⁺-MS m/z, 183.1 (M+H).

d) Title Compound

To a solution of the compound prepared in step c (300 mg, 1.64 mmol) in EtOH (6 mL), NaOMe (445 mg, 8.23 mmol) was added and the mixture was heated at 90° C. in a sealed tube for 5 h. The reaction mixture was cooled at rt and the solvent was removed under vacuum. Purification by flash chromatography, silica gel, gradient DCM to 35% MeOH afforded the title compound (175 mg, 70% yield).

¹H-NMR (300 MHz, CDCl₃), n ppm: 7.58 (bs, 1H), 8.06 (m, 1H), 6.85 (m, 1H), 6.71 (m, 1H), 6.12 (m, 1H), 4.15 (m, 2H), 3.31 (m, 2H), 2.12 (m, 2H).

INT 10: 8-Chloro-1-methyl-1,2,3,4-tetrahydro-5H-pyrido[2,3-e][1,4]diazepin-5-one

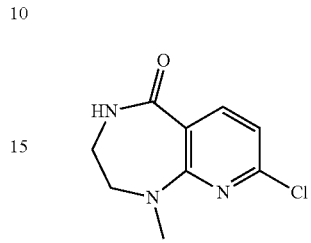

a) tert-Butyl (2-(2,6-dichloronicotinamide)ethyl)(methyl)carbamate

To a solution of 2,6-dichloronicotinoyl chloride (2.45 g, 11.67 mmol) in THF (18 mL) at 0° C., a solution of tert-butyl (2-aminoethyl)(methyl)carbamate (1.90 g, 10.90 mmol) in THF (27 mL) and TEA (5.64 mL, 40.50 mmol) were added. The mixture was stirred at 0° C. for 10 min and then at rt for 2.5 h. Water was added and the mixture was extracted with DCM, dried with Na₂SO₄ and the solvent was removed under vacuum. Purification by flash chromatography, silica gel, gradient CH to 100% EtOAc afforded the title compound (2.9 g, 76% yield). HPLC (Method B): Ret, 4.49 min; ESI⁺-MS m/z, 370.0 (M+Na).

b) 2,6-Dichloro-N-(2-(methylamino)ethyl)nicotinamide hydrochloride

To a solution of the compound prepared in step a (2.9 g, 8.33 mmol) in dioxane (15 mL), HCl (4M solution in dioxane, 31.2 mL, 125 mmol) was added and the mixture was stirred at rt for 2 h. The reaction mixture was concentrated to dryness under vacuum to afford the title compound as hydrochloride (2.3 g, quant yield). HPLC (Method B): Ret, 0.40 min; ESI⁺-MS m/z, 248.1 (M+H).

c) Title Compound

To a mixture of the compound prepared in step b (1.2 g, 3.74 mmol) and CsF (2.84 g, 18.69 mmol) in DMF (125 mL) under Ar atmosphere, TEA (1.25 mL, 8.97 mmol) was added and the mixture was heated at 75° C. for 16 h. The reaction mixture was cooled at rt and the solvent was removed under vacuum. Purification by flash chromatography, silica gel, gradient DCM to 40% MeOH, afforded the title compound (729 mg, 92% yield).

¹H-NMR (300 MHz, CDCl₃), δ ppm: 8.18 (d, J=8.0 Hz, 1H), 7.26 (bs, 1H), 6.69 (d, J=8.0 Hz, 1H), 3.65 (m, 2H), 3.54 (m, 2H), 3.19 (s, 3H).

INT 11: 8-(Ethylamino)-1-methyl-1,2,3,4-tetrahydro-5H-pyrido[2,3-e][1,4]diazepin-5-one

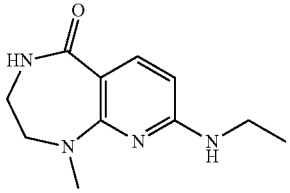 [SMILES: CCNc1ccc2c(n1)N(C)CCNC2=O]

A mixture of 8-chloro-1-methyl-1,2,3,4-tetrahydro-5H-pyrido[2,3-e][1,4]diazepin-5-one (INT 10, 95 mg, 0.45 mmol) and ethylamine (70% solution in water, 2.75 mL, 34.1 mmol) was irradiated with microwaves at 130° C. for 2 h. The solvent was removed under vacuum and the residue was purified by flash chromatography, silica gel, gradient DCM to 40% MeOH, to afford the title compound (84 mg, 85% yield).

$^1$H-NMR (300 MHz, CDCl$_3$), δ ppm: 8.15 (d, J=8.5 Hz, 1H), 6.19 (bs, 1H), 5.85 (d, J=8.5 Hz, 1H), 4.58 (bs, 1H), 3.58 (m, 2H), 3.49 (m, 2H), 3.38 (m, 2H), 3.17 (s, 3H), 1.26 (t, J=7.2 Hz, 3H).

INT 12: 8-(Dimethylamino)-1-methyl-1,2,3,4-tetrahydro-5H-pyrido[2,3-e][1,4]diazepin-5-one

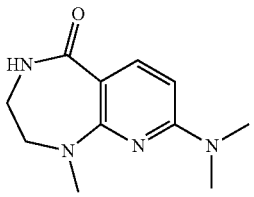 [SMILES: CN(C)c1ccc2c(n1)N(C)CCNC2=O]

8-Chloro-1-methyl-1,2,3,4-tetrahydro-5H-pyrido[2,3-e][1,4]diazepin-5-one (INT 10, 45 mg, 0.21 mmol) was treated with dimethylamine (40% solution in water, 2.0 mL, 16.16 mmol) in the conditions used in INT 11 to afford the title compound (42 mg, 90% yield).

$^1$H-NMR (400 MHz, CDCl$_3$), δ ppm: 8.13 (d, J=8.8 Hz, 1H), 6.43 (bs, 1H), 5.97 (d, J=8.8 Hz, 1H), 3.56 (m, 2H), 3.46 (m, 2H), 3.17 (s, 3H), 3.08 (s, 6H).

INT 13: 8-Amino-1-methyl-1,2,3,4-tetrahydro-5H-pyrido[2,3-e][1,4]diazepin-5-one

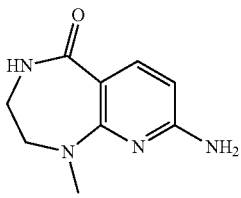

A dried Schlenk tube was charged with Pd$_2$(dba)$_3$ (87 mg, 0.094 mmol), [1,1'-biphenyl]-2-yldicyclohexylphosphane (79 mg, 0.22 mmol) and 8-chloro-1-methyl-1,2,3,4-tetrahydro-5H-pyrido[2,3-e][1,4]diazepin-5-one (INT 10, 400 mg, 1.89 mmol). The Schlenk tube was evacuated and back-filled with Ar. Degassed THF (3.4 mL) and lithium bis(trimethylsilyl)amide (1M solution in THF, 4.72 mL, 4.72 mmol) were added and the mixture was heated at 70° C. for 16 h. The reaction mixture was cooled at rt, a solution of TBAF (1M in THF, 5.67 mL, 5.67 mmol) was added and the mixture was stirred at rt for 30 min. DCM was added, washed with water, dried with Na$_2$SO$_4$ and the solvent was removed under vacuum. Purification by flash chromatography, silica gel, gradient DCM to 20% MeOH, afforded the title compound (292 mg, 80% yield).

$^1$H-NMR (400 MHz, CD$_3$OD), δ ppm: 7.99 (d, J=8.6 Hz, 1H), 6.03 (d, J=8.6 Hz, 1H), 3.61 (m, 2H), 3.48 (m, 2H), 3.18 (s, 3H).

INT 14: 8-Methoxy-1-methyl-1,2,3,4-tetrahydro-5H-pyrido[2,3-e][1,4]diazepin-5-one

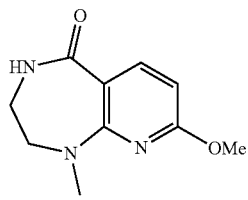

To a solution of 8-chloro-1-methyl-1,2,3,4-tetrahydro-5H-pyrido[2,3-e][1,4]diazepin-5-one (INT 10, 500 mg, 2.36 mmol) in MeOH (17 mL), NaOMe (766 mg, 14.17 mmol) was added and the mixture was irradiated with MW at 110° C. for 2 h. The solvent was removed under vacuum and the residue was purified by flash chromatography, silica gel, gradient DCM to 30% MeOH to afford the title compound (440 mg, 90% yield). $^1$H-NMR (300 MHz, CD$_3$OD), δ ppm: 8.09 (d, J=8.5 Hz, 1H), 6.10 (d, J=8.5 Hz, 1H), 3.91 (s, 3H), 3.63 (m, 2H), 3.47 (m, 2H), 3.22 (s, 3H).

INT 15: 1-Methyl-1,2,3,4-tetrahydro-5H-pyrido[2,3-e][1,4]diazepin-5-one

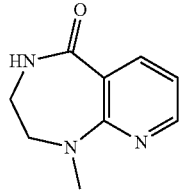

To a solution of 8-chloro-1-methyl-1,2,3,4-tetrahydro-5H-pyrido[2,3-e][1,4]diazepin-5-one (INT 10, 550 mg, 2.60 mmol) in THF (12 mL), Pd on carbon (5% wt, 221 mg, 0.10 mmol) was added and the mixture was cooled at 0° C. in a sealed tube. Triethylsilane (1.51 g, 13.0 mmol) was added, the reaction mixture was stirred at 0° C. for 5 min and then at rt for 16 h. The reaction mixture was filtered through a pad of celite and the filtrated was concentrated under vacuum. Purification by flash chromatography, silica gel, gradient DCM to 30% MeOH afforded the title compound (378 mg, 82% yield).

¹H-NMR (300 MHz, CDCl₃), δ ppm: 8.32 (dd, J1=2.0 Hz, J2=4.6 Hz, 1H), 8.21 (dd, J1=2.0 Hz, J2=7.6 Hz, 1H), 7.01 (bs, 1H), 6.75 (dd, J1=4.6 Hz, J2=7.6 Hz, 1H), 3.62 (m, 2H), 3.54 (m, 2H), 3.16 (s, 3H).

INT 16: 1,8-Dimethyl-1,2,3,4-tetrahydro-5H-pyrido[2,3-e][1,4]diazepin-5-one

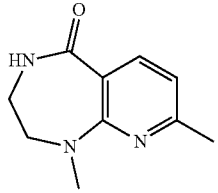

To a mixture of 8-chloro-1-methyl-1,2,3,4-tetrahydro-5H-pyrido[2,3-e][1,4]diazepin-5-one (INT 10, 50 mg, 0.23 mmol), methylboronic acid (16 mg, 0.27 mmol), Pd(Ph₃)₄ (27 mg, 0.024 mmol) and K₂CO₃ (98 mg, 0.71 mmol) under Ar, degassed dioxane (1.2 mL) was added and the mixture was heated at 130° C. in a sealed tube for 48 h. The reaction mixture was cooled at rt and filtered through a pad of celite. The filtrated was concentrated under vacuum and the residue was purified by flash chromatography, silica gel, gradient Hex to 100% acetone to afford the title compound (45 mg, 77% yield).

¹H-NMR (400 MHz, CDCl₃), δ ppm: 8.15 (d, J=7.8 Hz, 1H), 6.61 (d, J=7.8 Hz, 1H), 6.56 (bs, 1H), 3.61 (m, 2H), 3.53 (m, 2H), 3.19 (s, 3H), 2.45 (s, 3H).

INT 17: 1-Methyl-8-(trifluoromethyl)-1,2,3,4-tetrahydro-5H-pyrido[2,3-e][1,4]diazepin-5-one

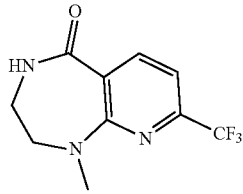 [SMILES: CN1CCNC(=O)c2ccc(C(F)(F)F)nc21]

The title compound was prepared following the sequence used in INT 10 and starting from 2-chloro-6-(trifluoromethyl)nicotinoyl chloride.

¹H-NMR (400 MHz, CDCl₃), δ ppm: 8.38 (d, J=7.8 Hz, 1H), 7.05 (d, J=7.8 Hz, 1H), 6.96 (bs, 1H), 3.70 (m, 2H), 3.58 (m, 2H), 3.23 (s, 3H).

INT 18: tert-Butyl ethyl((1-methyl-5-oxo-1,4-diazepan-6-yl)methyl)carbamate

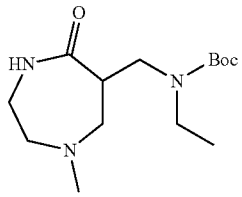 [SMILES: CCN(CC1CN(C)CCNC1=O)C(=O)OC(C)(C)C]

a) tert-Butyl 4-(4-methoxybenzyl)-5-oxo-1,4-diazepane-1-carboxylate

To a solution of tert-butyl 5-oxo-1,4-diazepane-1-carboxylate (1.0 g, 4.67 mmol) In DMF (18 mL) cooled at 0° C., NaH (60% in mineral oil, 280 mg, 7.0 mmol) was added and the mixture was stirred at rt for 45 min. 4-Methoxybenzylchloride (1.1 g, 7.0 mmol) and TBAI (172 mg, 0.46 mmol) were added and the mixture was heated at 55° C. for 16 h. The reaction mixture was cooled at rt, water was added and extracted with EtOAc. The organic layer was dried with Na₂SO₄, filtered and the solvent was removed under vacuum. Purification by flash chromatography, silica gel, gradient Hex to 100% EtOAc afforded the title compound (944 mg, 60% yield). ESI⁺-MS m/z, 357.1 (M+Na).

b) 1-(tert-Butyl) 6-methyl 4-(4-methoxybenzyl)-5-oxo-1,4-diazepane-1,6-dicarboxylate To a solution of the compound prepared in step a (650 mg, 1.94 mmol) in THF (11.5 mL) cooled at −78° C. under Ar, lithium bis(trimethylsilyl)amide (1M in THF solution, 3.89 mL, 3.89 mmol) was slowly added and the mixture was stirred at −78° C. for 1 h. Dimethyl carbonate (385 mg, 4.28 mmol) was added and the mixture was stirred from −78° C. to 0° C. for 3 h. Water was added, the mixture was extracted with EtOAc and the organic layer was dried with Na₂SO₄, filtered and the solvent was removed under vacuum. Purification by flash chromatography, silica gel, gradient Hex to 100% EtOAc afforded the title compound (660 mg, 87% yield). HPLC (Method B): Ret, 4.94 min; ESI⁺-MS m/z, 393.2 (M+H).

c) tert-Butyl 6-(hydroxymethyl)-4-(4-methoxybenzyl)-5-oxo-1,4-diazepane-1-carboxylate To a suspension of the compound prepared in step b (528 mg, 1.34 mmol) and CaCl₂ (149 mg, 1.34 mmol) in MeOH (2.7 mL) cooled at 0° C., NaBH₄ (102 mg, 2.69 mmol) was added. The reaction mixture was stirred at 0° C. for 2 h and then, at rt for 14 h. The solvent was removed under vacuum and a 1 M solution of citric acid was added until complete solution. The aq layer was extracted with DCM. The organic layer was dried with Na₂SO₄, filtered and the solvent was removed under vacuum to afford the title compound (1.34 g, quant yield) that was used in the next step without further purification. HPLC (Method B): Ret, 4.53 min; ESI⁺-MS m/z, 365.2 (M+H).

d) tert-Butyl 4-(4-methoxybenzyl)-6-(((methylsulfonyl)oxy)methyl)-5-oxo-1,4-diazepane-1-carboxylate To a solution of the compound prepared in step c (490 mg, 1.34 mmol) in DCM (9.5 mL) cooled at 0° C., methanesulfonyl chloride (185 mg, 1.61 mmol) and TEA (272 mg, 2.69 mmol) were added and the mixture was stirred at 0° C. for 1 h. Water was added and the mixture was extracted with DCM. The organic phase was dried with Na₂SO₄ and filtered and the solvent was removed under vacuum to afford the title compound (580 mg, quant yield) that was used in the next step without further purification. HPLC (Method B): Ret, 4.99 min; ESI⁺-MS m/z, 465.1 (M+Na).

e) tert-Butyl 6-((ethylamino)methyl)-4-(4-methoxybenzyl)-5-oxo-1,4-diazepane-1-carboxylate The compound prepared in step d (657 mg, 1.48 mmol) was treated with ethylamine (70% solution in water, 3.11 mL, 38.6 mmol) and the mixture was heated at 130° C. in a sealed tube for 1 h. The reaction mixture was cooled at rt, water was added and the mixture was extracted with DCM. The solvent was removed under vacuum to afford the title compound (515 mg, 89% yield) that was used in the next step without further purification. HPLC (Method B): Ret, 3.81 min; ESI⁺-MS m/z, 392.2 (M+Na).

f) tert-Butyl 6-((((benzyloxy)carbonyl)(ethyl)amino) methyl)-4-(4-methoxybenzyl)-5-oxo-1,4-diazepane-1-carboxylate To a solution of the compound prepared in step e (509 mg, 1.30 mmol) in DCM (7 mL) cooled at 0° C. under Ar atmosphere, TEA (145 mg, 1.43 mmol) and benzyl chloroformate (228 mg, 1.34 mmol) were added and the mixture was stirred at rt for 16 h. Water was added, extracted with DCM, dried with Na₂SO₄, filtered and the solvent was removed under vacuum. Purification by flash chromatography, silica gel, gradient Hex to 100% EtOAc afforded the title compound (556 mg, 81% yield). HPLC (Method B): Ret, 6.42 min; ESI⁺-MS m/z, 526.3 (M+H).

g) Benzyl ethyl((1-(4-methoxybenzyl)-7-oxo-1,4-diazepan-6-yl)methyl)carbamate

To a solution of the compound prepared in step f (720 mg, 1.37 mmol) in dioxane (2.5 mL), HCl 4M solution in dioxane (4.8 mL, 19.18 mmol) was added and the mixture was stirred at rt for 45 min. The solvent was removed under vacuum to afford the title compound (630 mg, quant yield) as hydrochloride that was used in the next step without further purification. HPLC (Method B): Ret, 4.26 min; ESI⁺-MS m/z, 426.2 (M+H).

h) Benzyl ethyl((4-(4-methoxybenzyl)-1-methyl-5-oxo-1,4-diazepan-6-yl)methyl) carbamate To a solution of the compound prepared in step g (239 mg, 0.51 mmol) in DCE (9.6 mL), DIPEA (134 mg, 1.03 mmol), paraformaldehyde (60 mg, 1.91 mmol), NaBH(OAc)₃ (406 mg, 1.91 mmol) and acetic acid (31 mg, 0.51 mmol) were added and the reaction mixture was stirred at rt for 64 h. NaHCO₃ sat solution was added, extracted with DCM, dried with Na₂SO₄, filtered and concentrated under vacuum. Purification by flash chromatography, silica gel, gradient DCM to 20% MeOH afforded the title compound (207 mg, 91% yield).
¹H-NMR (300 MHz, CDCl₃), δ ppm: 7.37 (m, 5H), 7.18 (m, 2H), 6.85 (m, 2H), 5.15 (m, 2H), 4.52 (m, 2H), 3.81 (s, 3H), 3.59 (m, 3H), 3.39 (m, 2H), 3.15 (m, 2H), 2.75 (m, 2H), 2.21 (m, 3H), 1.90 (m, 2H), 1.15 (m, 3H).

i) 6-((Ethylamino)methyl)-1-methyl-1,4-diazepan-5-one

A mixture of the compound prepared in step h (100 mg, 0.22 mmol), TFA (1.67 mL, 21.61 mmol) and methanesulfonic acid (33 mg, 0.34 mmol) was heated at 82° C. for 16 h. The reaction mixture was cooled at rt, MeOH was added and the solvent was removed under vacuum to afford the title compound (83 mg, 96% yield) as trifluoroacetate salt, that was used in the next step without further purification. HPLC (Method B): Ret, 0.42 min; ESI⁺-MS m/z, 186.1 (M+H).

j) Title Compound

To a solution of the compound prepared in step i (80 mg, 0.21 mmol) in DCE (1.2 mL) cooled at 0° C., TEA (85 mg, 0.84 mmol), a solution of di-tert-butyl dicarbonate (69 mg, 0.31 mmol) in DCE (0.4 mL) and DMAP (1.3 mg, 0.01 mmol) were added and the mixture was stirred at rt for 20 h. The solvent was removed under vacuum. Purification by flash chromatography, silica gel, gradient DCM to 40% MeOH afforded the title compound (45 mg, 75% yield).
¹H-NMR (300 MHz, CDCl₃), δ ppm: 6.06 (bs, 1H), 3.46 (m, 3H), 3.32 (m, 1H), 3.20 (m, 2H), 2.97 (m, 1H), 2.84 (m, 2H), 2.35 (s, 3H), 2.21 (m, 2H), 1.47 (s, 9H), 1.12 (t, J=7.0 Hz, 3H).

INT 19: tert-Butyl ethyl((2-oxoazepan-3-yl)methyl)carbamate

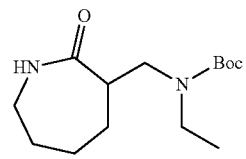 [SMILES: CCN(CC1CCCCNC1=O)C(=O)OC(C)(C)C]

Was prepared following the sequence used in INT 18 from azepan-2-one.
¹H-NMR (300 MHz, CDCl₃), δ ppm: 5.90 (bs, 1H), 3.34 (m, 6H), 2.84 (m, 1H), 2.02 (m, 1H), 1.80 (m, 2H), 1.57 (m, 1H), 1.46 (s, 9H), 1.34 (m, 2H), 1.09 (t, J=7.0 Hz, 3H).

INT 20: tert-Butyl ((4-methyl-7-oxo-1,4-diazepan-5-yl)methyl)carbamate

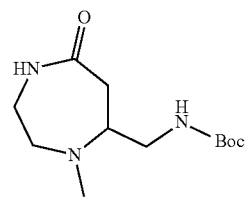 [SMILES: CN1CCNC(=O)CC1CNC(=O)OC(C)(C)C]

To a solution of tert-butyl 2-oxo-2,5-dihydro-1H-pyrrole-1-carboxylate (1.0 g, 5.73 mmol) in MeOH (11.5 mL), N1-methylethane-1,2-diamine (425 mg, 5.73 mmol) was added and the mixture was stirred at rt for 48 h. The solvent was removed under vacuum and the residue was purified by flash chromatography, silica gel, gradient DCM to 40% MeOH to afford the title compound (617 mg, 41% yield).
¹H-NMR (500 MHz, CD₃OD), δ ppm: 3.45 (m, 2H), 3.26 (m, 1H), 3.16 (m, 1H), 3.08 (m, 1H), 2.96 (m, 1H), 2.85 (m, 1H), 2.77 (s, 1H), 2.64 (m, 1H), 2.58 (s, 3H).

INT 21: 2-(Trimethylsilyl ethyl (2-(1,4-diazepan-1-yl)-2-oxoethyl)(ethyl)carbamate INT 22: 2-(Trimethylsilyl)ethyl (S)-(3-(4-(chloromethyl)-3-methylphenoxy)-3-(thiophen-2-yl)propyl)(methyl)carbamate

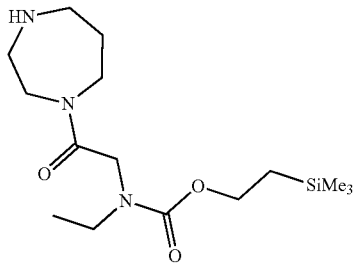 [SMILES: CCN(CC(=O)N1CCCNCC1)C(=O)OCC[Si](C)(C)C]

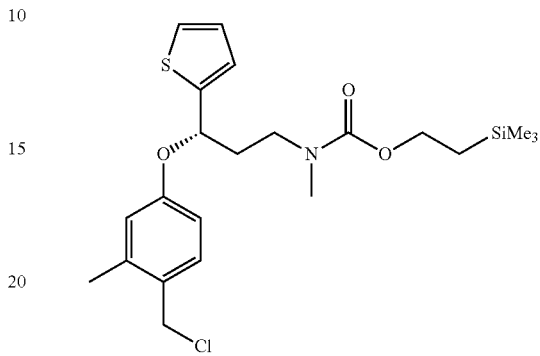

a) N-Ethyl-N-((2-(trimethylsilyl)ethoxy)carbonyl)glycine

To a solution of N-ethyl glycine trifluoroacetate salt (646 mg, 2.27 mmol) in DCM (5 mL), DIPEA (1.1 mL, 6.30 mmol) and a solution of 4-nitrophenyl (2-(trimethylsilyl) ethyl) carbonate (900 mg, 3.18 mmol) in DCM (5 mL) were added and the mixture was stirred at rt for 64 h. NaHCO$_3$ sat solution was added and washed with DCM. The aq layer was treated with HCl 1N solution until pH<4 and extracted with DCM. The organic layer was dried with Na$_2$SO$_4$, filtered and concentrated under vacuum. Purification by flash chromatography, silica gel, gradient DCM to 30% MeOH afforded the title compound (542 mg, 69% yield).

$^1$H-NMR (400 MHz, CDCl$_3$), δ ppm: 7.96 (bs, 1H), 4.22 (m, 2H), 4.02 (m, 2H), 3.39 (m, 2H), 1.12 (t, J=7.3 Hz, 3H), 1.04 (m, 2H), 0.06 (s, 9H).

b) Title Compound

To a solution of the compound prepared in step a (250 mg, 1.01 mmol) in dry DMF (3 mL), HATU (500 mg, 1.31 mmol) and a solution of 1,4-diazepane (506 mg, 5.05 mmol) in DMF (2 mL) were added and the mixture was stirred at rt for 16 h. NH$_4$Cl sat solution was added, extracted with EtOAc, dried with Na$_2$SO$_4$, filtered and concentrated under vacuum. Purification by flash chromatography, silica gel, gradient DCM to 30% MeOH afforded the title compound (277 mg, 83% yield).

$^1$H-NMR (300 MHz, CDCl$_3$), δ ppm: 4.16 (m, 2H), 4.04 (m, 2H), 3.85 (m, 2H), 3.63 (m, 2H), 3.38 (m, 4H), 2.21 (m, 4H), 1.12 (m, 3H), 1.00 (m, 2H), 0.04 (s, 9H).

a) Methyl (S)-4-(3-((tert-butoxycarbonyl)(methyl)amino)-1-(thiophen-2-yl)propoxy)-2-methylbenzoate To a solution of tert-butyl (S)-(3-hydroxy-3-(thiophen-2-yl)propyl)(methyl)carbamate (2.15 g, 7.94 mmol) and methyl 4-fluoro-2-methylbenzoate (2.67 g, 15.87 mmol) in DMA (44 mL), NaH (60% suspension in mineral oil, 476 mg, 11.91 mmol) was added and the reaction mixture was stirred at rt for 2 h. Water was added, extracted with EtOAc, dried with Na$_2$SO$_4$, filtered and concentrated under vacuum. Purification by flash chromatography, silica gel, gradient CH to 100% EtOAc afforded the title compound (3.10 g, 93% yield). HPLC (Method B): Ret, 6.65 min; ESI$^+$-MS m/z, 442.1 (M+Na).

b) Methyl (S)-2-methyl-4-(3-(methyl((2-(trimethylsilyl)ethoxy)carbonyl)amino)-1-(thiophen-2-yl)propoxy)benzoate In a round-bottom flask, ZnBr$_2$ (5.5 g, 24.67 mmol) was dried under vacuum at 200° C. for 4 h. Once the solid reached rt, a solution of the compound obtained in step a (2.07 g, 4.93 mmol) in DCM (49 mL) was added and the mixture was stirred at rt under Ar atmosphere for 20 h. Water was added and the mixture was stirred for 2 h. The layers were decanted, the aq layer was extracted with DCM and the organic layer was concentrated under vacuum. The residue was dissolved in DCM (8.5 mL), DIPEA (2.6 mL, 15.15 mmol) and a solution of 4-nitrophenyl (2-(trimethylsilyl) ethyl) carbonate (1.6 g, 5.55 mmol) in DCM (8.5 mL) were added and the mixture was stirred at rt for 16 h. The reaction mixture was concentrated under vacuum. Purification by flash chromatography, silica gel, gradient CH to 100% EtOAc afforded the title compound (1.1 g, 47% yield). HPLC (Method B): Ret, 7.18 min; ESI$^+$-MS m/z, 486.1 (M+Na).

c) 2-(Trimethylsilyl)ethyl (S)-(3-(4-(hydroxymethyl)-3-methylphenoxy)-3-(thiophen-2-yl)propyl)(methyl)carbamate To a solution of the compound prepared in step b (103 mg, 0.22 mmol) in Et$_2$O (1.5 mL) at rt, under Ar atmosphere, lithium tri-tert-butoxyaluminum hydride (1M solution in THF, 1.5 mL, 1.5 mmol) was added. The reaction mixture was stirred at rt for 5 min, and then, heated at 50° C. for 16 h. The reaction mixture was cooled at 0° C., EtOAc and potassium sodium tartrate tetrahydrate sat solution were slowly added and stirred for 45 min. The layers were decanted and the aq layer was extracted with EtOAc. The combined organic layers were dried with Na$_2$SO$_4$, filtered and concentrated under vacuum. Purification by flash chromatography, silica gel, gradient CH to 100% EtOAc afforded the title compound (62 mg, 64% yield). HPLC (Method B): Ret, 6.44 min; ESI$^+$-MS m/z, 458.2 (M+Na).

d) Title Compound

To a solution of the compound prepared in step c (174 mg, 0.40 mmol) in DCM (3.3 mL) cooled at 0° C., DIPEA (103 mg, 0.80 mmol) and methanesulfonyl chloride (59 mg, 0.52 mmol) were added and the reaction mixture was stirred at rt for 16 h. Cold water was added and the mixture extracted with DCM. The organic layer was washed with cold brine solution, dried with Na$_2$SO$_4$, filtered and concentrated under vacuum to afford the title compound that was used in the next step without further purification. HPLC (Method B): Ret, 7.53 min; ESI$^+$-MS m/z, 476.1 (M+Na).

INT 23: 2-(Trimethylsilyl)ethyl (S)-(3-(4-(chloromethyl)-3-fluorophenoxy)-3-(thiophen-2-yl)propyl)(methyl)carbamate

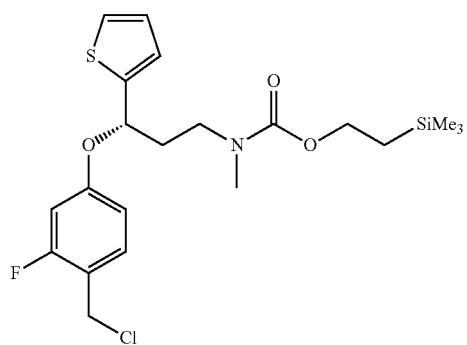 [SMILES: CN(CC[C@H](Oc1ccc(CCl)c(F)c1)c1cccs1)C(=O)OCC[Si](C)(C)C]

The title compound was prepared following the sequence used in INT 22 and starting from methyl 2,4-difluorobenzoate.

SYNTHESIS OF EXAMPLES

Example 1: N-methyl-3-(3-((1-methyl-1,2,3,5-tetrahydro-4H-benzo[e][1,4]diazepin-4-yl)methyl)phenoxy)-3-(thiophen-2-yl)propan-1-amine

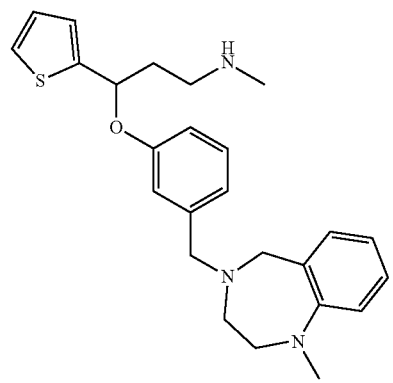 [SMILES: CNCCC(Oc1cccc(CN2CCN(C)c3ccccc3C2)c1)c1cccs1]

a) 3-(3-Chloro-1-(thiophen-2-yl)propoxy)benzaldehyde

To a solution of 3-chloro-1-(thiophen-2-yl)propan-1-ol (1.00 g, 5.66 mmol) in THF (10 mL) 3-hydroxybenzaldehyde (0.69 g, 5.66 mmol) and PPh$_3$ (1.63 g, 6.23 mmol) were added. The mixture was cooled to 0° C. and DIAD (1.26 g, 6.23 mmol) was added dropwise. The reaction mixture was warmed slowly at rt and stirred for 16 h. The solvent was removed under vacuum and the residue was purified by flash chromatography, silica gel, gradient CH to 100% EtOAc to afford the title compound (700 mg, 44% yield). HPLC (Method B): Ret, 5.56 min; ESI$^+$-MS m/z, 281.2 (M+H).

b) 4-(3-(3-Chloro-1-(thiophen-2-yl)propoxy)benzyl)-1-methyl-2,3,4,5-tetrahydro-1H-benzo[e][1,4]diazepine To a solution of the compound prepared in step a (100 mg, 0.35 mmol) in DCE (5 mL), 1-methyl-2,3,4,5-tetrahydro-1H-benzo[e][1,4]diazepine (64 mg, 0.39 mmol), NaBH(OAc)$_3$ (113 mg, 0.53 mmol) and DIPEA (55 mg, 0.42 mmol) were added and the mixture was stirred at rt for 16 h. NaHCO$_3$ sat solution was added, the solution was extracted with DCM and the organic layer was concentrated under vacuum.

Purification by flash chromatography, silica gel, gradient CH to 100% EtOAc, afforded the title compound (88 mg, 58% yield).

$^1$H-NMR (400 MHz, CDCl$_3$), δ ppm: 7.22 (m, 3H), 7.05 (m, 1H), 6.93 (m, 7H), 5.71 (m, 1H), 3.83 (m, 1H), 3.77 (s, 2H), 3.63 (m, 1H), 3.55 (s, 2H), 2.99 (m, 2H), 2.93 (m, 2H), 2.92 (s, 3H), 2.59 (m, 1H), 2.33 (m, 1H).

c) Title Compound

To a solution of the compound obtained in step b (88 mg, 0.20 mmol) in EtOH (0.2 mL), methylamine (40% water solution, 1.0 mL, 13.4 mmol) was added and the mixture was heated in a sealed tube at 100° C. for 1 h. The mixture was cooled at rt and concentrated under vacuum. Purification by flash chromatography, silica gel, gradient DCM to 20% MeOH, afforded the title compound (43 mg, 50% yield). HPLC (Method A): Ret, 4.89 min; ESI$^+$-MS m/z, 422.3 (M+H).

Example 2: (4-Methyl-1,4-diazepan-1-yl)(3-(3-(methylamino)-1-(thiophen-2-yl)propoxy)phenyl)methanone

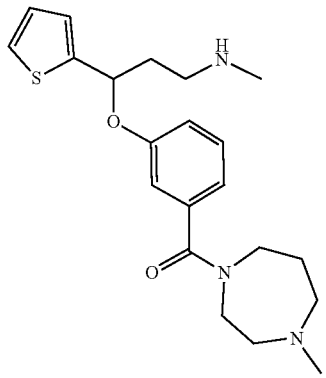 [SMILES: CNCCC(Oc1cccc(C(=O)N2CCCN(C)CC2)c1)c1cccs1]

a) Methyl 3-(3-chloro-1-(thiophen-2-yl)propoxy)benzoate

3-Chloro-1-(thiophen-2-yl)propan-1-ol was treated with methyl 3-hydroxybenzoate in the conditions used in Ex 1 step a, heating at 50° C. for 16 h to afford the title compound (51% yield). HPLC (Method B): Ret, 5.80 min; ESI$^-$-MS m/z, 309.1 (M−H).

b) 3-(3-Chloro-1-(thiophen-2-yl)propoxy)benzoic acid

To a solution of the compound prepared in step a (1.0 g, 3.22 mmol) in MeOH (32 mL), LiOH monohydrate (810 mg, 19.31 mmol) was added and the mixture was heated at 100° C. for 1 h. The reaction mixture was cooled at rt, citric acid solution was added until pH=5 and extracted with DCM to afford the title compound, that was used in the next step without further purification (quant yield). HPLC (Method B): Ret, 5.14 min; ESI$^+$-MS m/z, 319.0 (M+Na).

c) (3-(3-Chloro-1-(thiophen-2-yl)propoxy)phenyl)(4-methyl-1,4-diazepan-1-yl) methanone To a solution of the compound prepared in step b (130 mg, 0.43 mmol) in DCM (2 mL), HATU (183 mg, 0.48 mmol) was added and the mixture was stirred at rt for 30 min. DIPEA (62 mg, 0.48 mmol) and 1-methyl-1,4-diazepane (50 mg, 0.43 mmol) were added and the mixture was stirred at rt for 16 h. DCM was added, washed with water and brine, dried with Na$_2$SO$_4$ and the solvent was removed under vacuum. Purification by flash chromatography, silica gel, gradient DCM to 10% MeOH, afforded the title compound (128 mg, 74% yield). HPLC (Method B): Ret, 4.04 min; ESI$^+$-MS m/z, 393.1 (M+H).

d) Title Compound

The compound prepared in step c was treated with the conditions used in Ex 1 step c to afford the title compound (34% yield). HPLC (Method A): Ret, 4.11 min; ESI$^+$-MS m/z, 388.2 (M+H).

This method was used for the preparation of Ex 3 and 4 using suitable starting materials:

| EX | Structure | Chemical name | Method | Ret (min) | MS |
|----|-----------|---------------|--------|-----------|-----|
| 3 | 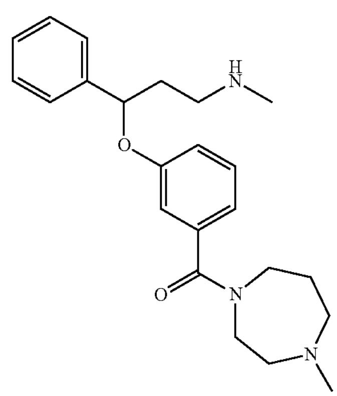 [SMILES: CNCCC(Oc1cccc(C(=O)N2CCCN(C)CC2)c1)c1ccccc1] | (4-Methyl-1,4-diazepan-1-yl)(3-(3-(methylamino)-1-phenylpropoxy)phenyl)methanone | A | 4.14 | |

| EX | Structure | Chemical name | Method | Ret (min) | MS |
|---|---|---|---|---|---|
| 4 | 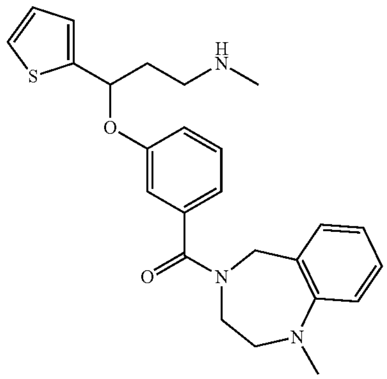 [SMILES: CNCCC(Oc1cccc(C(=O)N2CCN(C)c3ccccc3C2)c1)c1cccs1] | (1-Methyl-1,2,3,5-tetrahydro-4H-benzo[e][1,4]diazepin-4-yl)(3-(3-(methylamino)-1-(thiophen-2-yl)propoxy)phenyl)methanone | A | 6.00 | 436.2 (M + H) |

Example 5: N-methyl-3-(3-(4-methyl-1,4-diazepan-1-yl)phenoxy)-3-phenylpropan-1-amine

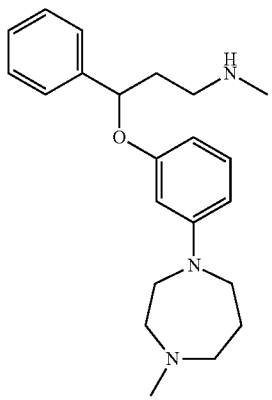 [SMILES: CNCCC(Oc1cccc(N2CCCN(C)CC2)c1)c1ccccc1]

a) tert-Butyl methyl(3-(3-(4-methyl-1,4-diazepan-1-yl)phenoxy)-3-phenylpropyl) carbamate A mixture of CuI (25 mg, 0.13 mmol) and L-Proline (23 mg, 0.19 mmol) in dry DMSO (1.2 mL) was stirred at rt under Ar atmosphere for 15 min. tert-Butyl (3-(3-iodophenoxy)-3-phenylpropyl)(methyl)carbamate (322 mg, 0.69 mmol), $K_2CO_3$ (182 mg, 1.31 mmol) and 1-methyl-1,4-diazepane (75 mg, 0.65 mmol) were added and the mixture was heated at 100° C. for 42 h. The reaction mixture was cooled at rt, DCM was added, washed with water and $NH_4Cl$ sat solution. The organic layer was concentrated under vacuum and the residue was purified by flash chromatography, silica gel, gradient from Hex to 100% acetone, to afford the title compound (78 mg, 26% yield). HPLC (Method A): Ret, 6.93 min; $ESI^+$-MS m/z, 454.3 (M+H).

b) Title Compound

To a solution of the compound prepared in step a (9 mg, 0.020 mmol) in dioxane (0.1 mL), 4 M HCl solution in dioxane (0.14 mL, 0.55 mmol) was added and the mixture was stirred at it for 1 h. The reaction mixture was concentrated to dryness under vacuum. DCM was added, washed with $Na_2CO_3$ 10% aq solution and concentrated to afford the title compound (7 mg, quant yield). HPLC (Method A): Ret, 4.55 min; $ESI^+$-MS m/z, 354.2 (M+H).

This method was used for the preparation of Ex 6-10 using suitable starting materials:

| EX | Structure | Chemical name | Method | Ret (min) | MS |
|---|---|---|---|---|---|
| 6 | 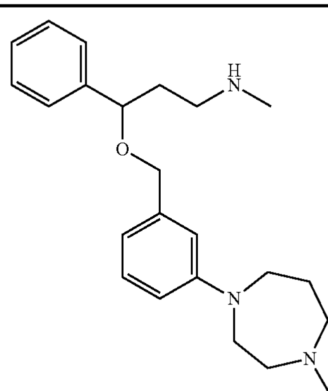 | N-methyl-3-((3-(4-methyl-1,4-diazepan-1-yl)benzyl)oxy)-3-phenylpropan-1-amine | A | 4.74 | 368.2 (M + H) |

| EX | Structure | Chemical name | Method | Ret (min) | MS |
|---|---|---|---|---|---|
| 7 | 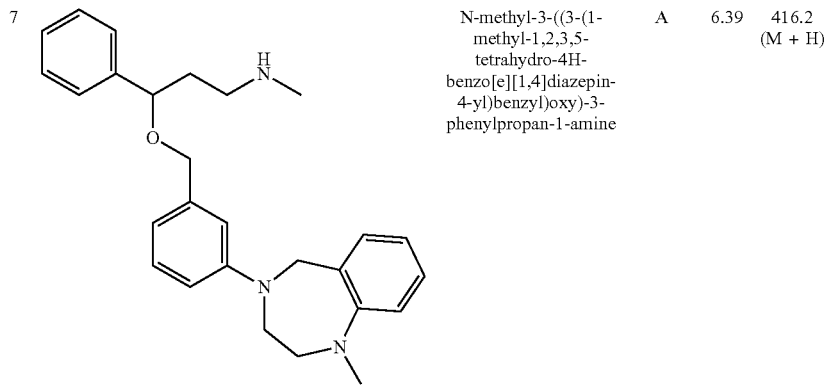 | N-methyl-3-((3-(1-methyl-1,2,3,5-tetrahydro-4H-benzo[e][1,4]diazepin-4-yl)benzyl)oxy)-3-phenylpropan-1-amine | A | 6.39 | 416.2 (M + H) |
| 8 | 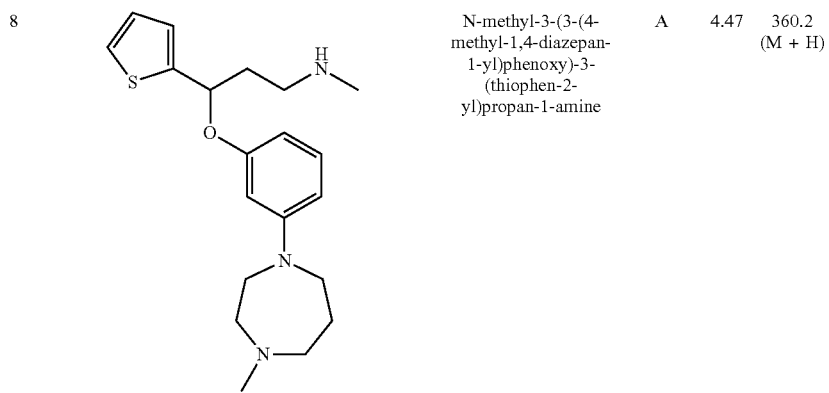 | N-methyl-3-(3-(4-methyl-1,4-diazepan-1-yl)phenoxy)-3-(thiophen-2-yl)propan-1-amine | A | 4.47 | 360.2 (M + H) |

| EX | Structure | Chemical name | Method | Ret (min) | MS |
|---|---|---|---|---|---|
| 9 | 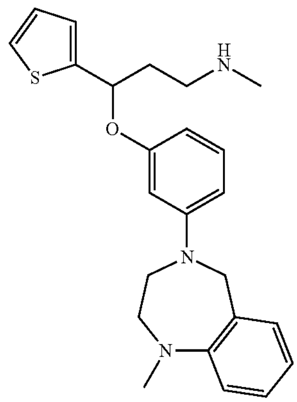 [SMILES: CNCCC(Oc1cccc(N2CCN(C)c3ccccc3C2)c1)c1cccs1] | N-methyl-3-(3-(1-methyl-1,2,3,5-tetrahydro-4H-benzo[e][1,4]diazepin-4-yl)phenoxy)-3-(thiophen-2-yl)propan-1-amine | A | 6.07 | 408.2 (M + H) |
| 10 | 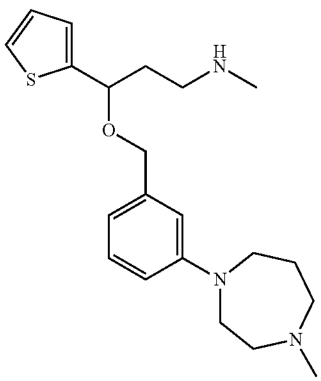 [SMILES: CNCCC(OCc1cccc(N2CCCN(C)CC2)c1)c1cccs1] | N-methyl-3-((3-(4-methyl-1,4-diazepan-1-yl)benzyl)oxy)-3-(thiophen-2-yl)propan-1-amine | A | 4.62 | 374.2 (M + H) |

In Ex 8-10 Teoc was used as protecting group.

Example 11: 2-(Ethylamino)-1-(4-(3-(3-(methylamino)-1-(thiophen-2-yl)propoxy) phenyl)-1,4-diazepan-1-yl)ethan-1-one

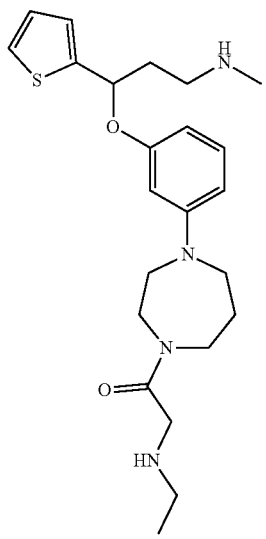 [SMILES: CCNCC(=O)N1CCCN(c2cccc(OC(CCNC)c3cccs3)c2)CC1]

a) 2-(Trimethylsilyl)ethyl (3-(3-(4-(N-ethyl-N-((2-(trimethylsilyl)ethoxy) carbonyl)glycyl)-1,4-diazepan-1-yl)phenoxy)-3-(thiophen-2-yl)propyl) (methyl) carbamate A mixture of Pd$_2$(dba)$_3$ (18 mg, 0.019 mmol), XPhos (37 mg, 0.07 mmol), sodium tert-butoxide (52 mg, 0.54 mmol) 2-(trimethylsilyl)ethyl (2-(1,4-diazepan-1-yl)-2-oxoethyl)(ethyl)carbamate (INT 21, 153 mg, 0.46 mmol) and 2-(trimethylsilyl)ethyl (3-(3-iodophenoxy)-3-(thiophen-2-yl)propyl)(methyl)carbamate (200 mg, 0.38 mmol) in dioxane (2 mL) was heated at 130° C. in a sealed tube for 20 h under Ar atmosphere. The reaction mixture was cooled at rt, filtered through a pad of celite and the solution was concentrated under vacuum. Purification by flash chromatography, silica gel, gradient DCM to 30% MeOH, afforded the title compound (147 mg, 53% yield). HPLC (Method B): Ret, 7.33 min; ESI$^+$-MS m/z, 719.3 (M+H).

b) Title Compound

A mixture of the compound prepared in step a (121 mg, 0.16 mmol) and CsF (256 mg, 1.68 mmol) in DMF (1 mL) was heated at 90° C. for 90 min. The reaction mixture was cooled at rt, DCM was added, filtered through a pad of celite and concentrated under vacuum. Purification by flash chromatography, silica gel, gradient DCM to 30% MeOH:0.05% NH$_3$ aq, afforded the title compound (51 mg, 71% yield). HPLC (Method A): Ret, 4.55 min: ESI$^+$-MS m/z, 431.3 (M+H).

This method was used for the operation of Ex 12-13 using suitable starting materials:

| EX | Structure | Chemical name | Method | Ret (min) | MS |
|---|---|---|---|---|---|
| 12 | 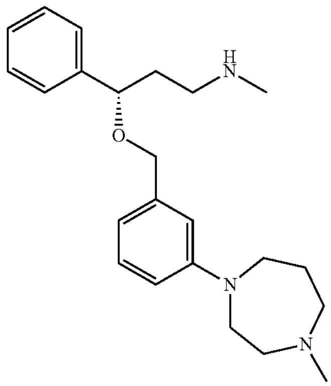 [SMILES: CNCC[C@H](OCc1cccc(N2CCCN(C)CC2)c1)c1ccccc1] | (S)-N-methyl-3-((3-(4-methyl-1,4-diazepan-1-yl)benzyl)oxy)-3-phenylpropan-1-amine | A | 4.74 | 368.2 (M + H) |
| 13 | 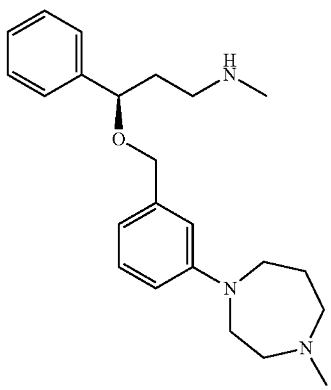 [SMILES: CNCC[C@@H](OCc1cccc(N2CCCN(C)CC2)c1)c1ccccc1] | (R)-N-methyl-3-((3-(4-methyl-1,4-diazepan-1-yl)benzyl)oxy)-3-phenylpropan-1-amine | A | 4.74 | 368.2 (M + H) |

Example 14: (R)-1-methyl-4-(3-((3-(methylamino)-1-(thiophen-2-yl)propoxy) methyl)phenyl)-1,2,3,4-tetrahydro-5H-benzo[e][1,4]diazepin-5-one

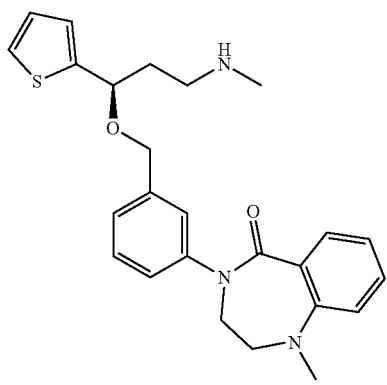 [SMILES: CNCC[C@@H](OCc1cccc(N2CCN(C)c3ccccc3C2=O)c1)c1cccs1]

a) tert-Butyl (R)-methyl(3-((3-(1-methyl-5-oxo-1,2,3,5-tetrahydro-4H-benzo[e][1,4]diazepin-4-yl)benzyl)oxy)-3-(thiophen-2-yl)propyl)carbamate A mixture of CuI (37 mg, 0.19 mmol) and N1,N2-dimethylethane-1,2-diamine (17 mg, 0.19 mmol) in dioxane (0.5 mL) was stirred at rt for 20 min. A solution of tert-butyl (R)-(3-((3-bromobenzyl)oxy)-3-(thiophen-2-yl)propyl) (methyl)carbamate (135 mg, 0.30 mmol) in dioxane (0.5 mL), 1-methyl-1,2,3,4-tetrahydro-5H-benzo[e][1,4]diazepin-5-one (INT 3, 54 mg, 0.30 mmol) and K$_3$PO$_4$ (130 mg, 0.61 mmol) were added and the mixture was heated at 130° C. under Ar atmosphere for 20 h. The reaction mixture was cooled to rt and the solvent was removed under vacuum. Purification by flash chromatography, silica gel, gradient Hex to 100% EtOAc afforded the title compound (104 mg, 63% yield). HPLC (Method B): Ret, 6.07 min; ESP-MS m/z, 536.3 (M+H).

b) Title Compound

In a round-bottom flask, ZnBr$_2$ (210 mg, 0.93 mmol) was dried under vacuum at 200° C. for 3 h. Once the solid reached rt, a solution of the compound prepared in step a (100 mg, 0.18 mmol) in DCM (9 mL) was added and the mixture was stirred at rt under Ar atmosphere for 20 h. Water was added and the mixture was stirred for 45 min. The layers were decanted and the aq layer was extracted with DCM. The organic layer was washed with NaHCO$_3$ sat solution and brine, dried with Na$_2$SO$_4$ and the solvent was removed under vacuum to afford the title compound (78 mg, 96% yield). HPLC (Method A): Ret, 6.10 min: ESI$^+$-HRMS m/z, 436.2 (M+H).

This method was used for the preparation of Ex 15-87 using suitable starting materials:

| EX | Structure | Chemical name | Method | Ret (min) | MS |
|---|---|---|---|---|---|
| 15 | 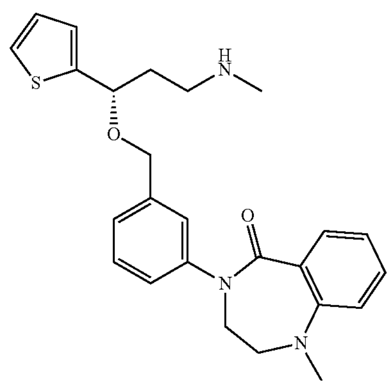 [SMILES: CNCC[C@H](OCc1cccc(N2CCN(C)c3ccccc3C2=O)c1)c1cccs1] | (S)-1-methyl-4-(3-(((3-(methylamino)-1-(thiophen-2-yl)propoxy)methyl)phenyl)-1,2,3,4-tetrahydro-5H-benzo[e][1,4]diazepin-5-one | A | 6.10 | 436.2 (M + H) |
| 16 | 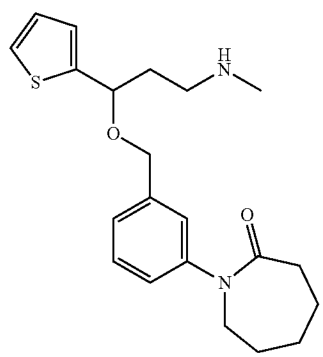 [SMILES: CNCCC(OCc1cccc(N2CCCCCC2=O)c1)c1cccs1] | 1-(3-(((3-(Methylamino)-1-(thiophen-2-yl)propoxy)methyl)phenyl)azepan-2-one | A | 5.64 | 373.1 (M + H) |
| 17 | 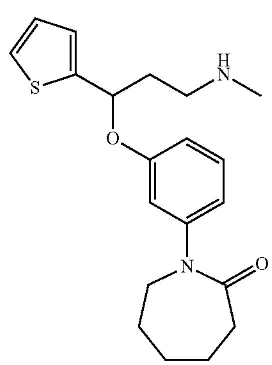 [SMILES: CNCCC(Oc1cccc(N2CCCCCC2=O)c1)c1cccs1] | 1-(3-(3-(Methylamino)-1-(thiophen-2-yl)propoxy)phenyl)azepan-2-one | A | 5.43 | 359.1 (M + H) |
| 18 | 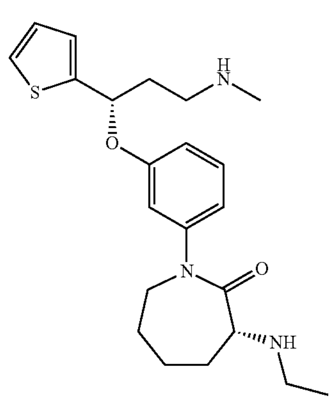 [SMILES: CCN[C@@H]1CCCCN(c2cccc(O[C@@H](CCNC)c3cccs3)c2)C1=O] | (R)-3-(ethylamino)-1-(3-((S)-3-(methylamino)-1-(thiophen-2-yl)propoxy)phenyl)azepan-2-one | A | 4.54 | 402.2 (M + H) |

-continued

| EX | Structure | Chemical name | Method | Ret (min) | MS |
|---|---|---|---|---|---|
| 19 | 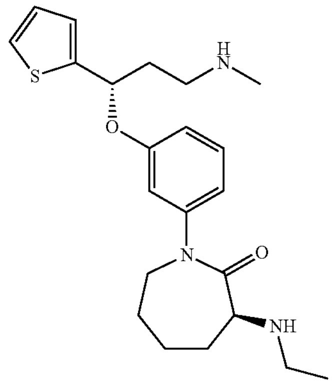 [SMILES: CCN[C@H]1CCCCN(c2cccc(O[C@@H](CCNC)c3cccs3)c2)C1=O] | (S)-3-(ethylamino)-1-(3-((S)-3-(methylamino)-1-(thiophen-2-yl)propoxy)phenyl)azepan-2-one | A | 4.55 | 402.2 (M + H) |
| 20 | 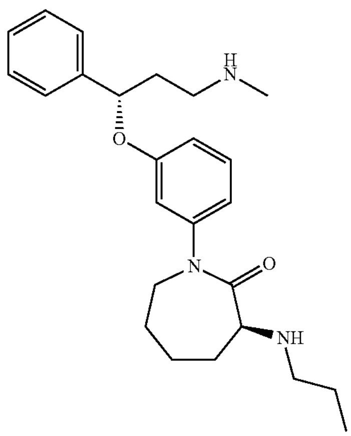 [SMILES: CCCN[C@H]1CCCCN(c2cccc(O[C@@H](CCNC)c3ccccc3)c2)C1=O] | (R)-3-((ethylamino)methyl)-1-(3-((S)-3-(methylamino)-1-phenylpropoxy)phenyl)azepan-2-one | A | 4.73 | 410.2 (M + H) |
| 21 | 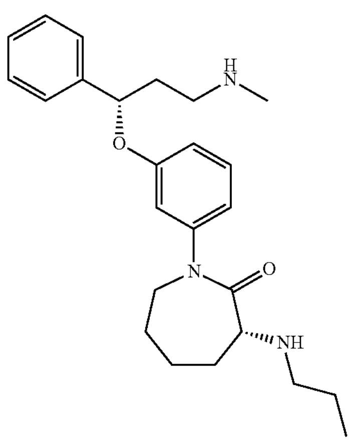 [SMILES: CCCN[C@@H]1CCCCN(c2cccc(O[C@@H](CCNC)c3ccccc3)c2)C1=O] | (S)-3-((ethylamino)methyl)-1-(3-((S)-3-(methylamino)-1-phenylpropoxy)phenyl)azepan-2-one | A | 4.73 | 410.2 (M + H) |

-continued

| EX | Structure | Chemical name | Method | Ret (min) | MS |
|----|-----------|---------------|--------|-----------|-----|
| 22 | 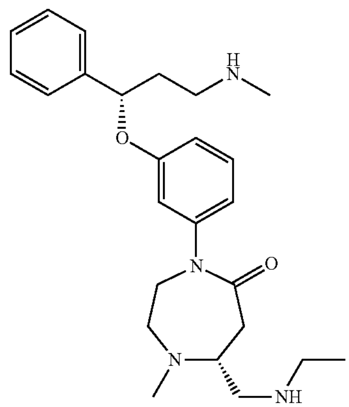 [SMILES: CCNC[C@H]1CC(=O)N(c2cccc(O[C@@H](CCNC)c3ccccc3)c2)CCN1C] | (R)-7-((ethylamino)methyl)-1-methyl-4-(3-((S)-3-(methylamino)-1-phenylpropoxy)phenyl)-1,4-diazepan-5-one | A | 4.26 | 425.2 (M + H) |
| 23 | 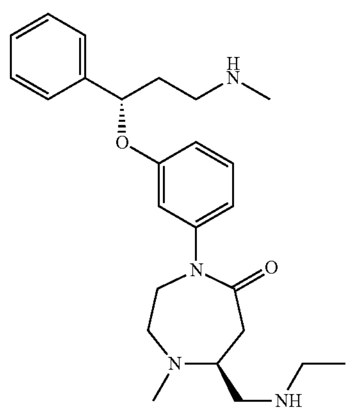 [SMILES: CCNC[C@@H]1CC(=O)N(c2cccc(O[C@@H](CCNC)c3ccccc3)c2)CCN1C] | (S)-7-((ethylamino)methyl)-1-methyl-4-(3-((S)-3-(methylamino)-1-phenylpropoxy)phenyl)-1,4-diazepan-5-one | A | 4.26 | 425.2 (M + H) |
| 24 | 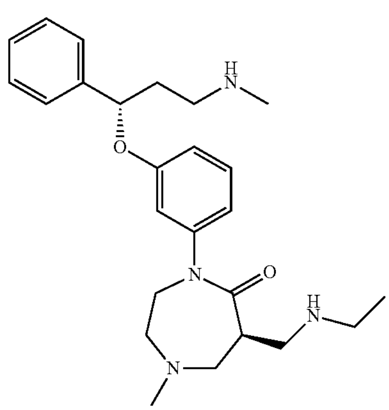 [SMILES: CCNC[C@H]1CN(C)CCN(c2cccc(O[C@@H](CCNC)c3ccccc3)c2)C1=O] | (S)-6-((ethylamino)methyl)-1-methyl-4-(3-((S)-3-(methylamino)-1-phenylpropoxy)phenyl)-1,4-diazepan-5-one | A | 3.95 | 425.2 (M + H) |

| EX | Structure | Chemical name | Method | Ret (min) | MS |
|---|---|---|---|---|---|
| 25 | 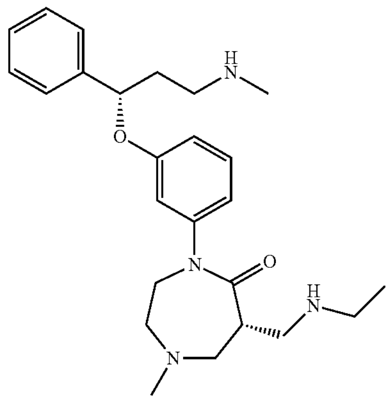 [SMILES: CCNC[C@@H]1CN(C)CCN(c2cccc(O[C@@H](CCNC)c3ccccc3)c2)C1=O] | (R)-6-((ethylamino)methyl)-1-methyl-4-(3-((S)-3-(methylamino)-1-phenylpropoxy)phenyl)-1,4-diazepan-5-one | A | 3.93 | 425.3 (M + H) |
| 26 | 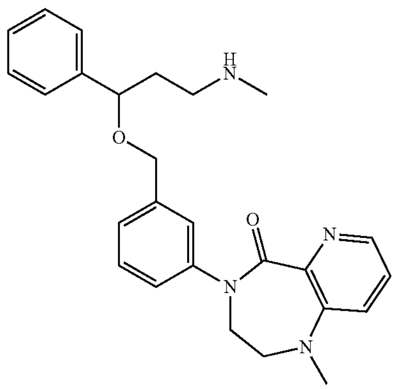 [SMILES: CNCCC(OCc1cccc(N2CCN(C)c3cccnc3C2=O)c1)c1ccccc1] | 1-Methyl-4-(3-((3-(methylamino)-1-phenylpropoxy)methyl)phenyl)-1,2,3,4-tetrahydro-5H-pyrido[3,2-e][1,4]diazepin-5-one | A | 4.80 | 431.2 (M + H) |
| 27 | 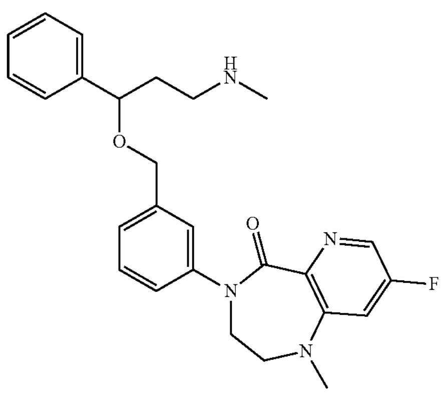 [SMILES: CNCCC(OCc1cccc(N2CCN(C)c3cc(F)cnc3C2=O)c1)c1ccccc1] | 8-Fluoro-1-methyl-4-(3-((3-(methylamino)-1-phenylpropoxy)methyl)phenyl)-1,2,3,4-tetrahydro-5H-pyrido[3,2-e][1,4]diazepin-5-one | A | 5.69 | 449.2 (M + H) |
| 28 | 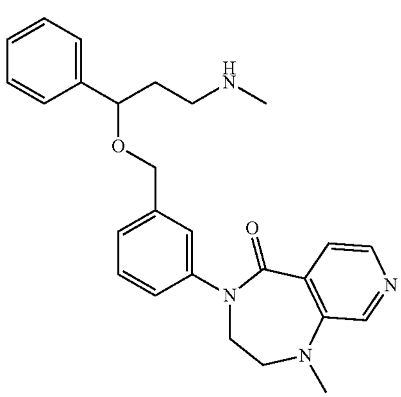 [SMILES: CNCCC(OCc1cccc(N2CCN(C)c3cnccc3C2=O)c1)c1ccccc1] | 1-Methyl-4-(3-((3-(methylamino)-1-phenylpropoxy)methyl)phenyl)-1,2,3,4-tetrahydro-5H-pyrido[3,4-e][1,4]diazepin-5-one | A | 4.80 | 431.2 (M + H) |

-continued

| EX | Structure | Chemical name | Method | Ret (min) | MS |
|---|---|---|---|---|---|
| 29 | 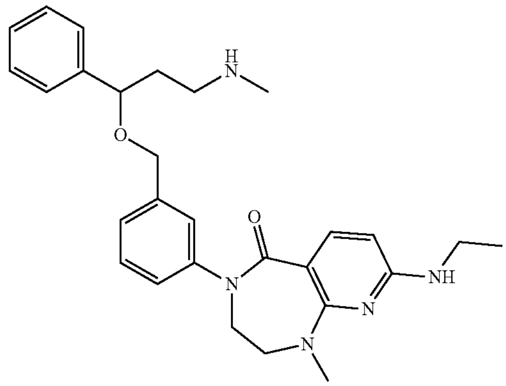 [SMILES: CCNc1ccc2c(n1)N(C)CCN(c1cccc(COC(CCNC)c3ccccc3)c1)C2=O] | 8-(Ethylamino)-1-methyl-4-(3-((3-(methylamino)-1-phenylpropoxy)methyl)phenyl)-1,2,3,4-tetrahydro-5H-pyrido[2,3-e][1,4]diazepin-5-one | A | 5.07 | 474.3 (M + H) |
| 30 | 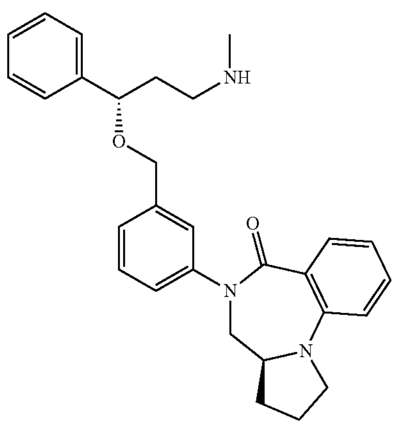 [SMILES: CNCC[C@H](OCc1cccc(N2C[C@@H]3CCCN3c3ccccc3C2=O)c1)c1ccccc1] | (S)-5-(3-(((S)-3-(methylamino)-1-phenylpropoxy)methyl)phenyl)-1,2,3,3a,4,5-hexahydro-6H-benzo[f]pyrrolo[1,2-a][1,4]diazepin-6-one | A | 6.63 | 456.3 (M + H) |
| 31 | 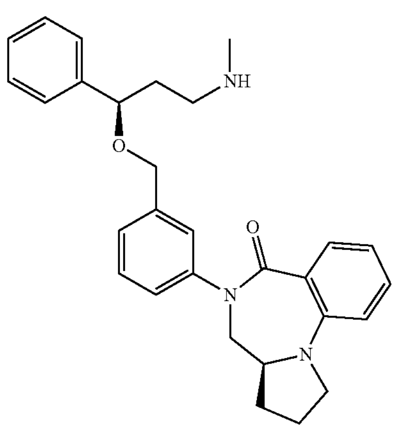 [SMILES: CNCC[C@@H](OCc1cccc(N2C[C@@H]3CCCN3c3ccccc3C2=O)c1)c1ccccc1] | (S)-5-(3-(((R)-3-(methylamino)-1-phenylpropoxy)methyl)phenyl)-1,2,3,3a,4,5-hexahydro-6H-benzo[f]pyrrolo[1,2-a][1,4]diazepin-6-one | A | 6.63 | 456.3 (M + H) |

-continued
| EX | Structure | Chemical name | Method | Ret (min) | MS |
|---|---|---|---|---|---|
| 32 | 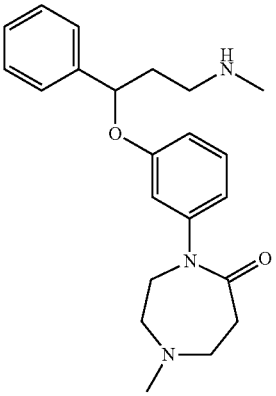 [SMILES: CNCCC(Oc1cccc(N2CCN(C)CCC2=O)c1)c1ccccc1] | 1-Methyl-4-(3-(3-(methylamino)-1-phenylpropoxy)phenyl)-1,4-diazepan-5-one | A | 4.19 | |
| 33 | 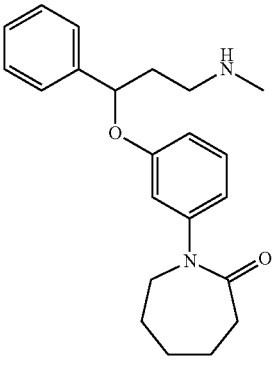 [SMILES: CNCCC(Oc1cccc(N2CCCCCC2=O)c1)c1ccccc1] | 1-(3-(3-(Methylamino)-1-phenylpropoxy)phenyl)azapan-2-one | A | 5.60 | 353.2 (M + H) |
| 34 | 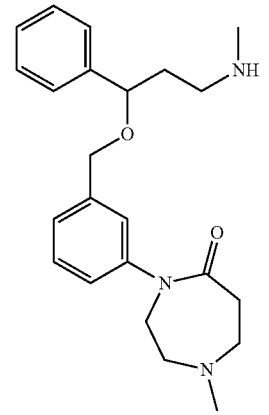 [SMILES: CNCCC(OCc1cccc(N2CCN(C)CCC2=O)c1)c1ccccc1] | 1-Methyl-4-(3-((3-(methylamino)-1-phenylpropoxy)methyl)phenyl)-1,4-diazepan-5-one | A | 4.33 | 382.2 (M + H) |
| 35 | 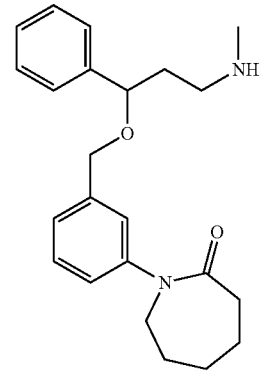 [SMILES: CNCCC(OCc1cccc(N2CCCCCC2=O)c1)c1ccccc1] | 1-(3-((3-(Methylamino)-1-phenylpropoxy)methyl)phenyl)azepan-2-one | A | 5.79 | 367.2 (M + H) |

-continued
| EX | Structure | Chemical name | Method | Ret (min) | MS |
|----|-----------|---------------|--------|-----------|-----|
| 36 | 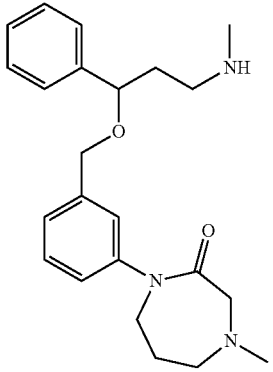 [SMILES: CNCCC(OCc1cccc(N2CCCN(C)CC2=O)c1)c1ccccc1] | 4-Methyl-1-(3-((3-(methylamino)-1-phenylpropoxy)methyl)phenyl)-1,4-diazepan-2-one | A | 4.37 | 382.2 (M + H) |
| 37 | 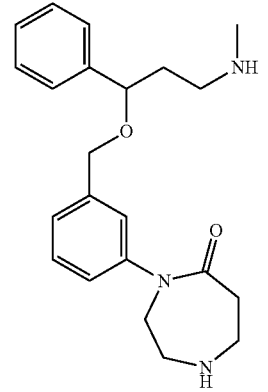 [SMILES: CNCCC(OCc1cccc(N2CCNCCC2=O)c1)c1ccccc1] | 4-(3-((3-(Methylamino)-1-phenylpropoxy)methyl)phenyl)-1,4-diazepan-5-one | A | 4.29 | 368.2 (M + H) |
| 38 | 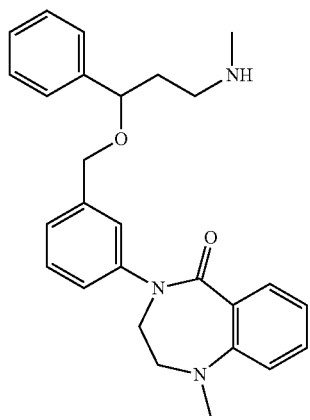 [SMILES: CNCCC(OCc1cccc(N2CCN(C)c3ccccc3C2=O)c1)c1ccccc1] | 1-Methyl-4-(3-((3-(methylamino)-1-phenylpropoxy)methyl)phenyl)-1,2,3,4-tetrahydro-5H-benzo[e][1,4]diazepin-5-one | A | 6.22 | 430.2 (M + H) |

| EX | Structure | Chemical name | Method | Ret (min) | MS |
|----|-----------|---------------|--------|-----------|-----|
| 39 | 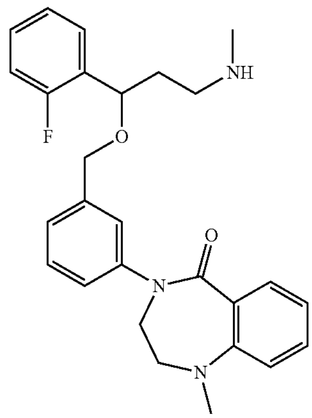 [SMILES: CNCCC(OCc1cccc(N2CCN(C)c3ccccc3C2=O)c1)c1ccccc1F] | 4-(3-((1-(2-Fluorophenyl)-3-(methylamino)propoxy)methyl)phenyl)-1-methyl-1,2,3,4-tetrahydro-5H-benzo[e][1,4]diazepin-5-one | A | 6.24 | 448.2 (M + H) |
| 40 | 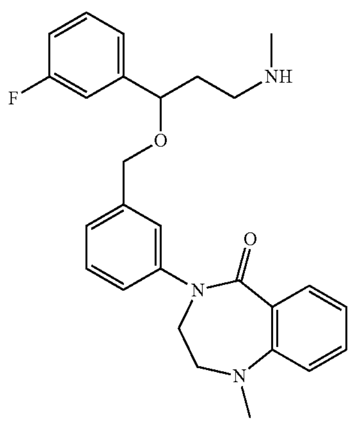 [SMILES: CNCCC(OCc1cccc(N2CCN(C)c3ccccc3C2=O)c1)c1cccc(F)c1] | 4-(3-((1-(3-Fluorophenyl)-3-(methylamino)propoxy)methyl)phenyl)-1-methyl-1,2,3,4-tetrahydro-5H-benzo[e][1,4]diazepin-5-one | A | 6.30 | 448.2 (M + H) |
| 41 | 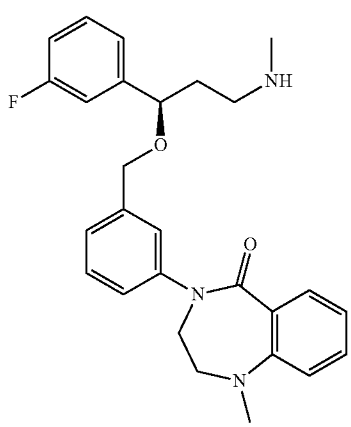 [SMILES: CNCC[C@@H](OCc1cccc(N2CCN(C)c3ccccc3C2=O)c1)c1cccc(F)c1] | (R)-4-(3-((1-(3-fluorophenyl)-3-(methylamino)propoxy)methyl)phenyl)-1-methyl-1,2,3,4-tetrahydro-5H-benzo[e][1,4]diazepin-5-one | A | 6.30 | 448.2 (M + H) |

| EX | Structure | Chemical name | Method | Ret (min) | MS |
|---|---|---|---|---|---|
| 42 | 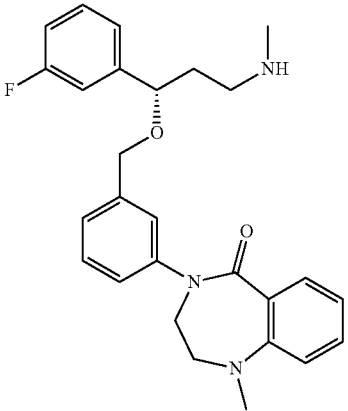 [SMILES: CNCC[C@H](OCc1cccc(N2CCN(C)c3ccccc3C2=O)c1)c1cccc(F)c1] | (S)-4-(3-((1-(3-fluorophenyl)-3-(methylamino)propoxy)methyl)phenyl)methyl-1 2,3,4-tetrahydro-5H-benzo[e][1,4]diazepin-5-one | A | 630 | 448.2 (M + H) |
| 43 | 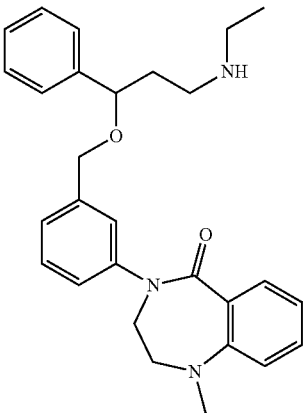 [SMILES: CCNCCC(OCc1cccc(N2CCN(C)c3ccccc3C2=O)c1)c1ccccc1] | 4-(3-((3-(Ethylamino)-1-phenylpropoxy)methyl)phenyl)-1-methyl-1,2,3,4-tetrahydro-5H-benzo[e][1,4]diazepin-5-one | A | 6.32 | 444.2 (M + H) |
| 44 | 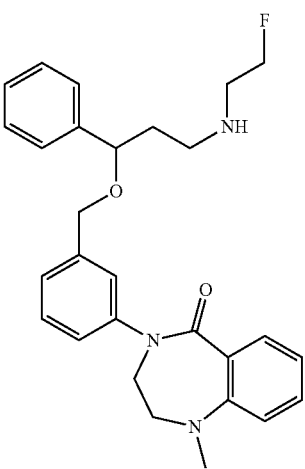 [SMILES: CN1CCN(c2cccc(COC(CCNCCF)c3ccccc3)c2)C(=O)c2ccccc21] | 4-(3-((3-((2-Fluoroethyl)amino)-1-phenylpropoxy)methyl)phenyl)-1-methyl-1,2,3,4-tetrahydro-5H-benzo[e][1,4]diazepin-5-one | A | 6.28 | 462.2 (M + H) |

| EX | Structure | Chemical name | Method | Ret (min) | MS |
|---|---|---|---|---|---|
| 45 | 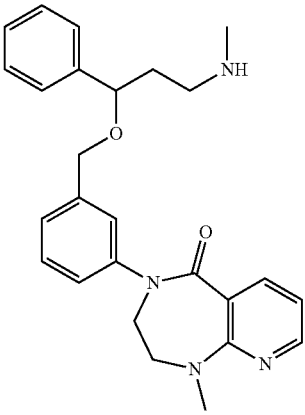 [SMILES: CNCCC(OCc1cccc(N2CCN(C)c3ncccc3C2=O)c1)c1ccccc1] | 1-Methyl-4-(3-((3-(methylamino)-1-phenylpropoxy)methyl)phenyl)-1,2,3,4-tetrahydro-5H-pyrido[2,3-e][1,4]diazepin-5-one | A | 4.77 | 431.3 (M + H) |
| 46 | 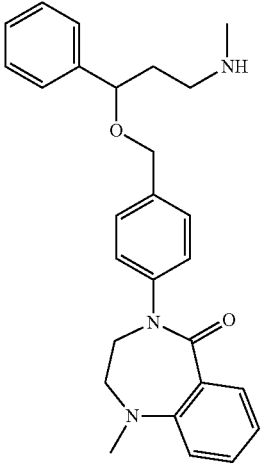 [SMILES: CNCCC(OCc1ccc(N2CCN(C)c3ccccc3C2=O)cc1)c1ccccc1] | 1-Methyl-4-(4-((3-(methylamino)-1-phenylpropoxy)methyl)phenyl)-1,2,3,4-tetrahydro-5H-benzo[e][1,4]diazepin-5-one | A | 6.10 | 430.3 (M + H) |
| 47 | 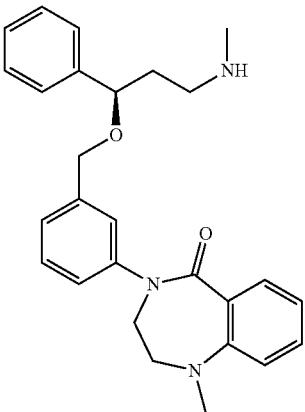 [SMILES: CNCC[C@@H](OCc1cccc(N2CCN(C)c3ccccc3C2=O)c1)c1ccccc1] | (R)-1-methyl-4-(3-((3-(methylamino)-1-phenylpropoxy)methyl)phenyl)-1,2,3,4-tetrahydro-5H-benzo[e][1,4]diazepin-5-one | A | 6.25 | 430.2 (M + H) |

-continued

| EX | Structure | Chemical name | Method | Ret (min) | MS |
|---|---|---|---|---|---|
| 48 | 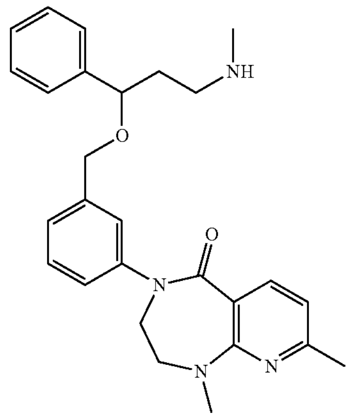 [SMILES: CNCCC(OCc1cccc(N2CCN(C)c3nc(C)ccc3C2=O)c1)c1ccccc1] | 1,8-Dimethyl-4-(3-((3-(methylamino)-1-phenylpropoxy)methyl)phenyl)-1,2,3,4-tetrahydro-5H-pyrido[2,3-e][1,4]diazepin-5-one | A | 4.82 | 445.2 (M + H) |
| 49 | 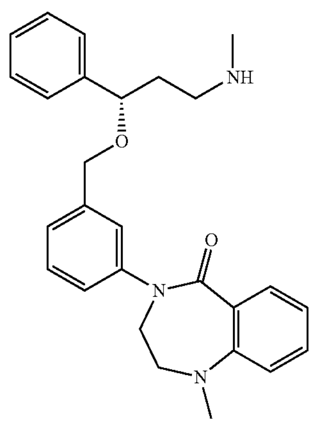 | (S)-1-methyl-4-(3-((3-(methylamino)-1-phenylpropoxy)methyl)phenyl)-1,2,3,4-tetrahydro-5H-benzole)[1,4]diazepin-5-one | A | 6.25 | 430.2 (M + H) |
| 50 | 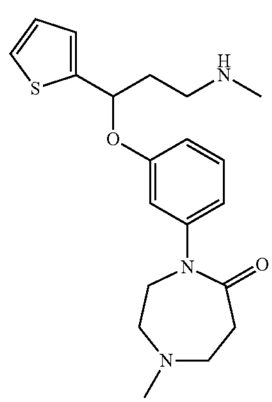 [SMILES: CNCCC(Oc1cccc(N2CCN(C)CCC2=O)c1)c1cccs1] | 1-Methyl-4-(3-(3-(methylamino)-1-(thiophen-2-yl)propoxy)phenyl)-1,4-diazepan-5-one | A | 4.02 | 374.2 (M + H) |

-continued

| EX | Structure | Chemical name | Method | Ret (min) | MS |
|---|---|---|---|---|---|
| 51 | 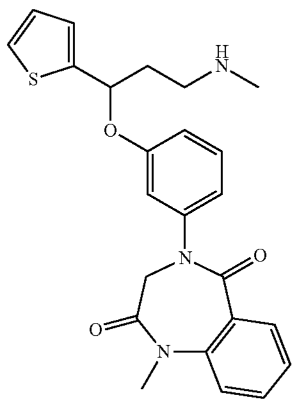 [SMILES: CNCCC(Oc1cccc(N2CC(=O)N(C)c3ccccc3C2=O)c1)c1cccs1] | 1-Methyl-4-(3-(3-(methylamino)-1-(thiophen-2-yl)propoxy)phenyl)-3,4-dihydro-1H-benzo[e][1,4]diazepine-2,5-dione | A | 5.46 | 436.1 (M + H) |
| 52 | 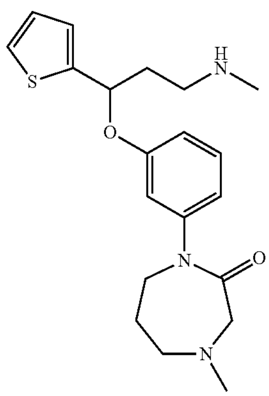 [SMILES: CNCCC(Oc1cccc(N2CCCN(C)CC2=O)c1)c1cccs1] | 4-Methyl-1-(3-(3-(methylamino)-1-(thiophen-2-yl)procoxy)phenyl)-1,4-diazepan-2-one | A | 4.14 | 374.1 (M + H) |
| 53 | 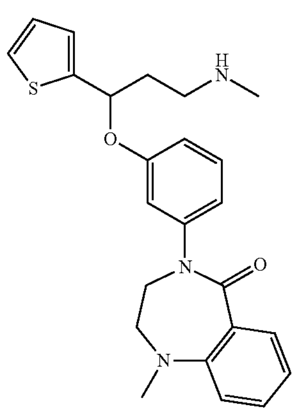 [SMILES: CNCCC(Oc1cccc(N2CCN(C)c3ccccc3C2=O)c1)c1cccs1] | 1-Methyl-4-(3-(3-(methylamino)-1-(thiophen-2-yl)propoxy)phenyl)-1,2,3,4-tetrahydro-5H-benzo[e][1,4]diazepin-5-one | A | 5.96 | 422.2 (M + H) |

-continued

| EX | Structure | Chemical name | Method | Ret (min) | MS |
|---|---|---|---|---|---|
| 54 | 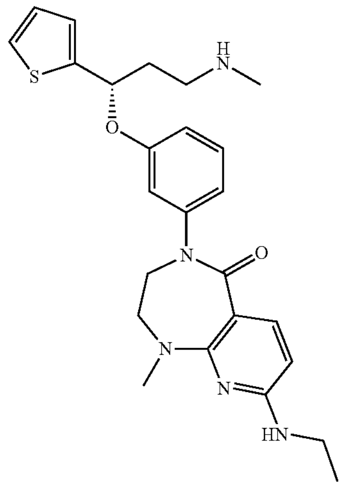 [SMILES: CCNc1ccc2c(n1)N(C)CCN(c1cccc(O[C@@H](CCNC)c3cccs3)c1)C2=O] | (S)-8-(ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one | A | 4.84 | 466.2 (M + H) |
| 55 | 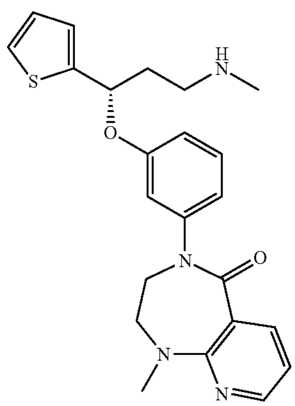 [SMILES: CNCC[C@H](Oc1cccc(N2CCN(C)c3ncccc3C2=O)c1)c1cccs1] | (S)-1-methyl-4-(3-(3-(methylamino)-1-(thiophen-2-yl)propoxy)phenyl)-1,2,3,4-tetrahydro-5H-pyrido[2,3-e][1,4]diazepin-5-one | A | 4.48 | 423.2 (M + H) |
| 56 | 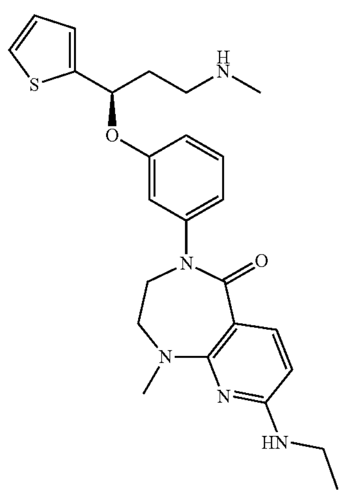 [SMILES: CCNc1ccc2c(n1)N(C)CCN(c1cccc(O[C@H](CCNC)c3cccs3)c1)C2=O] | (R)-8-(ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one | A | 4.84 | 466.2 (M + H) |

| EX | Structure | Chemical name | Method | Ret (min) | MS |
|---|---|---|---|---|---|
| 57 | 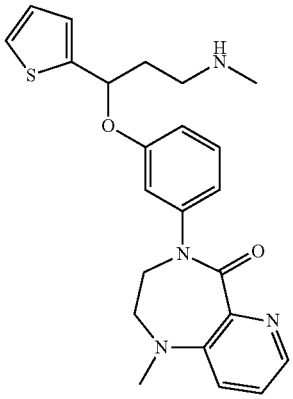 [SMILES: CNCCC(Oc1cccc(N2CCN(C)c3cccnc3C2=O)c1)c1cccs1] | 1-Methyl-4-(3-(3-(methylamino)-1-(thiophen-2-yl)propoxy)phenyl)-1,2,3,4-tetrahydro-5H-pyrido[3,2-e][1,4]diazepin-5-one | A | 4.43 | 423.2 (M + H) |
| 58 | 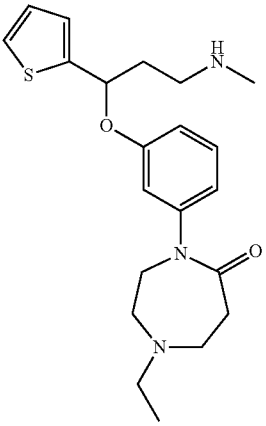 [SMILES: CCN1CCC(=O)N(c2cccc(OC(CCNC)c3cccs3)c2)CC1] | 1-Ethyl-4-(3-(3-(methylamino)-1-(thiophen-2-yl)propoxy)phenyl)-1,4-diazepan-5-one | A | 4.11 | 388.2 (M + H) |
| 59 | 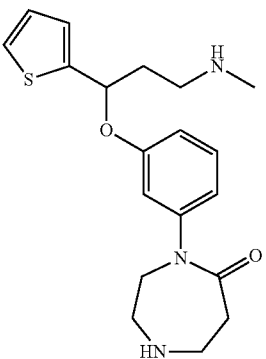 [SMILES: CNCCC(Oc1cccc(N2CCNCCC2=O)c1)c1cccs1] | 4-(3-(3-(Methylamino)-1-(thiophen-2-yl)propoxy)phenyl)-1,4-diazepan-5-one | A | 3.99 | 360.2 (M + H) |

-continued

| EX | Structure | Chemical name | Method | Ret (min) | MS |
|---|---|---|---|---|---|
| 60 | 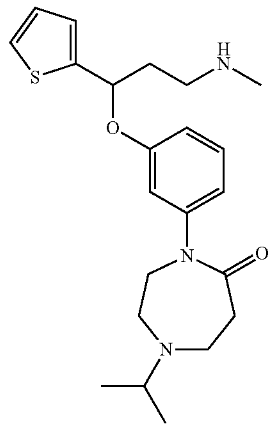 [SMILES: CNCCC(Oc1cccc(N2CCN(C(C)C)CCC2=O)c1)c1cccs1] | 1-Isopropyl-4-(3-(3-(methylamino)-1-(thiophen-2-yl)propoxy)phenyl)-1,4-diazepan-5-one | A | 4.21 | 402.2 (M + H) |
| 61 | 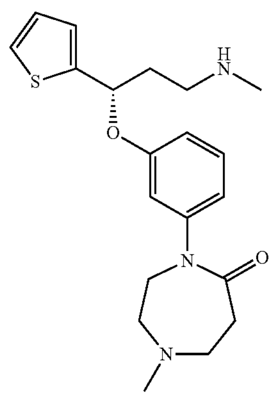 [SMILES: CNCC[C@H](Oc1cccc(N2CCN(C)CCC2=O)c1)c1cccs1] | (S)-1-methyl-4-(3-(3-(methylamino)-1-(thiophen-2-yl)propoxy)phenyl)-1,4-diazepan-5-one | A | 4.07 | 374.2 (M + H) |
| 62 | 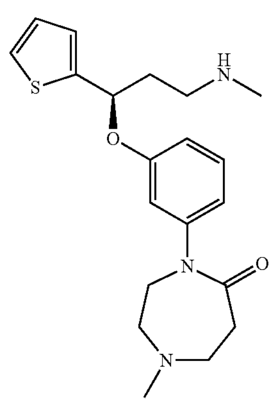 [SMILES: CNCC[C@@H](Oc1cccc(N2CCN(C)CCC2=O)c1)c1cccs1] | (R)-1-methyl-4-(3-(3-(methylamino)-1-(thiophen-2-yl)propoxy)phenyl)-1,4-diazepan-5-one | A | 4.07 | 374.2 (M + H) |

-continued

| EX | Structure | Chemical name | Method | Ret (min) | MS |
|---|---|---|---|---|---|
| 63 | 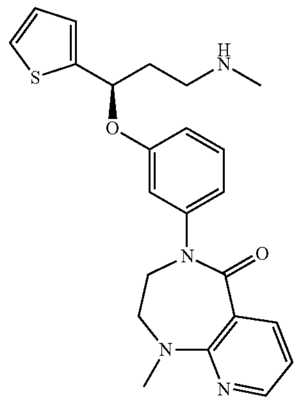 [SMILES: CNCC[C@@H](Oc1cccc(N2CCN(C)c3ncccc3C2=O)c1)c1cccs1] | (R)-1-methyl-4-(3-(3-(methylamino)-1-(thiophen-2-yl)propoxy)phenyl)-1,2,3,4-tetrahydro-5H-pyrido[2,3-e][1,4]diazepin-5-one | A | 4.49 | 423.2 (M + H) |
| 64 | 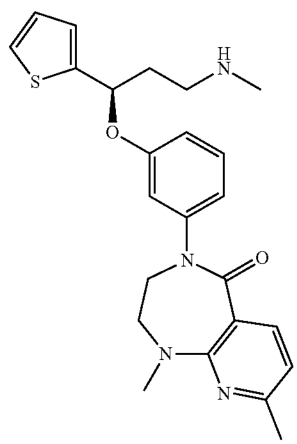 [SMILES: CNCC[C@@H](Oc1cccc(N2CCN(C)c3nc(C)ccc3C2=O)c1)c1cccs1] | (R)-1,8-dimethyl-4-(3-(3-(methylamino)-1-(thiophen-2-yl)propoxy)phenyl)-1,2,3,4-tetrahydro-5H-pyrido[2,3-e][1,4]diazepin-5-one | A | 4.59 | 437.2 (M + H) |
| 65 | 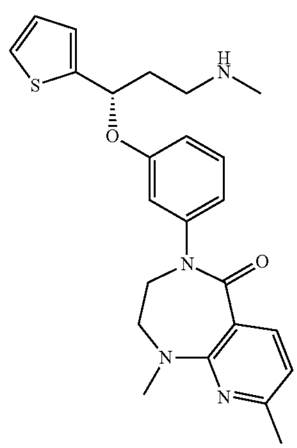 [SMILES: CNCC[C@H](Oc1cccc(N2CCN(C)c3nc(C)ccc3C2=O)c1)c1cccs1] | (S)-1,8-dimethyl-4-(3-(3-(methylamino)-1-(thiophen-2-yl)propoxy)phenyl)-1,2,3,4-tetrahydro-5H-pyrido[2,3-e][1,4]diazepin-5-one | A | 4.59 | 437.2 (M + H) |

| EX | Chemical name | Method | Ret (min) | MS |
|---|---|---|---|---|
| 66 | (S)-1-isopropyl-4-(3-(3-(methylamino)-1-(thiophen-2-yl)propoxy)phenyl)-1,4-diazepan-5-one | A | 4.21 | 402.2 (M + H) |
| 67 | (R)-1-isopropyl-4-(3-(3-(methylamino)-1-(thiophen-2-yl)propoxy)phenyl)-1,4-diazepan-5-one | A | 4.21 | 402.2 (M + H) |
| 68 | 1-(Ethylglycyl)-4-(3-(3-(methylamino)-1-(thiophen-2-yl)propoxy)phenyl)-1,4-diazepan-5-one | A | 4.19 | 445.2 (M + H) |

-continued

| EX | Structure | Chemical name | Method | Ret (min) | MS |
|---|---|---|---|---|---|
| 69 | 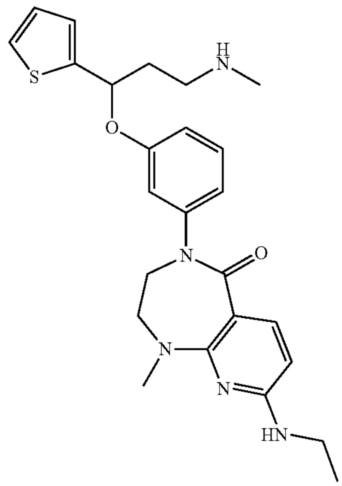 [SMILES: CCNc1ccc2c(n1)N(C)CCN(c1cccc(OC(CCNC)c3cccs3)c1)C2=O] | 8-(Ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one | A | 4.84 | 466.3 (M + H) |
| 70 | 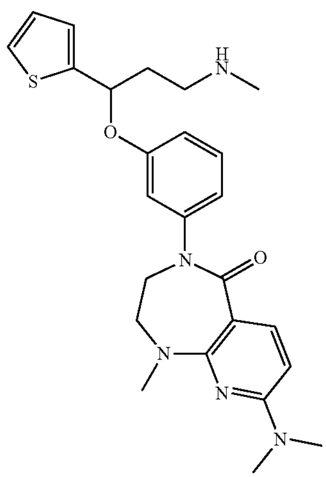 [SMILES: CNCCC(Oc1cccc(N2CCN(C)c3nc(N(C)C)ccc3C2=O)c1)c1cccs1] | 8-(Dimethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one | A | 5.91 | 466.2 (M + H) |
| 71 | 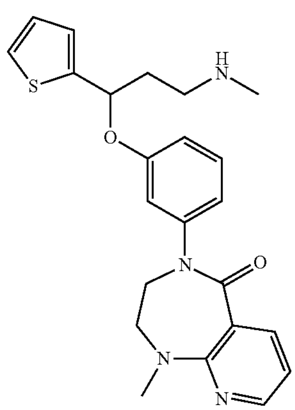 [SMILES: CNCCC(Oc1cccc(N2CCN(C)c3ncccc3C2=O)c1)c1cccs1] | 1-Methyl-4-(3-(3-(methylamino)-1-(thiophen-2-yl)propoxy)phenyl)-1,2,3,4-tetrahydro-5H-pyrido[2,3-e][1,4]diazepin-5-one | A | 4.48 | 423.2 (M + H) |

-continued

| EX | Structure | Chemical name | Method | Ret (min) | MS |
|---|---|---|---|---|---|
| 72 | 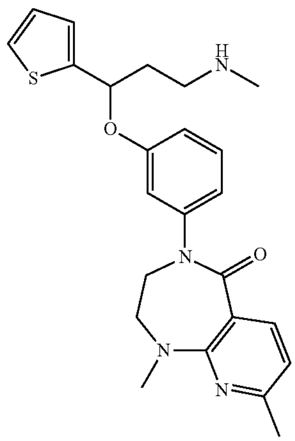 [SMILES: CNCCC(Oc1cccc(N2CCN(C)c3nc(C)ccc3C2=O)c1)c1cccs1] | 1,8-Dimethyl-4-(3-(3-(methylamino)-1-(thiophen-2-yl)propoxy)phenyl)-1,2,3,4-tetrahydro-5H-pyrido[2,3-e][1,4]diazepin-5-one | A | 4.55 | 437.2 (M + H) |
| 73 | 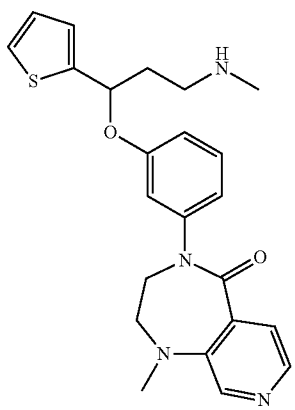 [SMILES: CNCCC(Oc1cccc(N2CCN(C)c3cnccc3C2=O)c1)c1cccs1] | 1-Methyl-4-(3-(3-(methylamino)-1-(thiophen-2-yl)propoxy)phenyl)-1,2,3,4-tetrahydro-5H-pyrido[3,4-e][1,4]diazepin-5-one | A | 4.51 | 423.1 (M + H) |
| 74 | 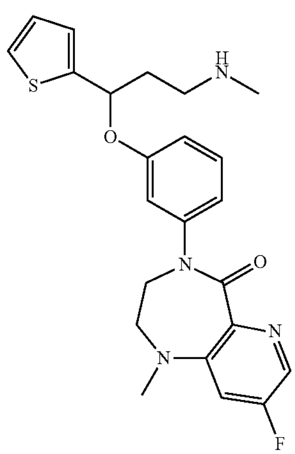 [SMILES: CNCCC(Oc1cccc(N2CCN(C)c3cc(F)cnc3C2=O)c1)c1cccs1] | 8-Fluoro-1-methyl-4-(3-(3-(methylamino)-1-(thiophen-2-yl)propoxy)phenyl)-1,2,3,4-tetrahydro-5H-pyrido[3,2-e][1,4]diazepin-5-one | A | 5.37 | 441.1 (M + H) |

| EX | Structure | Chemical name | Method | Ret (min) | MS |
|---|---|---|---|---|---|
| 75 | 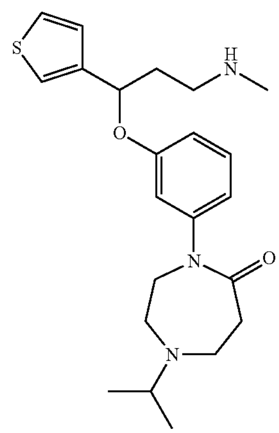 [SMILES: CNCCC(Oc1cccc(N2CCN(C(C)C)CCC2=O)c1)c1ccsc1] | 1-Isopropyl-4-(3-(3-(methylamino)-1-(thiophen-3-yl)propoxy)phenyl)-1,4-diazepan-5-one | A | 4.21 | 402.2 (M + H) |
| 76 | 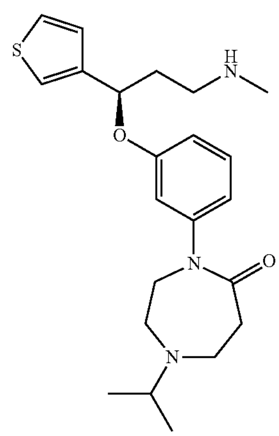 [SMILES: CNCC[C@@H](Oc1cccc(N2CCN(C(C)C)CCC2=O)c1)c1ccsc1] | (R)-1-isopropyl-4-(3-(3-(methylamino)-1-(thiophen-3-yl)propoxy)phenyl)-1,4-diazepan-5-one | A | 4.21 | 402.2 (M + H) |
| 77 | 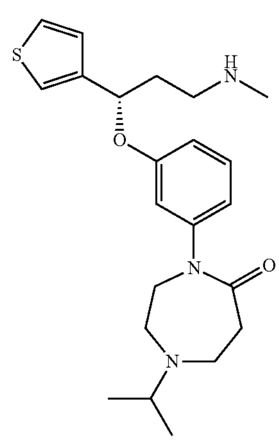 [SMILES: CNCC[C@H](Oc1cccc(N2CCN(C(C)C)CCC2=O)c1)c1ccsc1] | (S)-1-isopropyl-4-(3-(3-(methylamino)-1-(thiophen-3-yl)propoxy)phenyl)-1,4-diazepan-5-one | A | 4.21 | 402.2 (M + H) |

-continued

| EX | Structure | Chemical name | Method | Ret (min) | MS |
|---|---|---|---|---|---|
| 78 | 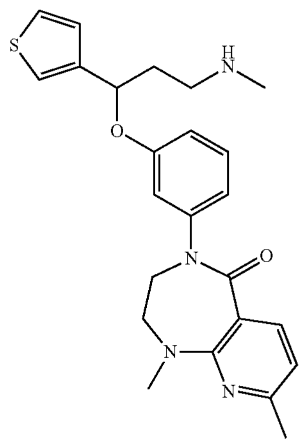 [SMILES: CNCCC(Oc1cccc(N2CCN(C)c3nc(C)ccc3C2=O)c1)c1ccsc1] | 1,8-Dimethyl-4-(3-(3-(methylamino)-1-(thiophen-3-yl)propoxy)phenyl)-1,2,3,4-tetrahydro-5H-pyrido[2,3-e][1,4]diazepin-5-one | A | 4.61 | 437.2 (M + H) |
| 79 | 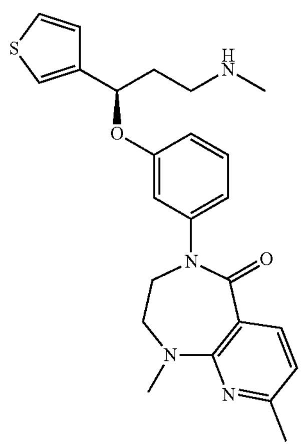 [SMILES: CNCC[C@@H](Oc1cccc(N2CCN(C)c3nc(C)ccc3C2=O)c1)c1ccsc1] | (R)-1,8-dimethyl-4-(3-(3-(methylamino)-1-(thiophen-3-yl)propoxy)phenyl)-1,2,3,4-tetrahydro-5H-pyrido[2,3-e][1,4]diazepin-5-one | A | 4.61 | 437.2 (M + H) |
| 80 | 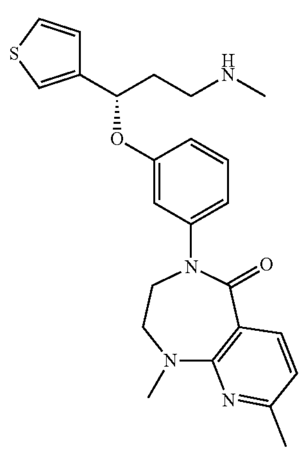 [SMILES: CNCC[C@H](Oc1cccc(N2CCN(C)c3nc(C)ccc3C2=O)c1)c1ccsc1] | (S)-1,8-dimethyl-4-(3-(3-(methylamino)-1-(thiophen-3-yl)propoxy)phenyl)-1,2,3,4-tetrahydro-5H-pyrido[2,3-e][1,4]diazepin-5-one | A | 4.61 | 437.2 (M + H) |

-continued

| EX | Structure | Chemical name | Method | Ret (min) | MS |
|---|---|---|---|---|---|
| 81 | 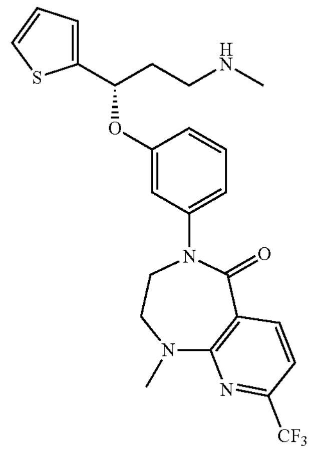 [SMILES: CNCC[C@H](Oc1cccc(N2CCN(C)c3nc(C(F)(F)F)ccc3C2=O)c1)c1cccs1] | (S)-1-methyl-4-(3-(3-(methylamino)-1-(thiophen-2-yl)propoxy)phenyl)-8-(trifluoromethyl)-1,2,3,4-tetrahydro-5H-pyrido[2,3-e][1,4]diazepin-5-one | A | 6.53 | 491.1 (M + H) |
| 82 | 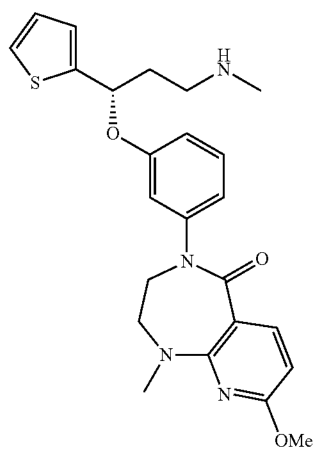 [SMILES: CNCC[C@H](Oc1cccc(N2CCN(C)c3nc(OC)ccc3C2=O)c1)c1cccs1] | (S)-8-methoxy-1-methyl-4-(3-(3-(methylamino)-1-(thiophen-2-yl)propoxy)phenyl)-1,2,3,4-tetrahydro-5H-pyrido[2,3-e][1,4]diazepin-5-one | A | 6.17 | 453.1 (M + H) |
| 83 | 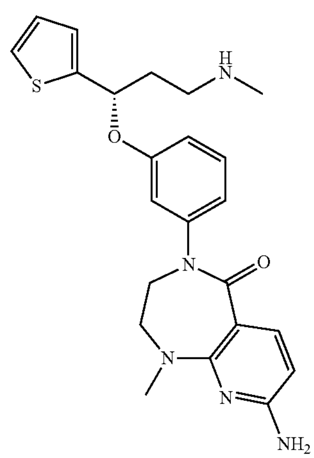 [SMILES: CNCC[C@H](Oc1cccc(N2CCN(C)c3nc(N)ccc3C2=O)c1)c1cccs1] | (S)-8-amino-1-methyl-4-(3-(3-(methylamino)-1-(thiophen-2-yl)propoxy)phenyl)-1,2,3,4-tetrahydro-5H-pyrido[2,3-e][1,4]diazepin-5-one | A | 4.45 | 438.2 (M + H) |

| EX | Structure | Chemical name | Method | Ret (min) | MS |
|---|---|---|---|---|---|
| 84 | 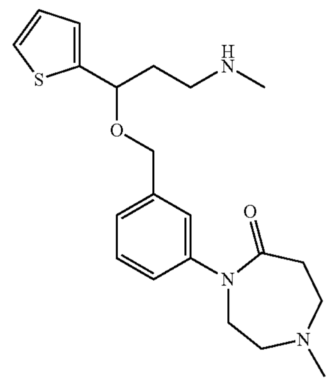 [SMILES: CNCCC(OCc1cccc(N2CCN(C)CCC2=O)c1)c1cccs1] | 1-Methyl-4-(3-((3-(methylamino)-1-(thiophen-2-yl)propoxy)methyl)phenyl)-1,4-diazepan-5-one | A | 4.18 | 388.2 (M + H) |
| 85 | 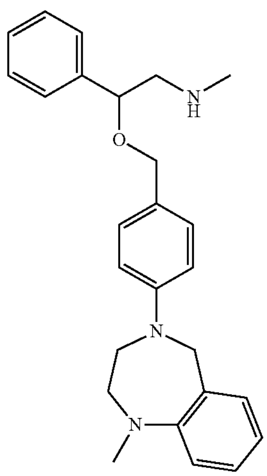 [SMILES: CNCC(OCc1ccc(N2CCN(C)c3ccccc3C2)cc1)c1ccccc1] | 1-Methyl-4-(4-((2-(methylamino)-1-phenylethoxy)methyl)phenyl)-1,2,3,4-tetrahydro-5H-benzo[e][1,4]diazepin-5-one | A | 6.08 | 438.2 (M + Na) |
| 86 | 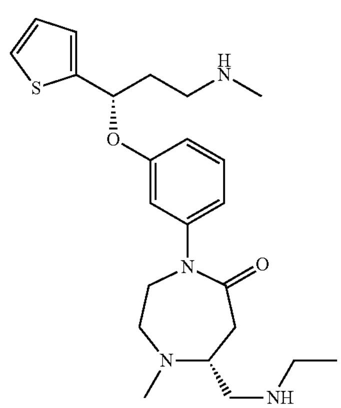 [SMILES: CCNC[C@H]1CC(=O)N(c2cccc(O[C@@H](CCNC)c3cccs3)c2)CCN1C] | (R)-7-((ethylamino)methyl)-1-methyl-4-(3-((S)-3-(methylamino)-1-(thiophen-2-yl)propoxy)phenyl)-1,4-diazepan-5-one | A | 4.15 | 431.3 (M + H) |

| EX | Structure | Chemical name | Method | Ret (min) | MS |
|---|---|---|---|---|---|
| 87 | 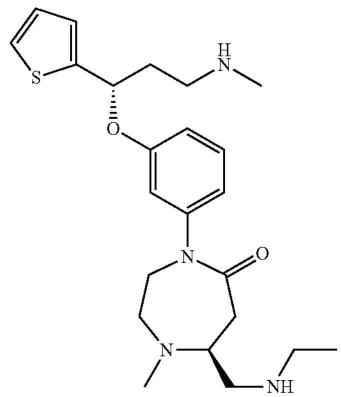 [SMILES: CCNC[C@@H]1CC(=O)N(c2cccc(O[C@@H](CCNC)c3cccs3)c2)CCN1C] | (S)-7-((ethylamino)methyl)-1-methyl-4-(3-((S)-3-(methylamino)-1-(thiophen-2-yl)propoxy)phenyl)-1,4-diazepan-5-one | A | 4.15 | 431.3 (M + H) |

In Ex 50-87 Teoc was used as protecting group.

Example 88: 1-Methyl-4-(4-((3-(methylamino)-1-phenylpropoxy)methyl)benzyl)-1,2,3,4-tetrahydro-5H-benzo[e][1,4]diazepin-5-one

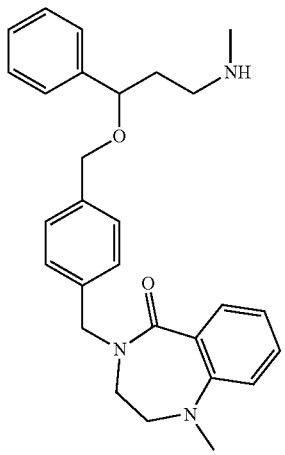 [SMILES: CNCCC(OCc1ccc(CN2CCN(C)c3ccccc3C2=O)cc1)c1ccccc1]

a) tert-Butyl (3-((4-(bromomethyl)benzyl)oxy)-3-phenylpropyl)(methyl)carbamate

To a solution of tert-butyl (3-hydroxy-3-phenylpropyl)(methyl)carbamate (480 mg, 1.81 mmol) in DMF (10 mL) cooled at 0° C., NaH (145 mg, 60% suspension in mineral oil, 3.62 mmol) was added and the mixture was stirred at rt for 30 min. The reaction mixture was added dropwise to a solution of 1,4-bis(bromomethyl)benzene (1.43 g, 5.43 mmol) in DMF (10 mL) and the reaction mixture was stirred at rt for 16 h. Water was added carefully and the mixture extracted with EtOAc. The organic layer was dried with Na$_2$SO$_4$ and the solvent was removed under vacuum. Purification by flash chromatography, silica gel, gradient from Hex to 100% EtOAc, afforded the title compound (165 mg, 20% yield). HPLC (Method B): Ret, 6.54 min; ESI$^+$-MS m/z, 470.1 (M+Na).

b) tert-Butyl methyl(3-((4-((1-methyl-5-oxo-1,2,3,5-tetrahydro-4H-benzo[e][1,4]diazepin-4-yl)methyl)benzyl)oxy)-3-phenylpropyl)carbamate To a solution of 1-methyl-1,2,3,4-tetrahydro-5H-benzo[e][1,4]diazepin-5-one (INT 3, 40 mg, 0.23 mmol) in DMF (1 mL) cooled at 0° C., NaH (60% suspension in mineral oil, 18 mg, 0.45 mmol) was added and the mixture was stirred at rt for 30 min. The reaction mixture was cooled again at 0° C., a solution of the compound prepared in step a (57 mg, 0.12 mmol) in DMF (1 mL) was added and the reaction mixture was stirred at rt for 16 h. Water was added and the mixture was extracted with EtOAc. The organic layer was dried with Na$_2$SO$_4$, filtered and concentrated under vacuum. Purification by flash chromatography, silica gel, gradient from Hex to 100% EtOAc, afforded the title compound (36 mg, 52% yield). HPLC (Method B): Ret, 6.27 min; ESI$^+$-MS m/z, 566.3 (M+Na).

c) Title Compound

The compound prepared in step b was treated with the conditions used in Ex 5 step b to afford the title compound (95% yield). HPLC (Method A): Ret, 6.20 min; ESI$^+$-MS m/z, 444.2 (M+H).

This method was used for the preparation of Ex 89 using suitable starting materials:

| | | | | | |
|---|---|---|---|---|---|
| 89 | 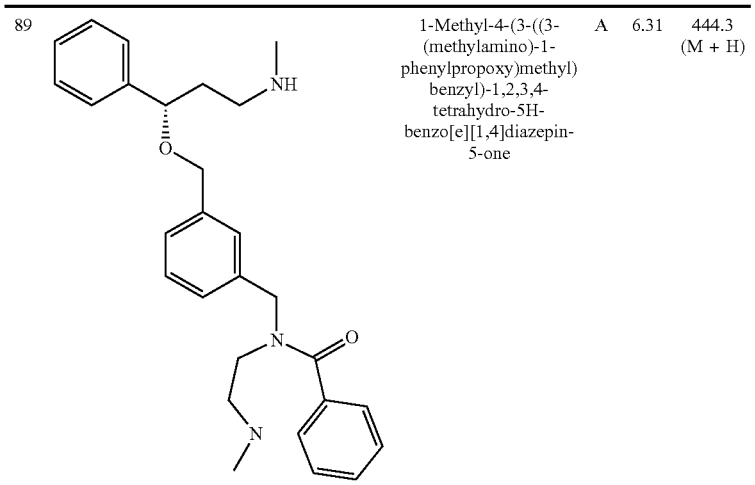 | 1-Methyl-4-(3-((3-(methylamino)-1-phenylpropoxy)methyl)benzyl)-1,2,3,4-tetrahydro-5H-benzo[e][1,4]diazepin-5-one | A | 6.31 | 444.3 (M + H) |

Example 90: (S)-1-methyl-4-(4-(3-(methylamino)-1-(thiophen-2-yl)propoxy)benzyl)-1,2,3,4-tetrahydro-5H-pyrido[2,3-e][1,4]diazepin-5-one

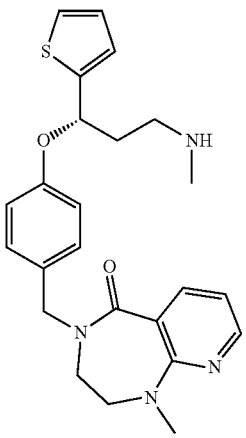 [SMILES: CNCC[C@H](Oc1ccc(CN2CCN(C)c3ncccc3C2=O)cc1)c1cccs1]

a) 2-(Trimethylsilyl)ethyl (S)-methyl(3-(4-((1-methyl-5-oxo-1,2,3,5-tetrahydro-4H-pyrido[2,3-e][1,4]diazepin-4-yl)methyl)phenoxy)-3-(thiophen-2-yl)propyl) carbamate To a solution of 1-methyl-1,2,3,4-tetrahydro-5H-pyrido[2,3-e][1,4]diazepin-5-one (INT 15, 378 mg, 2.13 mmol) in DMF (12 mL) cooled at 0° C., NaH (60% suspension in mineral oil, 116 mg, 2.99 mmol) was added and the mixture was stirred at rt for 30 min. The reaction mixture was cooled again at 0° C. and a solution of 2-(trimethylsilyl)ethyl (S)-(3-(4-(chloromethyl)phenoxy)-3-(thiophen-2-yl)propyl)(methyl) carbamate (1.50 g, 3.41 mmol) in DMF (8 mL) and TBAI (79 mg, 0.21 mmol) were added and the reaction mixture was stirred at rt for 2 h. Water was added, the mixture was extracted with EtOAc and the organic layer was dried with $Na_2SO_4$, filtered and concentrated under vacuum. Purification by flash chromatography, silica gel, gradient from CH to 100% EtOAc afforded the title product (919 mg, 74% yield). HPLC (Method B): Ret, 6.01 min; $ESI^+$-MS m/z, 603.2 (M+Na).

b) Title Compound

The compound obtained in step a was treated with the conditions used in Ex 11 step b to afford the title compound (82% yield). HPLC (Method A): Ret, 4.51 min; $ESI^+$-MS m/z, 437.2 (M+H).

This method was used for the preparation of Ex 91-117 using suitable starting materials:

| | | | | | |
|---|---|---|---|---|---|
| 91 | 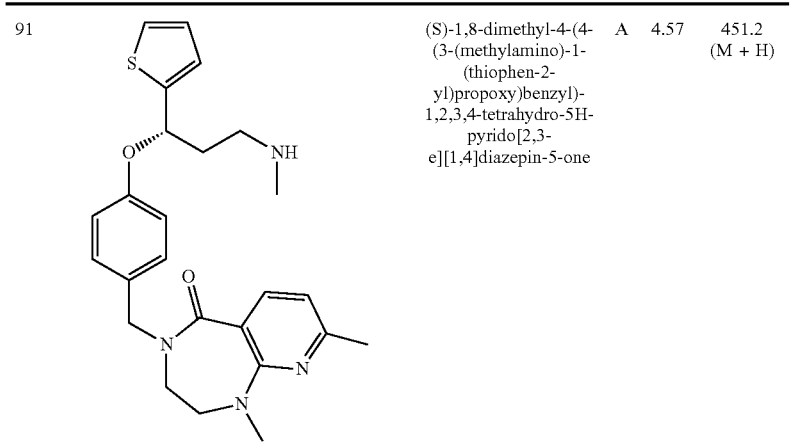 | (S)-1,8-dimethyl-4-(4-(3-(methylamino)-1-(thiophen-2-yl)propoxy)benzyl)-1,2,3,4-tetrahydro-5H-pyrido[2,3-e][1,4]diazepin-5-one | A | 4.57 | 451.2 (M + H) |

-continued
| | | | | | |
|---|---|---|---|---|---|
| 92 | 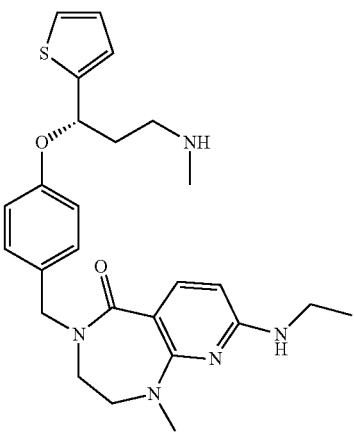 [SMILES: CCNc1ccc2c(n1)N(C)CCN(Cc1ccc(O[C@@H](CCNC)c3cccs3)cc1)C2=O] | (S)-8-(ethylamino)-1-methyl-4-(4-(3-(methylamino)-1-(thiophen-2-yl)propoxy)benzyl)-1,2,3,4-tetrahydro-5H-pyrido[2,3-e][1,4]diazepin-5-one | A | 4.79 | 480.2 (M + H) |
| 93 | 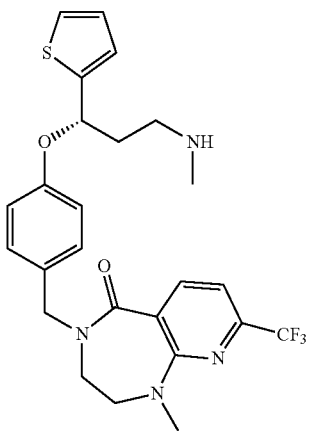 [SMILES: CNCC[C@H](Oc1ccc(CN2CCN(C)c3nc(C(F)(F)F)ccc3C2=O)cc1)c1cccs1] | (S)-1-methyl-4-(4-(3-(methylamino)-1-(thiophen-2-yl)propoxy)benzyl)-8-(trifluoromethyl)-1,2,3,4-tetrahydro-5H-pyrido[2,3-e][1,4]diazepin-5-one | A | 6.55 | 505.1 (M + H) |
| 94 | 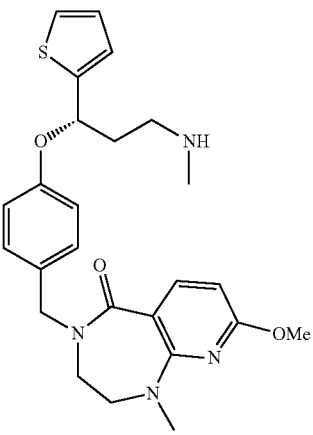 [SMILES: CNCC[C@H](Oc1ccc(CN2CCN(C)c3nc(OC)ccc3C2=O)cc1)c1cccs1] | (S)-8-methoxy-1-methyl-4-(4-(3-(methylamino)-1-(thiophen-2-yl)propoxy)benzyl)-1,2,3,4-tetrahydro-5H-pyrido[2,3-e][1,4]diazepin-5-one | A | 6.09 | 467.2 (M + H) |

| | | | | | |
|---|---|---|---|---|---|
| 95 | 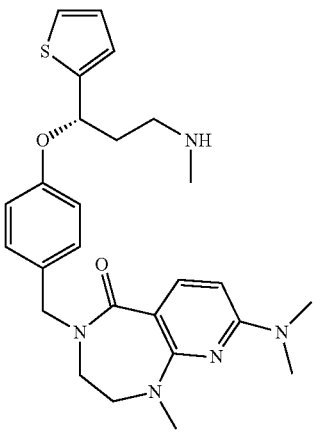 [SMILES: CNCC[C@H](Oc1ccc(CN2CCN(C)c3nc(N(C)C)ccc3C2=O)cc1)c1cccs1] | (S)-8-(dimethylamino)-1-methyl-4-(4-(3-(methylamino)-1-(thiophen-2-yl)propoxy)benzyl)-1,2,3,4-tetrahydro-5H-pyrido[2,3-e][1,4]diazepin-5-one | A | 5.74 | 480.2 (M + H) |
| 96 | 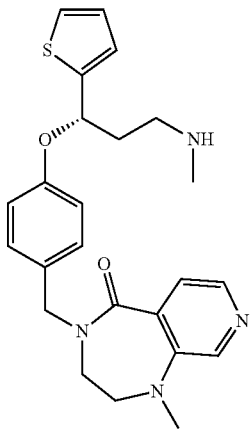 [SMILES: CNCC[C@H](Oc1ccc(CN2CCN(C)c3cnccc3C2=O)cc1)c1cccs1] | (S)-1-methyl-4-(4-(3-(methylamino)-1-(thiophen-2-yl)propoxy)benzyl)-1,2,3,4-tetrahydro-5H-pyrido[3,4-e][1,4]diazepin-5-one | A | 4.49 | 437.1 (M + H) |
| 97 | 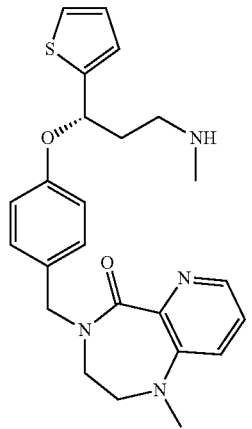 [SMILES: CNCC[C@H](Oc1ccc(CN2CCN(C)c3cccnc3C2=O)cc1)c1cccs1] | (S)-1-methyl-4-(4-(3-(methylamino)-1-(thiophen-2-yl)propoxy)benzyl)-1,2,3,4-tetrahydro-5H-pyrido[3,2-e][1,4]diazepin-6-one | A | 4.50 | 437.2 (M + H) |

| | | | | | |
|---|---|---|---|---|---|
| 98 | 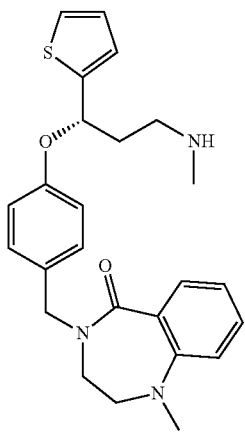 [SMILES: CNCC[C@H](Oc1ccc(CN2CCN(C)c3ccccc3C2=O)cc1)c1cccs1] | (S)-1-methyl-4-(4-(3-(methylamino)-1-(thiophen-2-yl)propoxy)benzyl)-1,2,3,4-tetrahydro-5H-benzo[e][1,4]diazepin-5-one | A | 5.78 | |
| 99 | 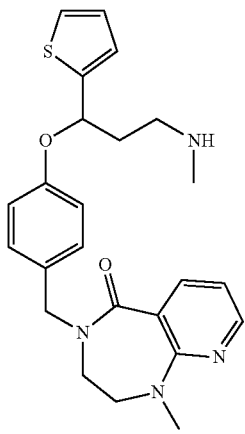 [SMILES: CNCCC(Oc1ccc(CN2CCN(C)c3ncccc3C2=O)cc1)c1cccs1] | 1-Methyl-4-(4-(3-(methylamino)-1-(thiophen-2-yl)propoxy)benzyl)-1,2,3,4-tetrahydro-5H-pyrido[2,3-e][1,4]diazepin-5-one | A | 4.51 | 437.1 (M + H) |
| 100 | 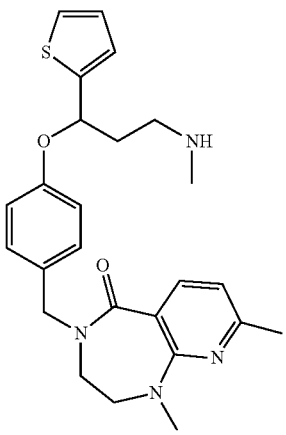 [SMILES: CNCCC(Oc1ccc(CN2CCN(C)c3nc(C)ccc3C2=O)cc1)c1cccs1] | 1,8-Dimethyl-4-(4-(3-(methylamino)-1-(thiophen-2-yl)propoxy)benzyl)-1,2,3,4-tetrahydro-5H-pyrido[2,3-e][1,4]diazepin-5-one | A | 4.57 | 451.2 (M + H) |

| | | | | | |
|---|---|---|---|---|---|
| 101 | 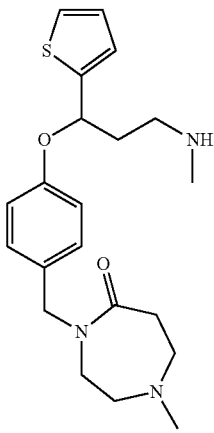 [SMILES: CNCCC(Oc1ccc(CN2CCN(C)CCC2=O)cc1)c1cccs1] | 1-Methyl-4-(4-(3-(methylamino)-1-(thiophen-2-yl)propoxy)benzyl)-1,4-diazepan-5-one | A | 4.14 | 388.2 (M + H) |
| 102 | 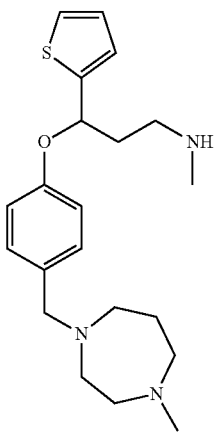 [SMILES: CNCCC(Oc1ccc(CN2CCCN(C)CC2)cc1)c1cccs1] | N-methyl-3-(4-((4-methyl-1,4-diazepan-1-yl)methyl)phenoxy)-3-(thiophen-2-yl)propan-1-amine | A | 3.76 | 374.3 (M + H) |
| 103 | 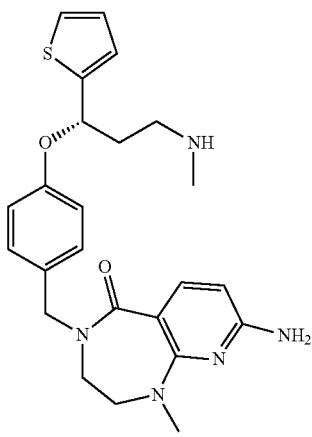 [SMILES: CNCC[C@H](Oc1ccc(CN2CCN(C)c3nc(N)ccc3C2=O)cc1)c1cccs1] | (S)-8-amino-1-methyl-4-(4-(3-(methylamino)-1-(thiophen-2-yl)propoxy)benzyl)-1,2,3,4-tetrahydro-5H-pyrido[2,3-e][1,4]diazepin-5-one | A | 4.49 | 452.2 (M + H) |

| | | | | | |
|---|---|---|---|---|---|
| 104 | 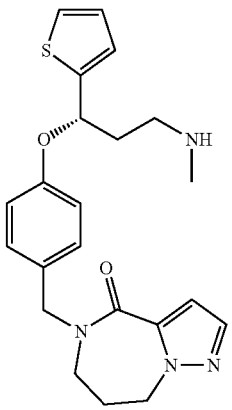 | (S)-5-(4-(3-(methylamino)-1-(thiophen-2-yl)propoxy)benzyl)-5,6,7,8-tetrahydro-4H-pyrazolo[1,5-a][1,4]diazepin-4-one | A | 5.13 | 411.2 (M + H) |
| 105 | 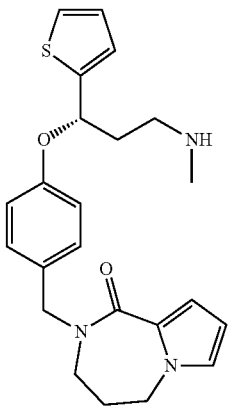 [SMILES: CNCC[C@H](Oc1ccc(CN2CCCn3cccc3C2=O)cc1)c1cccs1] | (S)-2-(4-(3-(methylamino)-1-(thiophen-2-yl)propoxy)benzyl)-2,3,4,5-tetrahydro-1H-pyrrolo[1,2-a][1,4]diazepin-1-one | A | 5.45 | 410.1 (M + H) |
| 106 | 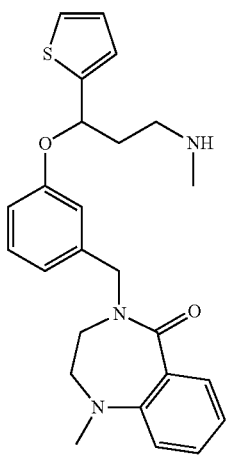 [SMILES: CNCCC(Oc1cccc(CN2CCN(C)c3ccccc3C2=O)c1)c1cccs1] | 1-Methyl-4-(3-(3-(methylamino)-1-(thiophen-yl)propoxy)benzyl)-1,2,3,4-tetrahydro-5H-benzo[e][1,4]diazepin-5-one | A | 5.91 | 436.2 (M + H) |

-continued
| | | | | | |
|---|---|---|---|---|---|
| 107 | 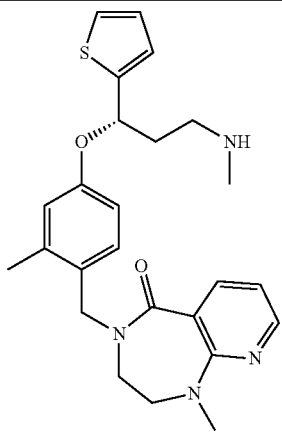 | (S)-1-methyl-4-(2-methyl-4-(3-(methylamino)-1-(thiophen-2-yl)propoxy)benzyl)-1,2,3,4-tetrahydro-5H-pyrido[2,3-e][1,4]diazepin-5-one | A | 4.65 | 451.2 (M + H) |
| 108 | 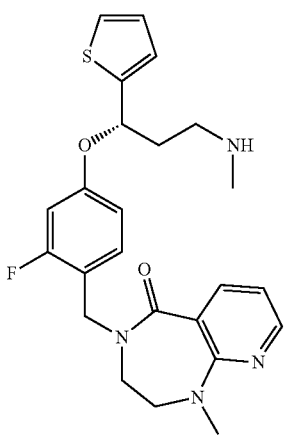 | (S)-4-(2-fluoro-4-(3-(methylamino)-1-(thiophen-2-yl)propoxy)benzyl)-1-methyl-1,2,3,4-tetrahydro-5H-pyrido[2,3-e)[1,4]diazepin-5-one | A | 4.54 | 455.1 (M + H) |
| 109 | 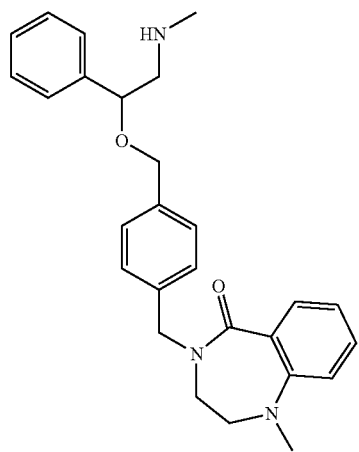 [SMILES: CNCC(OCc1ccc(CN2CCN(C)c3ccccc3C2=O)cc1)c1ccccc1] | 1-Methyl-4-(4-((2-(methylamino)-1-phenylethoxy)methyl)benzyl)-1,2,3,4-tetrahydro-5H-benzo[e][1,4]diazepin-5-one | A | 6.09 | 452.3 (M + Na) |

-continued
| | | | | | |
|---|---|---|---|---|---|
| 110 | 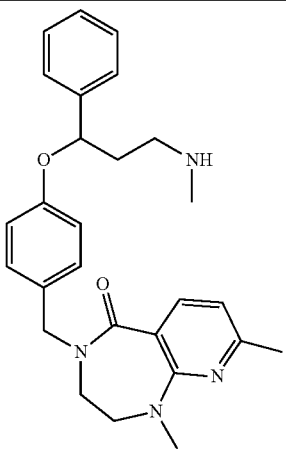 | 1,8-Dimethyl-4-(4-(3-(methylamino)-1-phenylpropoxy)benzyl)-1,2,3,4-tetrahydro-5H-pyrido[2,3-e][1,4]diazepin-5-one | A | 4.72 | 445.3 (M + H) |
| 111 | 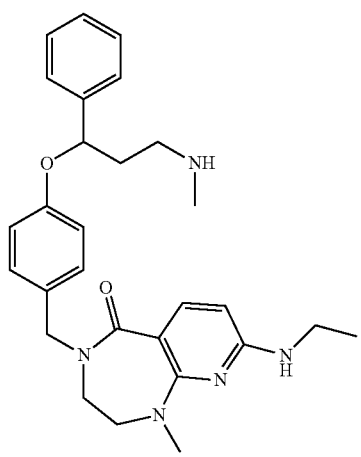 [SMILES: CCNc1ccc2c(n1)N(C)CCN(Cc1ccc(OC(CCNC)c3ccccc3)cc1)C2=O] | 8-(Ethylamino)-1-methyl-4-(4-(3-(methylamino)-1-phenylpropoxy)benzyl)-1,2,3,4-tetrahydro-5H-pyrido[2,3-e][1,4]diazepin-5-one | A | 4.86 | 474.3 (M + H) |
| 112 | 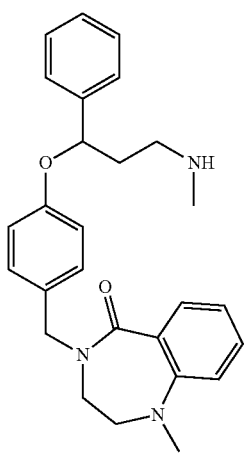 [SMILES: CNCCC(Oc1ccc(CN2CCN(C)c3ccccc3C2=O)cc1)c1ccccc1] | 1-Methyl-4-(4-(3-(methylamino)-1-phenylpropoxy)benzyl)-1,2,3,4-tetrahydro-5H-benzo[e][1,4]diazepin-5-one | A | 5.98 | 430.2 (M + H) |

| | | | | | |
|---|---|---|---|---|---|
| 113 | 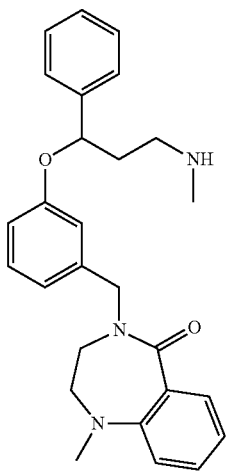 [SMILES: CNCCC(Oc1cccc(CN2CCN(C)c3ccccc3C2=O)c1)c1ccccc1] | 1-Methyl-4-(3-(3-(methylamino)-1-phenylpropoxy)benzyl)-1,2,3,4-tetrahydro-5H-benzo[e][1,4]diazepin-5-one | A | 6.02 | 430.2 (M + H) |
| 114 | 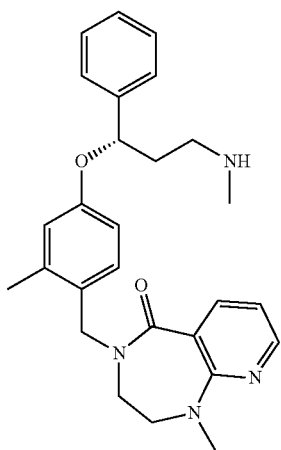 [SMILES: CNCC[C@H](Oc1ccc(CN2CCN(C)c3ncccc3C2=O)c(C)c1)c1ccccc1] | (S)-1-methyl-4-(2-methyl-4-(3-(methylamino)-1-phenylpropoxy)benzyl)-1,2,3,4-tetrahydro-5H-pyrido[2,3-e][1,4]diazepin-5-one | A | 4.73 | 445.2 (M + H) |
| 115 | 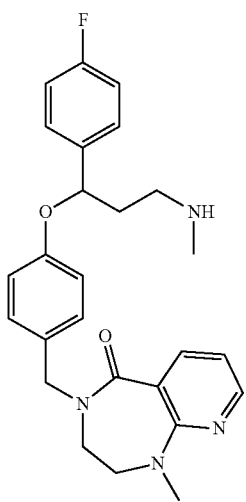 [SMILES: CNCCC(Oc1ccc(CN2CCN(C)c3ncccc3C2=O)cc1)c1ccc(F)cc1] | 4-(4-(1-(4-Fluorophenyl)-3-(methylamino)propoxy)benzyl)-1-methyl-1,2,3,4-tetrahydro-5H-pyrido[2,3-e][1,4]diazepin-5-one | A | 4.70 | 449.3 (M + H) |

| | | | | | |
|---|---|---|---|---|---|
| 116 | 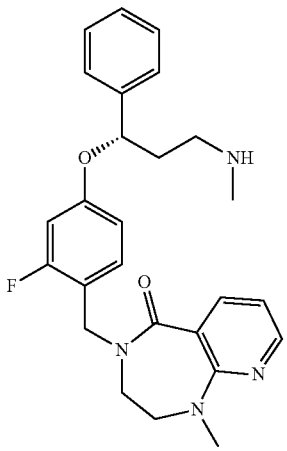 [SMILES: CNCC[C@H](Oc1ccc(CN2CCN(C)c3ncccc3C2=O)c(F)c1)c1ccccc1] | (S)-4-(2-fluoro-4-(3-(methylamino)-1-phenylpropoxy)benzyl)-1-methyl-1,2,3,4-tetrahydro-5H-pyrido[2,3-e][1,4]diazepin-5-one | A | 4.69 | 449.2 (M + H) |
| 117 | 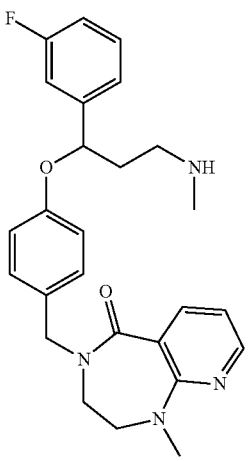 | 4-(4-(1-(3-Fluorophenyl)-3-(methylamino)propoxy)benzyl)-1-methyl-1,2,3,4-tetrahydro-5H-pyrido[2,3-e][1,4]diazepin-5-one | A | 4.69 | 449.2 (M + H) |

In Ex 110-117 Boc was used as protecting group.

Example 118: (R)-4-(ethylamino)-1-(3-((S)-3-(methylamino)-1-(thiophen-2-yl) propoxy)phenyl) azepan-2-one and (S)-4-(ethylamino)-1-(3-((S)-3-(methylamino)-1-(thiophen-2-yl) propoxy)phenyl) azepan-2-one

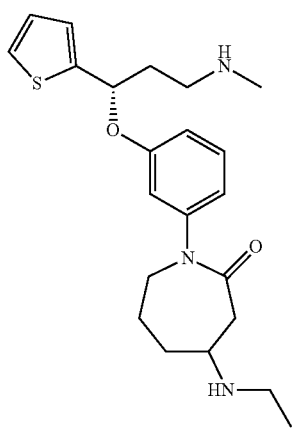 [SMILES: CCNC1CCCN(c2cccc(O[C@@H](CCNC)c3cccs3)c2)C(=O)C1]

a) 2-(Trimethylsilyl)ethyl (S)-(3-(3-(2,4-dioxoazepan-1-yl)phenoxy)-3-(thiophen-2-yl)propyl)(methyl) carbamate Azepane-2,4-dione (140 mg, 1.10 mmol) was treated with 2-(trimethylsilyl)ethyl(S)-(3-(3-bromophenoxy)-3-(thiophen-2-yl)propyl)(methyl) carbamate (518 mg, 1.10 mmol) in the conditions used in Ex 14 step a to afford the tilte compound (90 mg, 16% yield). HPLC (Method B): Ret, 5.80 min; ESI⁺-MS m/z, 539.2 (M+Na).

b) 2-(Trimethylsilyl)ethyl ((3S)-3-(3-(4-(ethylamino)-2-oxoazepan-1-yl)phenoxy)-3-(thiophen-2-yl)propyl)(methyl)carbamate To a suspension of the compound prepared in step a (90 mg, 0.17 mmol) in DCE (3.5 mL), DIPEA (23 mg, 0.17 mmol), Ethylamine (13 mg, 0.21 mmol), NaBH(OAc)$_3$ (74 mg, 0.34 mmol) and acetic acid (11 mg, 0.17 mmol) were added and the mixture was stirred at rt for 65 h. DCM was added and washed with NaHCO$_3$ sat solution and water. The organic layer was dried over Na$_2$SO$_4$, filtered and concentrated under vacuum. Purification by flash chromatography, silica gel, gradient from DCM to 40% MeOH, afforded the title compound as a mixture of two diastereomers (82 mg, 47% yield). HPLC (Method A): Ret, 7.28 min; ESI⁺-MS m/z, 546.3 (M+H).

c) Title Compound

The compound prepared in step b was treated with the conditions used in Ex 11 step b to afford the title compound (90% yield) as a mixture of two diastereomers.

The two diastereomers were separated by semipreparative HPLC. Conditions: column Chiralpak IC 250×4.6 mm; mobile phase, isocratic ACN:MeOH:DEA (90:10:0.4); flux 1 ml/min; conc. 8.4 mg/mL; Ret 6.91 min (Ex 118a) and 7.86 min (Ex 118b).

Example 118a: (R)-4-(ethylamino)-1-(3-((S)-3-(methylamino)-1-(thiophen-2-yl) propoxy)phenyl) azepan-2-one. HPLC (Method A): Ret, 4.32 min; ESI$^+$-MS m/z, 402.2 (M+H)

Example 118b: (S)-4-(ethylamino)-1-(3-((S)-3-(methylamino)-1-(thiophen-2-yl) propoxy)phenyl) azepan-2-one HPLC (Method A): Ret, 4.32 min; ESI$^+$-MS m/z, 402.2 (M+H)

Ex 119-121 were prepared by a sequence of reactions according to the methods described in Ex 14 using suitable starting materials:

| EX | Structure | Chemical name | Method | Ret (min) | MS |
|---|---|---|---|---|---|
| 119 | 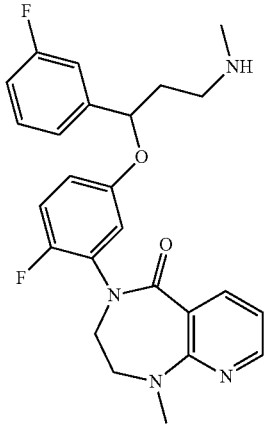 [SMILES: CNCCC(Oc1ccc(F)c(N2CCN(C)c3ncccc3C2=O)c1)c1cccc(F)c1] | 4-(2-Fluoro-5-(1-(3-ftuorophenyl)-3-(methylamino)propoxy)phenyl)-1-methyl-1,2,3,4-tetrahydro-5H-pyrido[2,3-e][1,4]diazepin-5-one | A | 4.79 | 453.2 (M + H) |
| 120 | 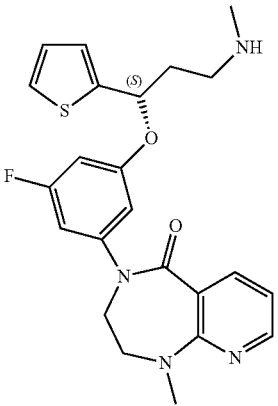 | (S)-4-(3-fluoro-5-(3-(methylamino)-1-(thiophen-2-yl)propoxy)phenyl)-1-methyl-1,2,3,4-tetrahydro-5H-pyrido[2,3-e][1,4]diazepin-5-one | A | 4.64 | 441.2 (M + H) |

-continued

| EX | Structure | Chemical name | Method | Ret (min) | MS |
|---|---|---|---|---|---|
| 121 | 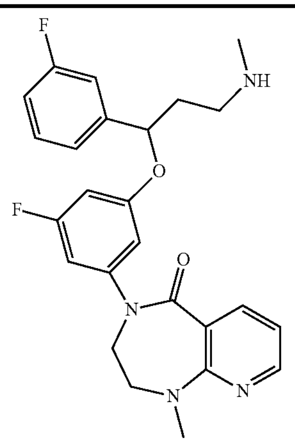 | 4-(3-Fluoro-5-(1-(3-fluorophenyl)-3-(methylamino)propoxy)phenyl)-1-methyl-1,2,3,4-tetrahydro-5H-pyrido[2,3-e][1,4]diazepin-5-one | A | 4.84 | 453.2 (M + H) |

Ex 122-153 were prepared by a sequence of reactions according to the methods described in Ex 90 using suitable starting materials:

| EX | Structure | Chemical name | Method | Ret (min) | MS |
|---|---|---|---|---|---|
| 122 | 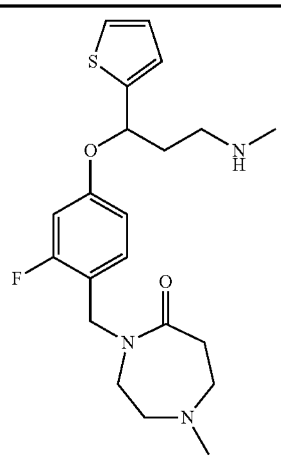 | 4-(2-Fluoro-4-(3-(methylamino)-1-(thiophen-2-yl)propoxy)benzyl)-1-methyl-1,4-diazepan-5-one | A | 4.16 | 406.1 (M + H) |
| 123 | 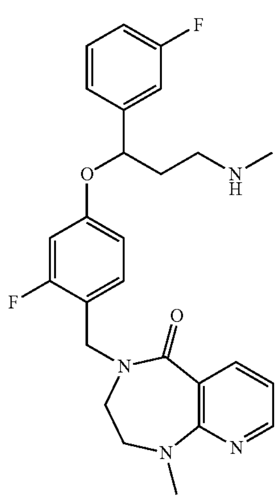 [SMILES: CNCCC(Oc1ccc(CN2CCN(C)c3ncccc3C2=O)c(F)c1)c1cccc(F)c1] | 4-(2-Fluoro-4-(1-(3-fluorophenyl)-3-(methylamino)propoxy)benzyl)-1-methyl-1,2,3,4-tetrahydro-5H-pyrido[2,3-e][1,4]diazepin-5-one | A | 4.81 | 467.5 (M + H) |

-continued

| EX | Structure | Chemical name | Method | Ret (min) | MS |
|---|---|---|---|---|---|
| 124 | 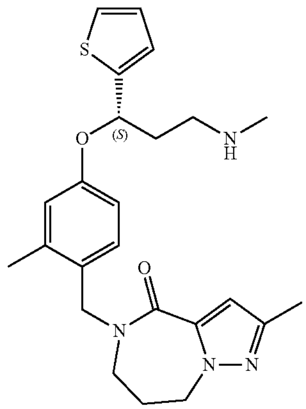 | (S)-2-methyl-5-(2-methyl-4-(3-(methylamino)-1-(thiophen-2-yl)propoxy)benzyl)-5,6,7,8-tetrahydro-4H-pyrazolo[1,5-a][1,4]diazepin-4-one | A | 5.23 | 439.2 (M + H) |
| 125 | 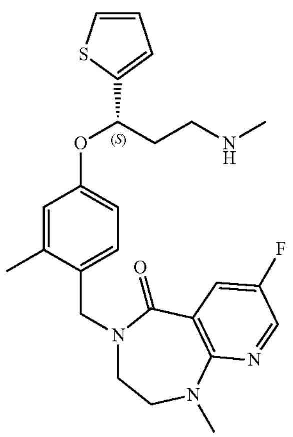 | (S)-7-fluoro-1-methyl-4-(2-methyl-4-(3-(methylamino)-1-(thiophen-2-yl)propoxy)benzyl)-1,2,3,4-tetrahydro-5H-pyrido[2,3-e][1,4]diazepin-5-one | A | 5.65 | 469.2 (M + H) |
| 126 | 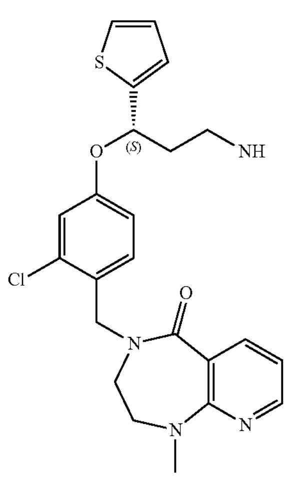 | (S)-4-(2-chloro-4-(3-(methylamino)-1-(thiophen-2-yl)propoxy)benzyl)-1-methyl-1,2,3,4-tetrahydro-5H-pyrido[2,3-e][1,4]diazepin-5-one | A | 4.72 | 471.1 (M + H) |

| EX | Structure | Chemical name | Method | Ret (min) | MS |
|---|---|---|---|---|---|
| 127 | 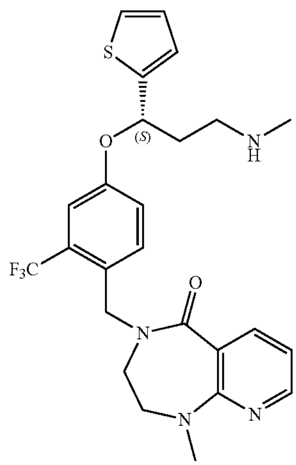 | (S)-1-methyl-4-(4-(3-(methylamino)-1-(thiophen-2-yl)propoxy)-2-(trifluoromethyl)benzyl)-1,2,3,4-tetrahydro-5H-pyrido[2,3-e][1,4]diazepin-5-one | A | 4.99 | 505.2 (M + H) |
| 128 | 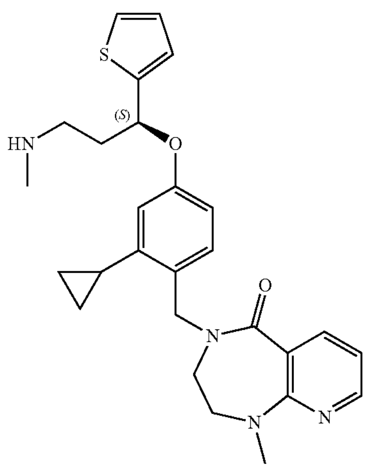 | (S)-4-(2-cyclopropyl-4-(3-(methylamino)-1-(thiophen-2-yl)propoxy)benzyl)-1-methyl-1,2,3,4-tetrahydro-5H-pyrido[2,3-e][1,4]diazepin-5-one | A | 4.73 | 477.2 (M + H) |
| 129 | 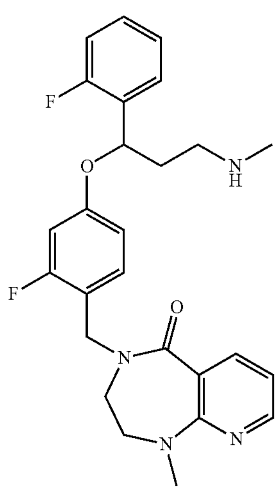 [SMILES: CNCCC(Oc1ccc(CN2CCN(C)c3ncccc3C2=O)c(F)c1)c1ccccc1F] | 4-(2-Fluoro-4-(1-(2-fluorophenyl)-3-(methylamino)propoxy)benzyl)-1-methyl-1,2,3,4-tetrahydro-5H-pyrido[2,3-e][1,4]diazepin-5-one | A | 4.69 | 467.2 (M + H) |

-continued

| EX | Structure | Chemical name | Method | Ret (min) | MS |
|---|---|---|---|---|---|
| 130 | 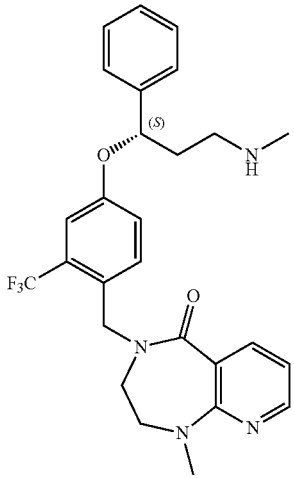 | (S)-1-methyl-4-(4-(3-(methylamino)-1-phenylpropoxy)-2-(trifluoromethyl)benzyl)-1,2,3,4-tetrahydro-5H-pyrido[2,3-e][1,4]diazepin-5-one | A | 5.09 | 499.3 (M + H) |
| 131 | 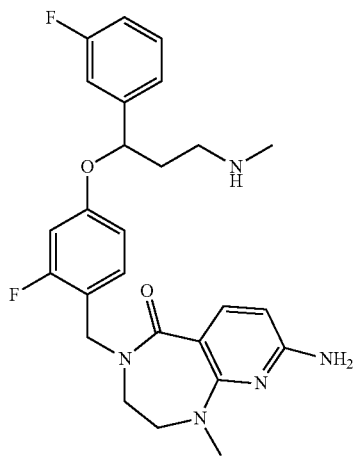 [SMILES: CNCCC(Oc1ccc(CN2CCN(C)c3nc(N)ccc3C2=O)c(F)c1)c1cccc(F)c1] | 8-Amino-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one | A | 4.73 | 482.2 (M + H) |
| 132 | 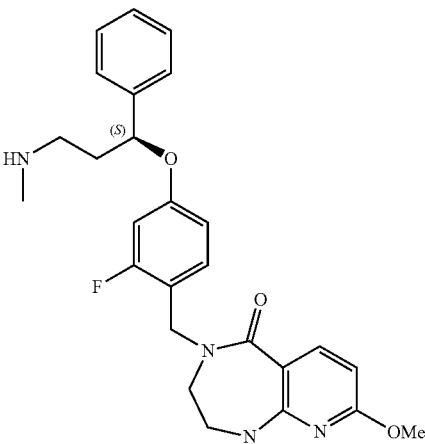 | (S)-4-(2-fluoro-4-(3-(methylamino)-1-phenylpropoxy)benzyl)-8-methoxy-1-methyl-1,2,3,4-tetrahydro-5H-pyrido[2,3-e][1,4]diazepin-5-one | A | 6.21 | 479.3 (M + H) |

-continued

| EX | Structure | Chemical name | Method | Ret (min) | MS |
|---|---|---|---|---|---|
| 133 | 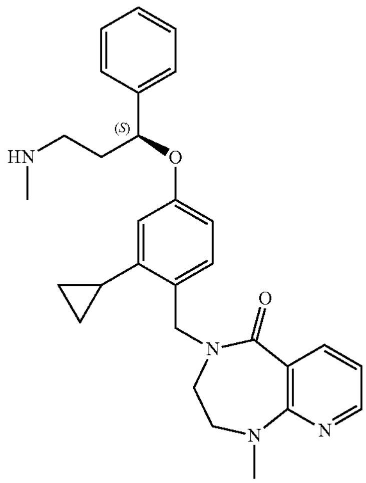 | (S)-4-(2-cyclopropyl-4-(3-(methylamino)-1-phenylpropoxy)benzyl)-1-methyl-1,2,3,4-tetrahydro-5H-pyrido[2,3-e][1,4]diazepin-5-one | A | 4.87 | 471.2 (M + H) |
| 134 | 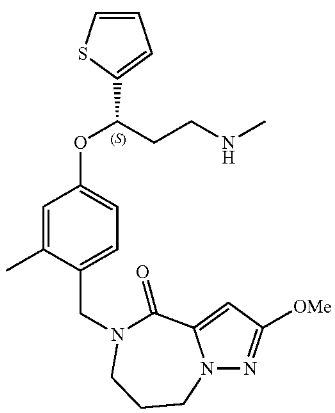 | (S)-2-methoxy-5-(2-methyl-4-(3-(methylamino)-1-(thiophen-2-yl)propoxy)benzyl)-5,6,7,8-tetrahydro-4H-pyrazolo[1,5-a][1,4]diazepin-4-one | A | 5.48 | 455.2 (M + H) |
| 135 | 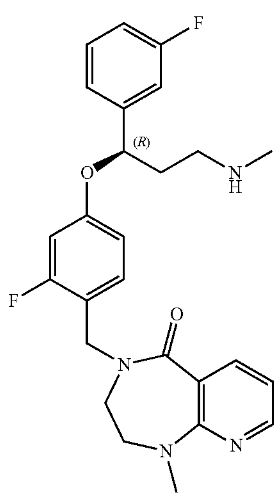 | (R)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one | A | 4.78 | 467.2 (M + H) |

-continued

| EX | Structure | Chemical name | Method | Ret (min) | MS |
|---|---|---|---|---|---|
| 136 | 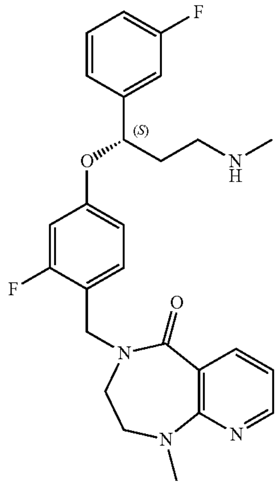 | (S)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one | A | 4.78 | 467.2 (M + H) |
| 137 | 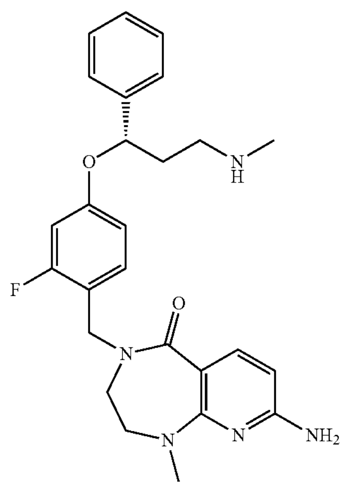 [SMILES: CNCC[C@H](Oc1ccc(CN2CCN(C)c3nc(N)ccc3C2=O)c(F)c1)c1ccccc1] | (S)-8-amino-4-(2-fluoro-4-(3-(methylamino)-1-phenylpropoxy)benzyl)-1-methyl-1,2,3,4-tetrahydro-5H-pyrido[2,3-e][1,4]diazepin-5-one | A | 4.76 | 464.2 (M + H) |
| 138 | 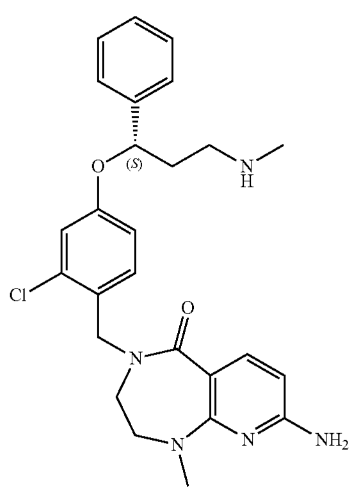 | (S)-8-amino-4-(2-chloro-4-(3-(methylamino)-1-phenylpropoxy)benzyl)-1-methyl-1,2,3,4-tetrahydro-5H-pyrido[2,3-e][1,4]diazepin-5-one | A | 4.84 | 480.3 (M + H) |

-continued

| EX | Structure | Chemical name | Method | Ret (min) | MS |
|---|---|---|---|---|---|
| 139 | 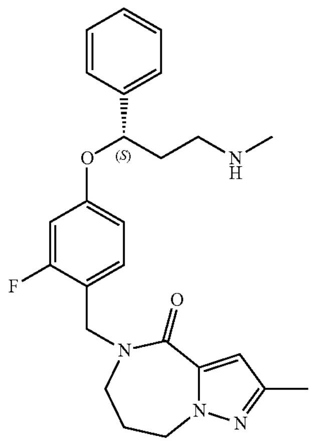 | (S)-5-(2-fluoro-4-(3-(methylamino)-1-phenylpropoxy)benzyl)-2-methyl-5,6,7,8-tetrahydro-4H-pyrazolo[1,5-a][1,4]diazepin-4-one | A | 5.45 | 437.2 (M + H) |
| 140 | 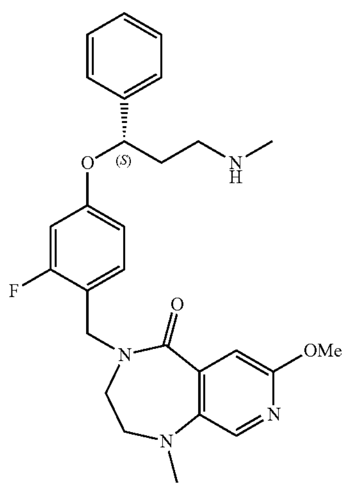 | (S)-4-(2-fluoro-4-(3-(methylamino)-1-phenylpropoxy)benzyl)-7-methoxy-1-methyl-1,2,3,4-tetrahydro-5H-pyrido[3,4-e][1,4]diazepin-5-one | A | 5.79 | 479.3 (M + H) |
| 141 | 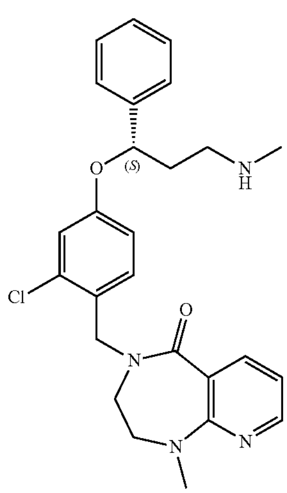 | (S)-(2-chloro-4-(3-(methylamino)-1-phenylpropoxy)benzyl)-1-methyl-1,2,3,4-tetrahydro-5H-pyrido[2,3-e][1,4]diazepin-5-one | A | 4.86 | 465.2 (M + H) |

-continued

| EX | Structure | Chemical name | Method | Ret (min) | MS |
|---|---|---|---|---|---|
| 142 | 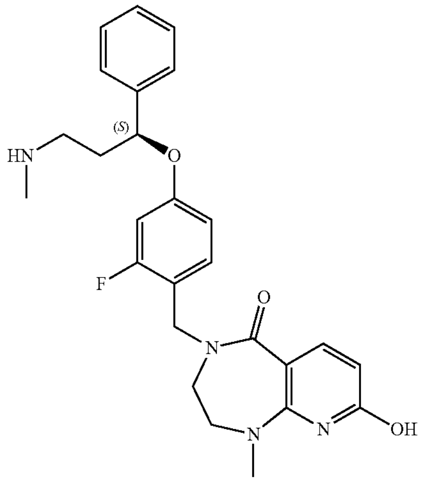 | (S)-4-(2-fluoro-4-(3-(methylamino)-1-phenylpropoxy)benzyl)-8-hydroxy-1-methyl-1,2,3,4-tetrahydro-5H-pyrido[2,3-e][1,4]diazepin-5-one | A | 1.48 | 465.2 (M + H) |
| 143 | 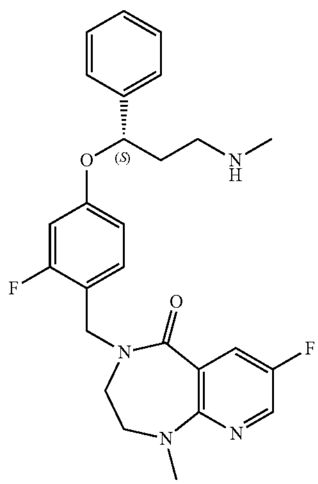 | (S)-7-fluoro-4-(2-fluoro-4-(3-(methylamino)-1-phenylpropoxy)benzyl)-1-methyl-1,2,3,4-tetrahydro-5H-pyrido[2,3-e][1,4]diazepin-5-one | A | 5.86 | 467.3 (M + H) |
| 144 | 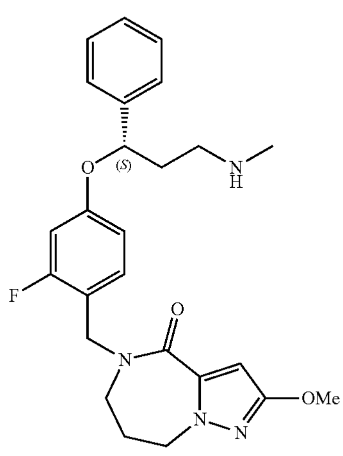 | (S)-5-(2-fluoro-4-(3-(methylamino)-1-phenylpropoxy)benzyl)-2-methoxy-5,6,7,8-tetrahydro-4H-pyrazolo[1,5-a][1,4]diazepin-4-one | A | 5.49 | 453.2 (M + H) |

-continued

| EX | Structure | Chemical name | Method | Ret (min) | MS |
|---|---|---|---|---|---|
| 145 | 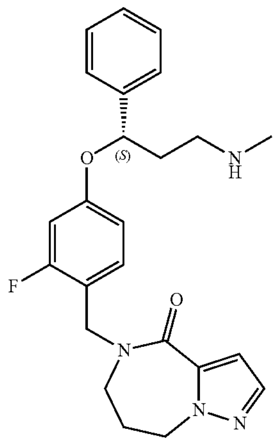 | (S)-5-(2-fluoro-4-(3-(methylamino)-1-phenylpropoxy)benzyl)-5,6,7,8-tetrahydro-4H-pyrazolo[1,5-a][1,4]diazepin-4-one | A | 5.33 | 423.2 (M + H) |
| 146 | 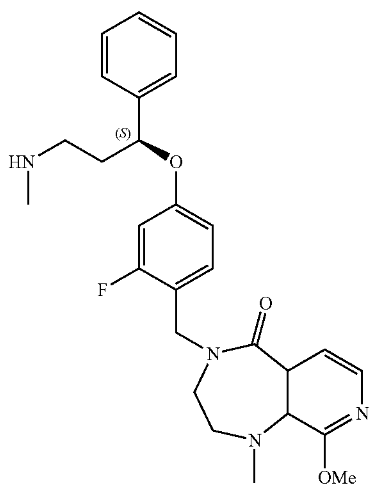 | (S)-4-(2-fluoro-4-(3-(methylamino)-1-phenylpropoxy)benzyl)-9-methoxy-1-methyl-1,2,3,4-tetrahydro-5H-pyrido[3,4-e][1,4]diazepin-5-one | A | 5.16 | 479.3 (M + H) |
| 147 | 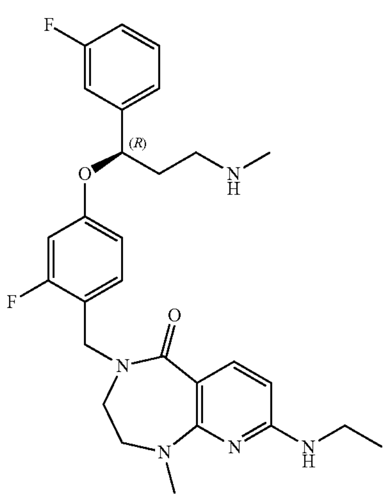 | (R)-8-(ethylamino)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one | A | 5.08 | 510.3 (M + H) |

| EX | Structure | Chemical name | Method | Ret (min) | MS |
|---|---|---|---|---|---|
| 148 | 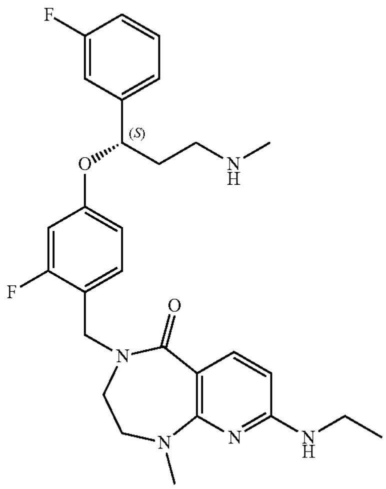 | (S)-8-(ethylamino)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one | A | 5.08 | 510.3 (M + H) |
| 149 | 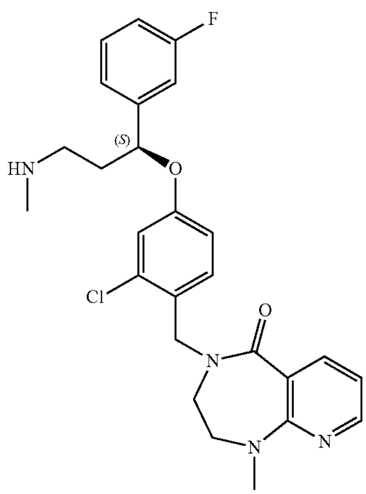 | (S)-4-(2-chloro-4-(1-(3-fluorophenyl)-3-(methylamino)propoxy)benzyl)-1-methyl-1,2,3,4-tetrahydro-5H-pyrido[2,3-e][1,4]diazepin-5-one | A | 4.92 | 483.2 (M + H) |
| 150 | 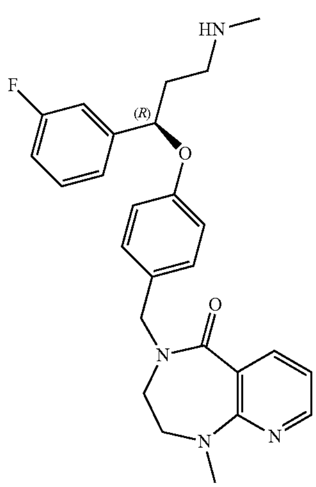 | (R)-(4-(1-(3-fluorophenyl)-3-(methylamino)propoxy)benzyl)-1-methyl-1,2,3,4-tetrahydro-5H-pyrido[2,3-e][1,4]diazepin-5-one | A | 4.71 | 449.3 (M + H) |

-continued

| EX | Structure | Chemical name | Method | Ret (min) | MS |
|---|---|---|---|---|---|
| 151 | 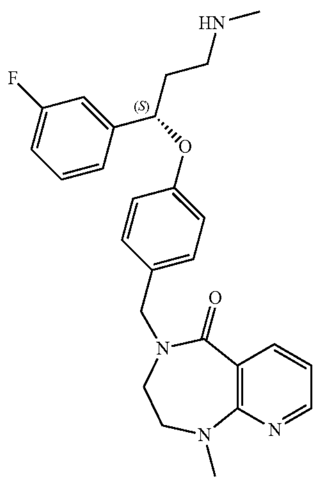 | (S)-4-(4-(1-(3-fluorophenyl)-3-(methylamino)propoxy)benzyl)-1-methyl-1,2,3,4-tetrahydro-5H-pyrido[2,3-e][1,4]diazepin-5-one | A | 4.71 | 449.3 (M + H) |
| 152 | 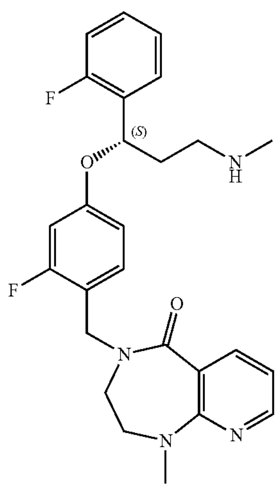 | (S)-4-(2-fluoro-4-(1-(2-fluorophenyl)-3-(methylamino)propoxy)benzyl)-1-methyl-1,2,3,4-tetrahydro-5H-pyrido[2,3-e][1,4]diazepin-5-one | A | 4.70 | 467.2 (M + H) |
| 153 | 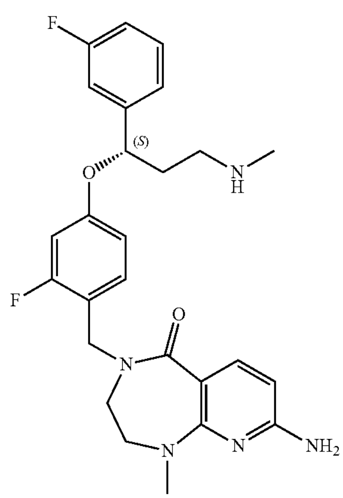 | (S)-8-amino-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one | A | 4.76 | 482.2 (M + H) |

Pharmacological Data.

Binding Assay to Human α2δ-1 Subunit of Ca$_v$2.2 Calcium Channel.

Human α2δ-1 enriched membranes (2.5 μg) were incubated with 15 nM of radiolabeled [3H]-Gabapentin in assay buffer containing Hepes-KOH 10 mM, pH 7.4.

NSB (non specific binding) was measured by adding 10 μM pregabalin. The binding of the test compound was measured in five different concentrations. After 60 min incubation at 27° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4.

Filter plates were dried at 60° C. for 1 hour and 30 μl of scintillation cocktail were added to each well before radioactivity reading.

Readings were performed in a Trilux 1450 Microbeta radioactive counter (Perkin Elmer).

Binding Assay to Human Norepinephrine Transporter (NET).

Human norepinephrine transporter (NET) enriched membranes (5 μg) were incubated with 5 nM of radiolabeled [3H]-Nisoxetin in assay buffer containing 50 mM Tris-HCl, 120 mM NaCl, 5 mM KCl, pH 7.4.

NSB (non specific binding) was measured by adding 10 μM desipramine. The binding of the test compound was measured in five different concentrations. After 60 min incubation at 4° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, 0.9% NaCl, pH 7.4.

Filter plates were dried at 60° C. for 1 hour and 30 μl of scintillation cocktail were added to each well before radioactivity reading.

Readings were performed in a Trilux 1450 Microbeta radioactive counter (Perkin Elmer).

The following scale has been adopted for representing the binding to the α2δ-1 receptor expressed as Ki:

| | |
|---|---|
| + | Ki-α2δ-1 >= 3000 nM |
| ++ | 500 nM < Ki-α2δ-1 < 3000 nM |
| +++ | 100 nM < Ki-α2δ-1 < 500 nM |
| ++++ | Ki-α2δ-1 < 100 nM |

For the dual compounds and regarding the NET receptor, the following scale has been adopted for representing the binding expressed as Ki:

| | |
|---|---|
| + | Ki-NET >= 1000 nM |
| ++ | 500 nM < Ki-NET < 1000 nM |
| +++ | 100 nM < Ki-NET < 500 nM |
| ++++ | Ki-NET < 100 nM |

The results of the binding for α2δ-1 receptor are shown in Table 1:

TABLE 1

| Example number | Ki(nM) alpha2delta Hum |
|---|---|
| 1 | +++ |
| 2 | ++ |
| 3 | ++ |
| 4 | ++ |
| 5 | ++ |
| 6 | ++ |
| 7 | ++ |
| 8 | +++ |
| 9 | + |
| 10 | ++ |
| 11 | ++ |
| 12 | + |
| 13 | ++ |
| 14 | +++ |
| 15 | + |
| 16 | ++ |
| 17 | + |
| 18 | ++ |
| 19 | ++ |
| 20 | + |
| 21 | + |
| 22 | + |
| 23 | + |
| 24 | + |
| 25 | + |
| 26 | ++ |
| 27 | +++ |
| 28 | ++ |
| 29 | ++ |
| 30 | + |
| 31 | ++ |
| 32 | + |
| 33 | + |
| 34 | ++ |
| 35 | ++ |
| 36 | ++ |
| 37 | ++ |
| 38 | ++ |
| 39 | +++ |
| 40 | ++ |
| 41 | + |
| 42 | ++ |
| 43 | +++ |
| 44 | ++ |
| 45 | ++ |
| 46 | + |
| 47 | ++ |
| 48 | ++ |
| 49 | + |
| 50 | ++ |
| 51 | + |
| 52 | + |
| 53 | ++ |
| 54 | ++ |
| 55 | +++ |
| 56 | ++ |
| 57 | ++ |
| 58 | ++ |
| 59 | ++ |
| 60 | ++ |
| 61 | ++ |
| 62 | ++ |
| 63 | +++ |
| 64 | +++ |
| 65 | +++ |
| 66 | ++ |
| 67 | +++ |
| 68 | ++ |
| 69 | ++ |
| 70 | ++ |
| 71 | +++ |
| 72 | +++ |
| 73 | +++ |
| 74 | + |
| 75 | +++ |
| 76 | ++ |
| 77 | +++ |
| 78 | +++ |
| 79 | +++ |
| 80 | +++ |

TABLE 1-continued

| Example number | Ki(nM) alpha2delta Hum |
|---|---|
| 81 | +++ |
| 82 | +++ |
| 83 | +++ |
| 84 | ++ |
| 85 | + |
| 86 | ++ |
| 87 | ++ |
| 88 | + |
| 89 | + |
| 90 | ++++ |
| 91 | +++ |
| 92 | +++ |
| 93 | +++ |
| 94 | +++ |
| 95 | ++ |
| 96 | +++ |
| 97 | ++ |
| 98 | ++ |
| 99 | ++++ |
| 100 | +++ |
| 101 | +++ |
| 102 | + |
| 103 | ++++ |
| 104 | +++ |
| 105 | ++ |
| 106 | ++ |
| 107 | ++++ |
| 108 | ++++ |
| 109 | + |
| 110 | ++ |
| 111 | ++ |
| 112 | + |
| 113 | + |
| 114 | +++ |
| 115 | ++ |
| 116 | ++++ |
| 117 | +++ |
| 118a | ++ |
| 118b | ++ |
| 119 | +++ |
| 120 | ++++ |
| 121 | ++++ |
| 122 | +++ |
| 123 | ++++ |
| 124 | ++++ |
| 125 | ++++ |
| 126 | ++++ |
| 127 | ++++ |
| 128 | +++ |
| 129 | +++ |
| 130 | ++++ |
| 131 | ++++ |
| 132 | +++ |
| 133 | +++ |
| 134 | ++++ |
| 135 | ++ |
| 136 | ++++ |
| 137 | +++ |
| 138 | ++++ |
| 139 | +++ |
| 140 | ++++ |
| 141 | ++++ |
| 142 | + |
| 143 | +++ |
| 144 | +++ |
| 145 | ++ |
| 146 | + |
| 147 | + |
| 148 | +++ |
| 149 | ++++ |
| 150 | ++ |
| 151 | +++ |
| 152 | ++++ |
| 153 | ++++ |

The binding results for the α2δ-1 and the NET receptor for the dual compounds are shown in Table 2;

TABLE 2

| Example number | Ki(nM) NET Hum | Ki(nM) alpha2delta Hum |
|---|---|---|
| 1 | ++ | +++ |
| 3 | +++ | ++ |
| 6 | +++ | ++ |
| 7 | ++ | ++ |
| 10 | ++ | ++ |
| 29 | ++ | ++ |
| 34 | +++ | ++ |
| 37 | +++ | ++ |
| 50 | ++ | ++ |
| 54 | ++++ | ++ |
| 55 | +++ | +++ |
| 56 | ++ | ++ |
| 58 | +++ | ++ |
| 60 | ++ | ++ |
| 61 | +++ | ++ |
| 65 | +++ | +++ |
| 66 | +++ | ++ |
| 67 | ++ | +++ |
| 69 | +++ | ++ |
| 70 | +++ | ++ |
| 71 | +++ | +++ |
| 72 | ++ | +++ |
| 75 | +++ | +++ |
| 76 | ++++ | ++ |
| 77 | +++ | +++ |
| 78 | +++ | +++ |
| 80 | ++++ | +++ |
| 81 | ++ | +++ |
| 82 | +++ | +++ |
| 83 | +++ | +++ |
| 84 | +++ | ++ |
| 86 | +++ | ++ |
| 90 | +++ | ++++ |
| 91 | +++ | +++ |
| 92 | ++++ | +++ |
| 93 | +++ | +++ |
| 94 | +++ | +++ |
| 96 | +++ | +++ |
| 97 | +++ | ++ |
| 98 | +++ | ++ |
| 99 | ++++ | ++++ |
| 100 | ++ | +++ |
| 103 | ++++ | ++++ |
| 104 | +++ | +++ |
| 105 | +-+ | ++ |
| 108 | +++ | ++++ |
| 110 | ++++ | ++ |
| 111 | ++++ | ++ |
| 114 | +++ | +++ |
| 115 | ++++ | ++ |
| 116 | ++++ | ++++ |
| 117 | ++++ | +++ |
| 119 | ++++ | +++ |
| 120 | ++++ | ++++ |
| 121 | ++++ | ++++ |
| 123 | ++++ | ++++ |
| 126 | ++++ | ++++ |
| 129 | ++++ | +++ |
| 131 | ++++ | ++++ |
| 132 | ++++ | +++ |
| 134 | ++++ | ++++ |
| 136 | ++++ | ++++ |
| 137 | ++++ | +++ |
| 138 | ++++ | ++++ |
| 139 | ++++ | +++ |
| 140 | ++++ | ++++ |
| 141 | ++++ | ++++ |
| 142 | ++++ | + |
| 143 | ++++ | +++ |
| 144 | ++++ | +++ |
| 145 | ++++ | ++ |
| 148 | ++++ | +++ |
| 149 | ++++ | ++++ |
| 150 | ++++ | ++ |

TABLE 2-continued

| Example number | Ki(nM) NET Hum | Ki(nM) alpha2delta Hum |
|---|---|---|
| 151 | ++++ | +++ |
| 152 | ++++ | ++++ |
| 153 | ++++ | ++++ |

The invention claimed is:

1. A compound of general formula (I):

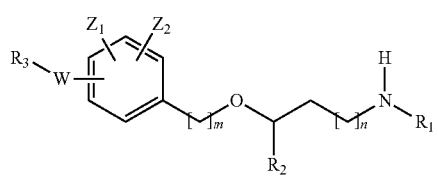

(I)

wherein:

$R_1$ is a branched or unbranched $C_{1-6}$ alkyl radical or a $C_{1-6}$ haloalkyl radical;

$R_2$ is a 6-membered aryl optionally substituted by a halogen atom, a branched or unbranched $C_{1-6}$-alkyl radical, a branched or unbranched $C_{1-6}$-alkoxy radical, a $C_{1-6}$-haloalcoxy radical, a $C_{1-6}$-haloalkyl radical or a hydroxyl radical; or 5 or 6-membered heteroaryl having at least one heteroatom selected from the group consisting of N, O and S;

n and m are independently 0 or 1;

$Z_1$ and $Z_2$ are independently selected from the group consisting of a hydrogen atom; a branched or unbranched $C_{1-6}$-alkyl radical; a halogen atom; a branched or unbranched $C_{1-6}$-alkoxy radical; a $C_{3-6}$ cycloalkyl radical; a $C_{1-6}$-haloalkyl radical; and a $C_{1-6}$-haloalkoxy radical;

—W—$R_3$ is in meta or para position;

W is —$(CH_2)_p$—; —C(O)—; or a bond;

p is 1 or 2;

$R_3$ represents one of the following moieties:

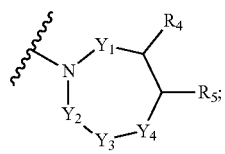

(IA)

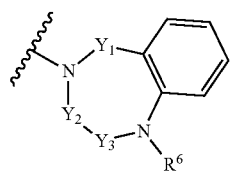

(IB)

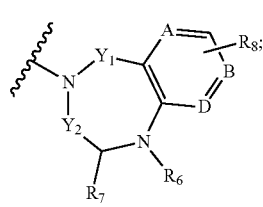

(IC)

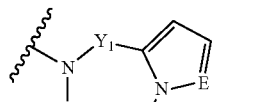

(ID)

or

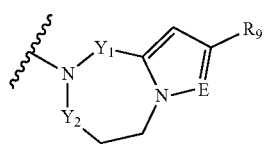

(IE)

wherein $Y_1$ and $Y_2$ are independently —$CH_2$— or —C(O)—;

$Y_3$ is —$CHR_7$— or —C(O)—;

$Y_4$ is —CH— or —N—$R_6$, $R_4$ and $R_5$ are independently a hydrogen atom, a branched or unbranched $C_{1-6}$ alkyl radical or a —$(CH_2)_q$—NRR' radical, wherein q is 0 or 1 and R and R' are independently a hydrogen atom or a branched or unbranched $C_{1-6}$-alkyl radical;

one or two of A, B and D represent —N— and the others are —CH—;

E represents —N— or —CH—;

$R_6$ is a hydrogen atom; a branched or unbranched $C_{1-6}$alkyl radical; or a —C(O)—$CH_2$-$NR_{6a}R_{6b}$ radical, wherein $R_{6a}$ and $R_{6b}$ are independently a hydrogen atom or a branched or unbranched $C_{1-6}$-alkyl radical;

$R_7$ is a hydrogen atom;

or $R_6$ and $R_7$ form a 5 or 6-membered heterocycloalkyl group;

$R_9$ is a hydrogen atom, a branched or unbranched $C_{1-6}$-alkyl radical; a halogen atom; a branched or unbranched $C_{1-6}$-alkoxy radical; a hydroxyl radical; a $C_{1-6}$-haloalkyl radical; or a —$NR_{8a}R_{8b}$ radical, wherein $R_{8a}$ and $R_{8b}$ are independently a hydrogen atom or a branched or unbranched $C_{1-6}$-alkyl radical;

$R_9$ is a branched or unbranched $C_{1-6}$-alkyl radical; or a branched or unbranched $C_{1-6}$-alkoxy radical;

or a pharmaceutically acceptable salt, stereoisomer, enantiomer, diastereomer, prodrug or solvate thereof.

2. The compound according to claim 1, wherein $R_2$ is a phenyl group optionally substituted by a halogen atom, a branched or unbranched $C_{1-6}$-alkyl radical, a branched or unbranched $C_{1-6}$-alkoxy radical, a $C_{1-6}$-haloalkoxy radical, a $C_{1-6}$-haloalkyl radical or a hydroxyl radical; or an optionally substituted thiophene group.

3. The compound according to claim 1, wherein $R_3$ is selected from the group consisting of:

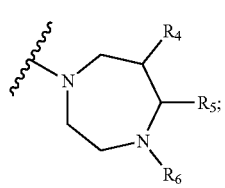

(IA₁)

-continued

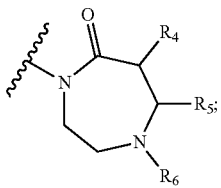
(IA₂)

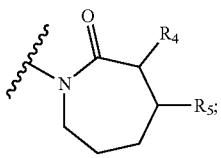
(IA₃)

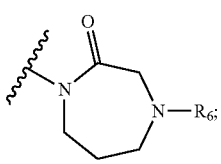
(IA₄)

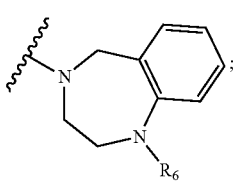
(IB₁)

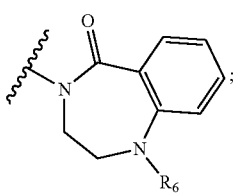
(IB₂)

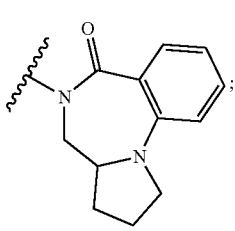
(IB₃)

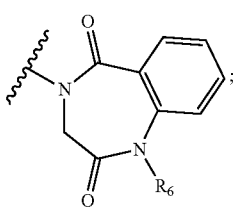
(IB₄)

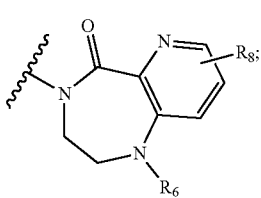
(IC₁)

-continued

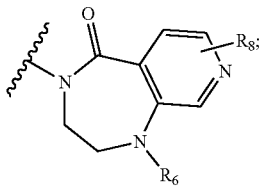
(IC₂)

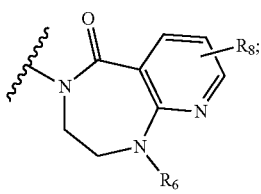
(IC₃)

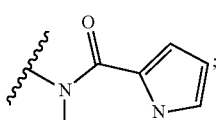
(ID₁)

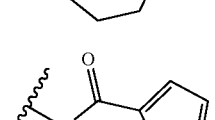
(ID₂)

and

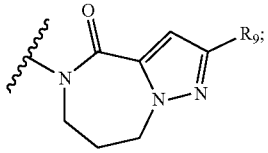
(IE₁)

wherein $R_4$, $R_5$, $R_6$, $R_8$ and $R_9$ are as defined in claim 1.

4. The compound according to claim 1, wherein $Z_1$ and $Z_2$ are independently selected from the group consisting of a hydrogen atom; a branched or unbranched $C_{1-6}$-alkyl radical; a $C_{3-6}$ cycloalkyl radical; and a halogen atom.

5. The compound according to claim 4, wherein $Z_1$ and $Z_2$ are independently selected from the group consisting of hydrogen, methyl, cyclopropyl, and F.

6. The compound according to claim 1, wherein $R_4$ and $R_5$ are independently a hydrogen atom or a —$(CH_2)_q$—NRR' radical, wherein q is 0 or 1 and R and R' are independently a hydrogen atom or a branched or unbranched $C_{1-6}$-alkyl radical.

7. The compound according to claim 6, wherein R and R' are independently hydrogen or ethyl.

8. The compound according to claim 1, wherein $R_6$ is a hydrogen atom; a branched or unbranched $C_{1-6}$ alkyl; or a —C(O)—$CH_2$—$NR_{6a}R_{6b}$ radical, wherein $R_{6a}$ and $R_{6b}$ are independently a hydrogen atom or a branched or unbranched $C_{1-6}$-alkyl radical; and $R_7$ is a hydrogen atom; or $R_6$ and $R_7$ form a pyrrolidine ring.

9. The compound according to claim 8, wherein $R_6$ is hydrogen, methyl, ethyl, isopropyl or a —C(O)—$CH_2$—$NR_{6a}R_{6b}$ radical, wherein $R_{6a}$ and $R_{6b}$ are independently hydrogen or ethyl.

10. The compound according to claim 1, wherein $R_8$ is a hydrogen atom; a branched or unbranched $C_{1-6}$-alkyl radical; a halogen atom; a branched or unbranched $C_{1-6}$-alkoxy radical; a $C_{1-6}$-haloalkyl radical; or a —$NR_{8a}R_{8b}$ radical, wherein $R_{8a}$ and $R_{8b}$ are independently a hydrogen atom or a branched or unbranched $C_{1-6}$-alkyl radical.

11. The compound according to claim 10, wherein $R_8$ is hydrogen, methyl, F, methoxy, trifluoromethyl, or a —$NR_{8a}R_{8b}$ radical, wherein $R_{8a}$ and $R_{8b}$ are independently hydrogen, methyl, or ethyl.

12. The compound according to claim 1, wherein $R_9$ is a methyl or a methoxy.

13. The compound according to claim 1, having one of the following formulas:

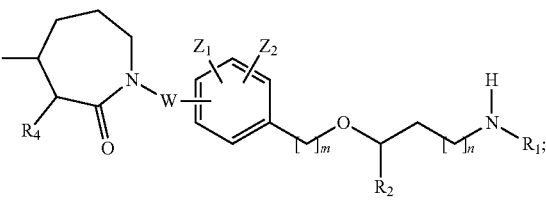

(I$_{1a}$)

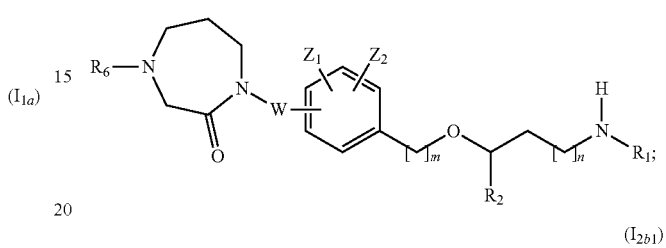

(I$_{1b}$)

(I$_{1c}$)

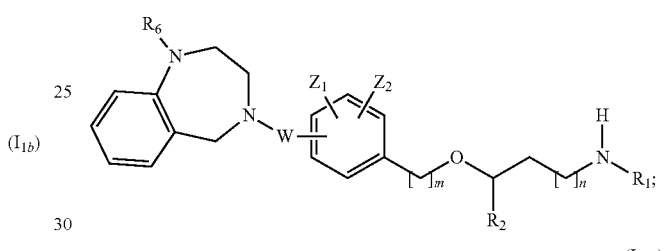

(I$_{2a1}$)

(I$_{2a2}$)

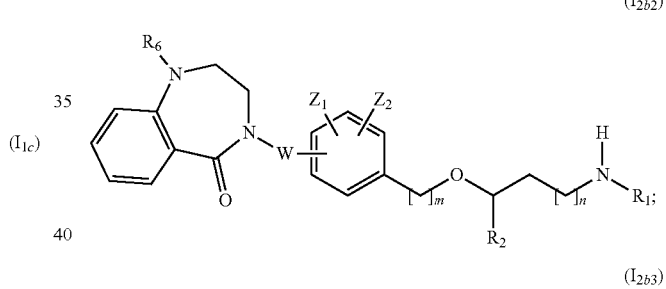

(I$_{2a3}$)

(I$_{2a4}$)

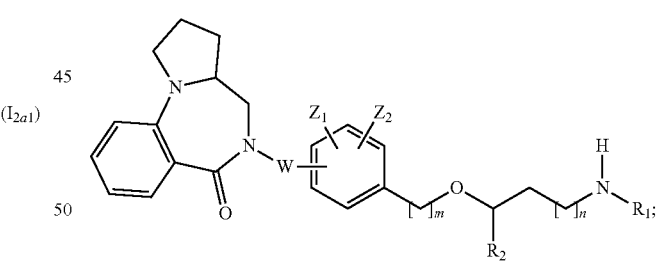

(I$_{2b1}$)

(I$_{2b2}$)

(I$_{2b3}$)

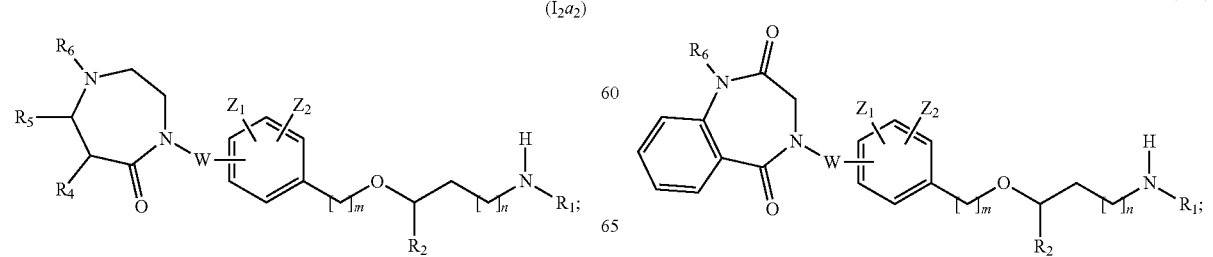

(I$_{2b4}$)

-continued (I$_{2c1}$)
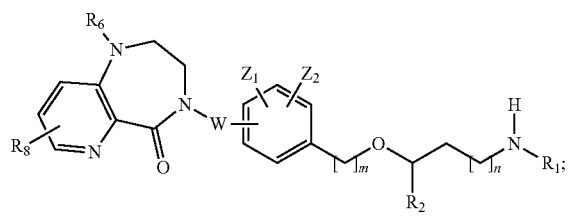

(I$_{2c2}$)
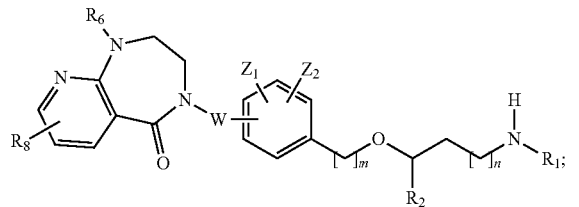

(I$_{2c3}$)
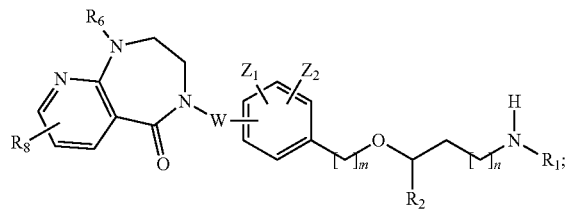

(I$_{2d1}$)
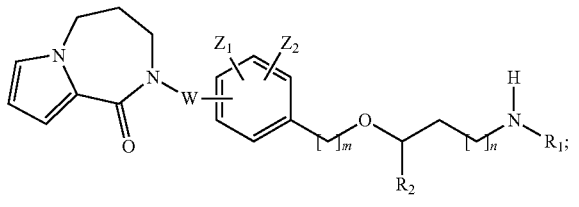

(I$_{2d2}$)
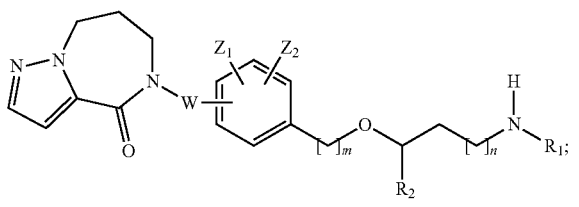

(I$_{2d3}$)
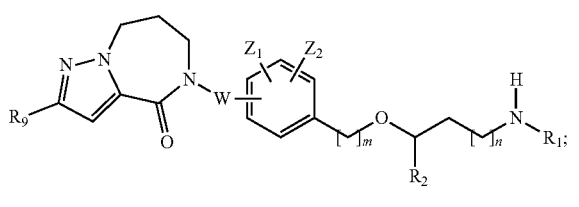

(I$_{3a}$)
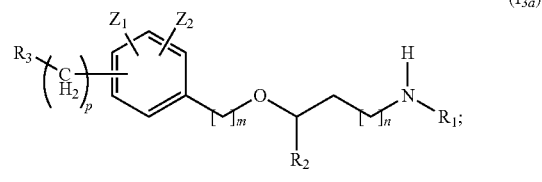

-continued (I$_{3b}$)
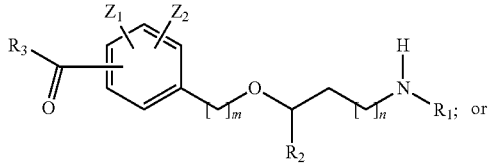

(I$_{3c}$)
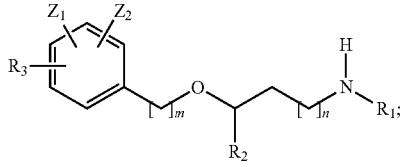

wherein R$_1$, R$_2$, R$_3$, R$_4$, R$_5$, R$_6$, R$_8$, R$_9$, W, Z$_1$, Z$_2$, n and m are as defined in claim 1, and R$_{2a}$ is a hydrogen atom; a halogen atom; a branched or unbranched C$_{1-6}$-alkyl radical; a branched or unbranched C$_{1-6}$-alkoxy radical; a C$_{1-6}$-haloalkoxy radical or a C$_{1-6}$-haloalkyl radical.

14. The compound according to claim 13, wherein R$_{2a}$ is hydrogen or halogen.

15. The compound according to claim 1, which is selected from the group consisting of:
- N-methyl-3-(3-((1-methyl-1,2,3,5-tetrahydro-4H-benzo[e][1,4]diazepin-4-yl)methyl)phenoxy)-3-(thiophen-2-yl)propan-1-amine;
- (4-Methyl-1,4-diazepan-1-yl)(3-(3-(methylamino)-1-(thiophen-2-yl)propoxy)phenyl)methanone;
- (4-Methyl-1,4-diazepan-1-yl)(3-(3-(methylamino)-1-phenylpropoxy)phenyl)methanone;
- (1-Methyl-1,2,3,5-tetrahydro-4H-benzo[e][1,4]diazepin-4-yl)(3-(3-(methylamino)-1-(thiophen-2-yl)propoxy)phenyl)methanone;
- N-methyl-3-(3-(4-methyl-1,4-diazepan-1-yl)phenoxy)-3-phenylpropan-1-amine;
- N-methyl-3-((3-(4-methyl-1,4-diazepan-1-yl)benzyl)oxy)-3-phenylpropan-1-amine;
- N-methyl-3-((3-(1-methyl-1,2,3,5-tetrahydro-4H-benzo[e][1,4]diazepin-4-yl)benzyl)oxy)-3-phenylpropan-1-amine;
- N-methyl-3-(3-(4-methyl-1,4-diazepan-1-yl)phenoxy)-3-(thiophen-2-yl)propan-1-amine;
- N-methyl-3-(3-(1-methyl-1,2,3,5-tetrahydro-4H-benzo[e][1,4]diazepin-4-yl)phenoxy)-3-(thiophen-2-yl)propan-1-amine;
- N-methyl-3-((3-(4-methyl-1,4-diazepan-1-yl)benzyl)oxy)-3-(thiophen-2-yl)propan-1-amine;
- 2-(Ethylamino)-1-(4-(3-(3-(methylamino)-1-(thiophen-2-yl)propoxy)phenyl)-1,4-diazepan-1-yl)ethan-1-one;
- (S)—N-methyl-3-((3-(4-methyl-1,4-diazepan-1-yl)benzyl)oxy)-3-phenylpropan-1-amine;
- (R)—N-methyl-3-((3-(4-methyl-1,4-diazepan-1-yl)benzyl)oxy)-3-phenylpropan-1-amine;
- (R)-1-methyl-4-(3-((3-(methylamino)-1-(thiophen-2-yl)propoxy)methyl)phenyl)-1,2,3,4-tetrahydro-5H-benzo[e][1,4]diazepin-5-one;
- (S)-1-methyl-4-(3-((3-(methylamino)-1-(thiophen-2-yl)propoxy)methyl)phenyl)-1,2,3,4-tetrahydro-5H-benzo[e][1,4]diazepin-5-one;
- 1-(3-((3-(Methylamino)-1-(thiophen-2-yl)propoxy)methyl)phenyl)azepan-2-one;
- 1-(3-(3-(Methylamino)-1-(thiophen-2-yl)propoxy)phenyl)azepan-2-one;

(R)-3-(ethylamino)-1-(3-((S)-3-(methylamino)-1-(thiophen-2-yl)propoxy)phenyl)azepan-2-one;
(S)-3-(ethylamino)-1-(3-((S)-3-(methylamino)-1-(thiophen-2-yl)propoxy)phenyl)azepan-2-one;
(R)-3-((ethylamino)methyl)-1-(3-((S)-3-(methylamino)-1-phenylpropoxy)phenyl)azepan-2-one;
(S)-3-((ethylamino)methyl)-1-(3-((S)-3-(methylamino)-1-phenylpropoxy)phenyl)azepan-2-one;
(R)-7-((ethylamino)methyl)-1-methyl-4-(3-((S)-3-(methylamino)-1-phenylpropoxy)phenyl)-1,4-diazepan-5-one;
(S)-7-((ethylamino)methyl)-1-methyl-4-(3-((S)-3-(methylamino)-1-phenylpropoxy)phenyl)-1,4-diazepan-5-one;
(S)-6-((ethylamino)methyl)-1-methyl-4-(3-((S)-3-(methylamino)-1-phenylpropoxy)phenyl)-1,4-diazepan-5-one;
(R)-6-((ethylamino)methyl)-1-methyl-4-(3-((S)-3-(methylamino)-1-phenylpropoxy)phenyl)-1,4-diazepan-5-one;
1-Methyl-4-(3-((3-(methylamino)-1-phenylpropoxy)methyl)phenyl)-1,2,3,4-tetrahydro-5H-pyrido[3,2-e][1,4]diazepin-5-one;
8-Fluoro-1-methyl-4-(3-((3-(methylamino)-1-phenylpropoxy)methyl)phenyl)-1,2,3,4-tetrahydro-5H-pyrido[3,2-e][1,4]diazepin-5-one;
1-Methyl-4-(3-((3-(methylamino)-1-phenylpropoxy)methyl)phenyl)-1,2,3,4-tetrahydro-5H-pyrido[3,4-e][1,4]diazepin-5-one;
8-(Ethylamino)-1-methyl-4-(3-((3-(methylamino)-1-phenylpropoxy)methyl)phenyl)-1,2,3,4-tetrahydro-5H-pyrido[2,3-e][1,4]diazepin-5-one;
(S)-5-(3-(((S)-3-(methylamino)-1-phenylpropoxy)methyl)phenyl)-1,2,3,3a,4,5-hexahydro-6H-benzo[f]pyrrolo[1,2-a][1,4]diazepin-6-one;
(S)-5-(3-(((R)-3-(methylamino)-1-phenylpropoxy)methyl)phenyl)-1,2,3,3a,4,5-hexahydro-6H-benzo[f]pyrrolo[1,2-a][1,4]diazepin-6-one;
1-Methyl-4-(3-(3-(methylamino)-1-phenylpropoxy)phenyl)-1,4-diazepan-5-one,
1-(3-(3-(Methylamino)-1-phenylpropoxy)phenyl)azepan-2-one;
1-Methyl-4-(3-((3-(methylamino)-1-phenylpropoxy)methyl)phenyl)-1,4-diazepan-5-one;
1-(3-((3-(Methylamino)-1-phenylpropoxy)methyl)phenyl)azepan-2-one;
4-Methyl-1-(3-((3-(methylamino)-1-phenylpropoxy)methyl)phenyl)-1,4-diazepan-2-one;
4-(3-((3-(Methylamino)-1-phenylpropoxy)methyl)phenyl)-1,4-diazepan-5-one;
1-Methyl-4-(3-((3-(methylamino)-1-phenylpropoxy)methyl)phenyl)-1,2,3,4-tetrahydro-5H-benzo[e][1,4]diazepin-5-one;
4-(3-((1-(2-Fluorophenyl)-3-(methylamino)propoxy)methyl)phenyl)-1-methyl-1,2,3,4-tetrahydro-5H-benzo[e][1,4]diazepin-5-one;
4-(3-((1-(3-Fluorophenyl)-3-(methylamino)propoxy)methyl)phenyl)-1-methyl-1,2,3,4-tetrahydro-5H-benzo[e][1,4]diazepin-5-one;
(R)-4-(3-((1-(3-fluorophenyl)-3-(methylamino)propoxy)methyl)phenyl)-1-methyl-1,2,3,4-tetrahydro-5H-benzo[e][1,4]diazepin-5-one;
(S)-4-(3-((1-(3-fluorophenyl)-3-(methylamino)propoxy)methyl)phenyl)-1-methyl-1,2,3,4-tetrahydro-5H-benzo[e][1,4]diazepin-5-one;
4-(3-((3-(Ethylamino)-1-phenylpropoxy)methyl)phenyl)-1-methyl-1,2,3,4-tetrahydro-5H-benzo[e][1,4]diazepin-5-one;
4-(3-((3-((2-Fluoroethyl)amino)-1-phenylpropoxy)methyl)phenyl)-1-methyl-1,2,3,4-tetrahydro-5H-benzo[e][1,4]diazepin-5-one;
1-Methyl-4-(3-((3-(methylamino)-1-phenylpropoxy)methyl)phenyl)-1,2,3,4-tetrahydro-5H-pyrido[2,3-e][1,4]diazepin-5-one;
1-Methyl-4-(4-((3-(methylamino)-1-phenylpropoxy)methyl)phenyl)-1,2,3,4-tetrahydro-5H-benzo[e][1,4]diazepin-5-one;
(R)-1-methyl-4-(3-((3-(methylamino)-1-phenylpropoxy)methyl)phenyl)-1,2,3,4-tetrahydro-5H-benzo[e][1,4]diazepin-5-one;
1,8-Dimethyl-4-(3-((3-(methylamino)-1-phenylpropoxy)methyl)phenyl)-1,2,3,4-tetrahydro-5H-pyrido[2,3-e][1,4]diazepin-5-one;
(S)-1-methyl-4-(3-((3-(methylamino)-1-phenylpropoxy)methyl)phenyl)-1,2,3,4-tetrahydro-5H-benzo[e][1,4]diazepin-5-one;
1-Methyl-4-(3-(3-(methylamino)-1-(thiophen-2-yl)propoxy)phenyl)-1,4-diazepan-5-one;
1-Methyl-4-(3-(3-(methylamino)-1-(thiophen-2-yl)propoxy)phenyl)-3,4-dihydro-1H-benzo[e][1,4]diazepine-2,5-dione;
4-Methyl-1-(3-(3-(methylamino)-1-(thiophen-2-yl)propoxy)phenyl)-1,4-diazepan-2-one;
1-Methyl-4-(3-(3-(methylamino)-1-(thiophen-2-yl)propoxy)phenyl)-1,2,3,4-tetrahydro-5H-benzo[e][1,4]diazepin-5-one;
(S)-8-(ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
(S)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
(R)-8-(ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
1-Methyl-4-(3-(3-(methylamino)-1-(thiophen-2-yl)propoxy)phenyl)-1,2,3,4-tetrahydro-5H-pyrido[3,2-e][1,4]diazepin-5-one;
1-Ethyl-4-(3-(3-(methylamino)-1-(thiophen-2-yl)propoxy)phenyl)-1,4-diazepan-5-one;
4-(3-(3-(Methylamino)-1-(thiophen-2-yl)propoxy)phenyl)-1,4-diazepan-5-one;
1-isopropyl-4-(3-(3-(methylamino)-1-(thiophen-2-yl)propoxy)phenyl)-1,4-diazepan-5-one;
1-isopropyl-4-(3-(3-(methylamino)-1-(thiophen-2-yl)propoxy)phenyl)-1,4-diazepan-5-one;
(S)-1-methyl-4-(3-(3-(methylamino)-1-(thiophen-2-yl)propoxy)phenyl)-1,4-diazepan-5-one;
(R)-1-methyl-4-(3-(3-(methylamino)-1-(thiophen-2-yl)propoxy)phenyl)-1,4-diazepan-5-one;
(R)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
(R)-1,8-dimethyl-4-(3-(3-(methylamino)-1-(thiophen-2-yl)propoxy)phenyl)-1,2,3,4-tetrahydro-5H-pyrido[2,3-e][1,4]diazepin-5-one;
(S)-1,8-dimethyl-4-(3-(3-(methylamino)-1-(thiophen-2-yl)propoxy)phenyl)-1,2,3,4-tetrahydro-5H-pyrido[2,3-e][1,4]diazepin-5-one;
(S)-1-isopropyl-4-(3-(3-(methylamino)-1-(thiophen-2-yl)propoxy)phenyl)-1,4-diazepan-5-one;

(R)-1-isopropyl-4-(3-(3-(methylamino)-1-(thiophen-2-yl)propoxy)phenyl)-1,4-diazepan-5-one;
1-(Ethylglycyl)-4-(3-(3-(methylamino)-1-(thiophen-2-yl)propoxy)phenyl)-1,4-diazepan-5-one;
8-(Ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
8-(Dimethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
1-Methyl-4-(3-(3-(methylamino)-1-(thiophen-2-yl)propoxy)phenyl)-1,2,3,4-tetrahydro-5H-pyrido[2,3-e][1,4]diazepin-5-one;
1,8-Dimethyl-4-(3-(3-(methylamino)-1-(thiophen-2-yl)propoxy)phenyl)-1,2,3,4-tetrahydro-5H-pyrido[2,3-e][1,4]diazepin-5-one;
1-Methyl-4-(3-(3-(methylamino)-1-(thiophen-2-yl)propoxy)phenyl)-1,2,3,4-tetrahydro-5H-pyrido[3,4-e][1,4]diazepin-5-one;
8-Fluoro-1-methyl-4-(3-(3-(methylamino)-1-(thiophen-2-yl)propoxy)phenyl)-1,2,3,4-tetrahydro-5H-pyrido[3,2-e][1,4]diazepin-5-one;
1-isopropyl-4-(3-(3-(methylamino)-1-(thiophen-3-yl)propoxy)phenyl)-1,4-diazepan-5-one;
(R)-1-isopropyl-4-(3-(3-(methylamino)-1-(thiophen-3-yl)propoxy)phenyl)-1,4-diazepan-5-one;
(S)-1-isopropyl-4-(3-(3-(methylamino)-1-(thiophen-3-yl)propoxy)phenyl)-1,4-diazepan-5-one;
1,8-Dimethyl-4-(3-(3-(methylamino)-1-(thiophen-3-yl)propoxy)phenyl)-1,2,3,4-tetrahydro-5H-pyrido[2,3-e][1,4]diazepin-5-one;
(R)-1,8-dimethyl-4-(3-(3-(methylamino)-1-(thiophen-3-yl)propoxy)phenyl)-1,2,3,4-tetrahydro-5H-pyrido[2,3-e][1,4]diazepin-5-one;
(S)-1,8-dimethyl-4-(3-(3-(methylamino)-1-(thiophen-3-yl)propoxy)phenyl)-1,2,3,4-tetrahydro-5H-pyrido[2,3-e][1,4]diazepin-5-one;
(S)-1-methyl-4-(3-(3-(methylamino)-1-(thiophen-2-yl)propoxy)phenyl)-8-(trifluoromethyl)-1,2,3,4-tetrahydro-5H-pyrido[2,3-e][1,4]diazepin-5-one;
(S)-8-methoxy-1-methyl-4-(3-(3-(methylamino)-1-(thiophen-2-yl)propoxy)phenyl)-1,2,3,4-tetrahydro-5H-pyrido[2,3-e][1,4]diazepin-5-one;
(S)-8-amino-1-methyl-4-(3-(3-(methylamino)-1-(thiophen-2-yl)propoxy)phenyl)-1,2,3,4-tetrahydro-5H-pyrido[2,3-e][1,4]diazepin-5-one;
1-Methyl-4-(3-((3-(methylamino)-1-(thiophen-2-yl)propoxy)methyl)phenyl)-1,4-diazepan-5-one;
1-Methyl-4-(4-((2-(methylamino)-1-phenylethoxy)methyl)phenyl)-1,2,3,4-tetrahydro-5H-benzo[e][1,4]diazepin-5-one;
(R)-7-((ethylamino)methyl)-1-methyl-4-(3-((S)-3-(methylamino)-1-(thiophen-2-yl)propoxy)phenyl)-1,4-diazepan-5-one;
(S)-7-((ethylamino)methyl)-1-methyl-4-(3-((S)-3-(methylamino)-1-(thiophen-2-yl)propoxy)phenyl)-1,4-diazepan-5-one;
1-Methyl-4-(4-((3-(methylamino)-1-phenylpropoxy)methyl)benzyl)-1,2,3,4-tetrahydro-5H-benzo[e][1,4]diazepin-5-one;
1-Methyl-4-(3-((3-(methylamino)-1-phenylpropoxy)methyl)benzyl)-1,2,3,4-tetrahydro-5H-benzo[e][1,4]diazepin-5-one;
(S)-1-methyl-4-(4-(3-(methylamino)-1-(thiophen-2-yl)propoxy)benzyl)-1,2,3,4-tetrahydro-5H-pyrido[2,3-e][1,4]diazepin-5-one;
(S)-1,8-dimethyl-4-(4-(3-(methylamino)-1-(thiophen-2-yl)propoxy)benzyl)-1,2,3,4-tetrahydro-5H-pyrido[2,3-e][1,4]diazepin-5-one;
(S)-8-(ethylamino)-1-methyl-4-(4-(3-(methylamino)-1-(thiophen-2-yl)propoxy)benzyl)-1,2,3,4-tetrahydro-5H-pyrido[2,3-e][1,4]diazepin-5-one;
(S)-1-methyl-4-(4-(3-(methylamino)-1-(thiophen-2-yl)propoxy)benzyl)-8-(trifluoromethyl)-1,2,3,4-tetrahydro-5H-pyrido[2,3-e][1,4]diazepin-5-one;
(S)-8-methoxy-1-methyl-4-(4-(3-(methylamino)-1-(thiophen-2-yl)propoxy)benzyl)-1,2,3,4-tetrahydro-5H-pyrido[2,3-e][1,4]diazepin-5-one;
(S)-8-(dimethylamino)-1-methyl-4-(4-(3-(methylamino)-1-(thiophen-2-yl)propoxy)benzyl)-1,2,3,4-tetrahydro-5H-pyrido[2,3-e][1,4]diazepin-5-one;
(S)-1-methyl-4-(4-(3-(methylamino)-1-(thiophen-2-yl)propoxy)benzyl)-1,2,3,4-tetrahydro-5H-pyrido[3,4-e][1,4]diazepin-5-one;
(S)-1-methyl-4-(4-(3-(methylamino)-1-(thiophen-2-yl)propoxy)benzyl)-1,2,3,4-tetrahydro-5H-pyrido[3,2-e][1,4]diazepin-5-one;
(S)-1-methyl-4-(4-(3-(methylamino)-1-(thiophen-2-yl)propoxy)benzyl)-1,2,3,4-tetrahydro-5H-benzo[e][1,4]diazepin-5-one;
1-Methyl-4-(4-(3-(methylamino)-1-(thiophen-2-yl)propoxy)benzyl)-1,2,3,4-tetrahydro-5H-pyrido[2,3-e][1,4]diazepin-5-one;
1,8-Dimethyl-4-(4-(3-(methylamino)-1-(thiophen-2-yl)propoxy)benzyl)-1,2,3,4-tetrahydro-5H-pyrido[2,3-e][1,4]diazepin-5-one;
1-Methyl-4-(4-(3-(methylamino)-1-(thiophen-2-yl)propoxy)benzyl)-1,4-diazepan-5-one;
N-methyl-3-(4-((4-methyl-1,4-diazepan-1-yl)methyl)phenoxy)-3-(thiophen-2-yl)propan-1-amine;
(S)-8-amino-1-methyl-4-(4-(3-(methylamino)-1-(thiophen-2-yl)propoxy)benzyl)-1,2,3,4-tetrahydro-5H-pyrido[2,3-e][1,4]diazepin-5-one;
(S)-5-(4-(3-(methylamino)-1-(thiophen-2-yl)propoxy)benzyl)-5,6,7,8-tetrahydro-4H-pyrazolo[1,5-a][1,4]diazepin-4-one;
(S)-2-(4-(3-(methylamino)-1-(thiophen-2-yl)propoxy)benzyl)-2,3,4,5-tetrahydro-1H-pyrrolo[1,2-a][1,4]diazepin-1-one;
1-Methyl-4-(3-(3-(methylamino)-1-(thiophen-2-yl)propoxy)benzyl)-1,2,3,4-tetrahydro-5H-benzo[e][1,4]diazepin-5-one;
(S)-1-methyl-4-(2-methyl-4-(3-(methylamino)-1-(thiophen-2-yl)propoxy)benzyl)-1,2,3,4-tetrahydro-5H-pyrido[2,3-e][1,4]diazepin-5-one;
(S)-4-(2-fluoro-4-(3-(methylamino)-1-(thiophen-2-yl)propoxy)benzyl)-1-methyl-1,2,3,4-tetrahydro-5H-pyrido[2,3-e][1,4]diazepin-5-one;
1-Methyl-4-(4-((2-(methylamino)-1-phenylethoxy)methyl)benzyl)-1,2,3,4-tetrahydro-5H-benzo[e][1,4]diazepin-5-one;
1,8-Dimethyl-4-(4-(3-(methylamino)-1-phenylpropoxy)benzyl)-1,2,3,4-tetrahydro-5H-pyrido[2,3-e][1,4]diazepin-5-one;
8-(Ethylamino)-1-methyl-4-(4-(3-(methylamino)-1-phenylpropoxy)benzyl)-1,2,3,4-tetrahydro-5H-pyrido[2,3-e][1,4]diazepin-5-one;
1-Methyl-4-(4-(3-(methylamino)-1-phenylpropoxy)benzyl)-1,2,3,4-tetrahydro-5H-benzo[e][1,4]diazepin-5-one;
1-Methyl-4-(3-(3-(methylamino)-1-phenylpropoxy)benzyl)-1,2,3,4-tetrahydro-5H-benzo[e][1,4]diazepin-5-one;

(S)-1-methyl-4-(2-methyl-4-(3-(methylamino)-1-phenyl-propoxy)benzyl)-1,2,3,4-tetrahydro-5H-pyrido[2,3-e][1,4]diazepin-5-one;

4-(4-(1-(4-Fluorophenyl)-3-(methylamino)propoxy)benzyl)-1-methyl-1,2,3,4-tetrahydro-5H-pyrido[2,3-e][1,4]diazepin-5-one;

(S)-4-(2-fluoro-4-(3-(methylamino)-1-phenylpropoxy)benzyl)-1-methyl-1,2,3,4-tetrahydro-5H-pyrido[2,3-e][1,4]diazepin-5-one;

4-(4-(1-(3-Fluorophenyl)-3-(methylamino)propoxy)benzyl)-1-methyl-1,2,3,4-tetrahydro-5H-pyrido[2,3-e][1,4]diazepin-5-one;

(R)-4-(ethylamino)-1-(3-((S)-3-(methylamino)-1-(thiophen-2-yl) propoxy)phenyl)azepan-2-one;

(S)-4-(ethylamino)-1-(3-((S)-3-(methylamino)-1-(thiophen-2-yl) propoxy)phenyl)azepan-2-one;

4-(2-Fluoro-5-(1-(3-fluorophenyl)-3-(methylamino)propoxy)phenyl)-1-methyl-1,2,3,4-tetrahydro-5H-pyrido[2,3-e][1,4]diazepin-5-one;

(S)-4-(3-fluoro-5-(3-(methylamino)-1-(thiophen-2-yl)propoxy)phenyl)-1-methyl-1,2,3,4-tetrahydro-5H-pyrido[2,3-e][1,4]diazepin-5-one;

4-(3-Fluoro-5-(1-(3-fluorophenyl)-3-(methylamino)propoxy)phenyl)-1-methyl-1,2,3,4-tetrahydro-5H-pyrido[2,3-e][1,4]diazepin-5-one;

4-(2-Fluoro-4-(3-(methylamino)-1-(thiophen-2-yl)propoxy)benzyl)-1-methyl-1,4-diazepan-5-one;

4-(2-Fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

(S)-2-methyl-5-(2-methyl-4-(3-(methylamino)-1-(thiophen-2-yl)propoxy)benzyl)-5,6,7,8-tetrahydro-4H-pyrazolo[1,5-a][1,4]diazepin-4-one;

(S)-7-fluoro-1-methyl-4-(2-methyl-4-(3-(methylamino)-1-(thiophen-2-yl)propoxy)benzyl)-1,2,3,4-tetrahydro-5H-pyrido[2,3-e][1,4]diazepin-5-one;

(S)-4-(2-chloro-4-(3-(methylamino)-1-(thiophen-2-yl)propoxy)benzyl)-1-methyl-1,2,3,4-tetrahydro-5H-pyrido[2,3-e][1,4]diazepin-5-one;

(S)-1-methyl-4-(4-(3-(methylamino)-1-(thiophen-2-yl)propoxy)-2-(trifluoromethyl)benzyl)-1,2,3,4-tetrahydro-5H-pyrido[2,3-e][1,4]diazepin-5-one;

(S)-4-(2-cyclopropyl-4-(3-(methylamino)-1-(thiophen-2-yl)propoxy)benzyl)-1-methyl-1,2,3,4-tetrahydro-5H-pyrido[2,3-e][1,4]diazepin-5-one;

4-(2-Fluoro-4-(1-(2-fluorophenyl)-3-(methylamino)propoxy)benzyl)-1-methyl-1,2,3,4-tetrahydro-5H-pyrido[2,3-e][1,4]diazepin-5-one;

(S)-1-methyl-4-(4-(3-(methylamino)-1-phenylpropoxy)-2-(trifluoromethyl)benzyl)-1,2,3,4-tetrahydro-5H-pyrido[2,3-e][1,4]diazepin-5-one;

8-Amino-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

(S)-4-(2-fluoro-4-(3-(methylamino)-1-phenylpropoxy)benzyl)-8-methoxy-1-methyl-1,2,3,4-tetrahydro-5H-pyrido[2,3-e][1,4]diazepin-5-one;

(S)-4-(2-cyclopropyl-4-(3-(methylamino)-1-phenylpropoxy)benzyl)-1-methyl-1,2,3,4-tetrahydro-5H-pyrido[2,3-e][1,4]diazepin-5-one;

(S)-2-methoxy-5-(2-methyl-4-(3-(methylamino)-1-(thiophen-2-yl)propoxy)benzyl)-5,6,7,8-tetrahydro-4H-pyrazolo[1,5-a][1,4]diazepin-4-one;

(R)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

(S)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

(S)-8-amino-4-(2-fluoro-4-(3-(methylamino)-1-phenylpropoxy)benzyl)-1-methyl-1,2,3,4-tetrahydro-5H-pyrido[2,3-e][1,4]diazepin-5-one;

(S)-8-amino-4-(2-fluoro-4-(3-(methylamino)-1-phenylpropoxy)benzyl)-1-methyl-1,2,3,4-tetrahydro-5H-pyrido[2,3-e][1,4]diazepin-5-one;

(S)-5-(2-fluoro-4-(3-(methylamino)-1-phenylpropoxy)benzyl)-2-methyl-5,6,7,8-tetrahydro-4H-pyrazolo[1,5-a][1,4]diazepin-4-one;

(S)-4-(2-fluoro-4-(3-(methylamino)-1-phenylpropoxy)benzyl)-7-methoxy-1-methyl-1,2,3,4-tetrahydro-5H-pyrido[3,4-e][1,4]diazepin-5-one;

(S)-4-(2-chloro-4-(3-(methylamino)-1-phenylpropoxy)benzyl)-1-methyl-1,2,3,4-tetrahydro-5H-pyrido[2,3-e][1,4]diazepin-5-one;

(S)-4-(2-fluoro-4-(3-(methylamino)-1-phenylpropoxy)benzyl)-8-hydroxy-1-methyl-1,2,3,4-tetrahydro-5H-pyrido[2,3-e][1,4]diazepin-5-one;

(S)-7-fluoro-4-(2-fluoro-4-(3-(methylamino)-1-phenylpropoxy)benzyl)-1-methyl-1,2,3,4-tetrahydro-5H-pyrido[2,3-e][1,4]diazepin-5-one;

(S)-5-(2-fluoro-4-(3-(methylamino)-1-phenylpropoxy)benzyl)-2-methoxy-5,6,7,8-tetrahydro-4H-pyrazolo[1,5-a][1,4]diazepin-4-one;

(S)-5-(2-fluoro-4-(3-(methylamino)-1-phenylpropoxy)benzyl)-5,6,7,8-tetrahydro-4H-pyrazolo[1,5-a][1,4]diazepin-4-one;

(S)-4-(2-fluoro-4-(3-(methylamino)-1-phenylpropoxy)benzyl)-9-methoxy-1-methyl-1,2,3,4-tetrahydro-5H-pyrido[3,4-e][1,4]diazepin-5-one;

(R)-8-(ethylamino)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

(S)-8-(ethylamino)-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

(S)-4-(2-chloro-4-(1-(3-fluorophenyl)-3-(methylamino)propoxy)benzyl)-1-methyl-1,2,3,4-tetrahydro-5H-pyrido[2,3-e][1,4]diazepin-5-one;

(R)-4-(4-(1-(3-fluorophenyl)-3-(methylamino)propoxy)benzyl)-1-methyl-1,2,3,4-tetrahydro-5H-pyrido[2,3-e][1,4]diazepin-5-one;

(S)-4-(4-(1-(3-fluorophenyl)-3-(methylamino)propoxy)benzyl)-1-methyl-1,2,3,4-tetrahydro-5H-pyrido[2,3-e][1,4]diazepin-5-one;

(S)-4-(2-fluoro-4-(1-(2-fluorophenyl)-3-(methylamino)propoxy)benzyl)-1-methyl-1,2,3,4-tetrahydro-5H-pyrido[2,3-e][1,4]diazepin-5-one and (S)-8-amino-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

or a pharmaceutically acceptable salt, prodrug or solvate thereof.

16. The compound according to claim 1, having one of the following formulas:

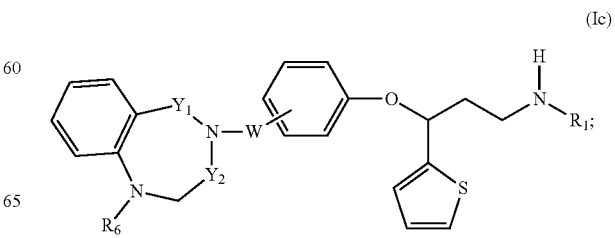

(Ic)

-continued

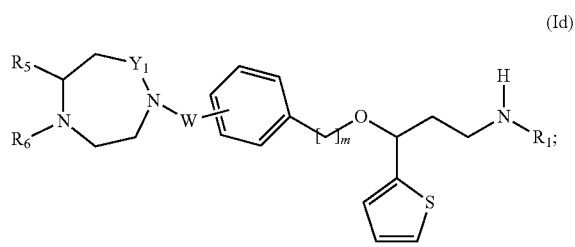
(Id)

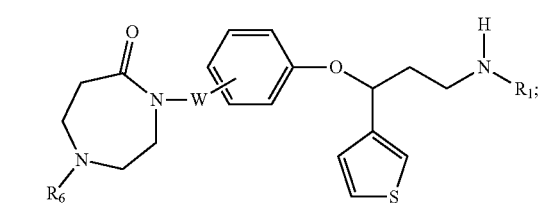
(Ie)

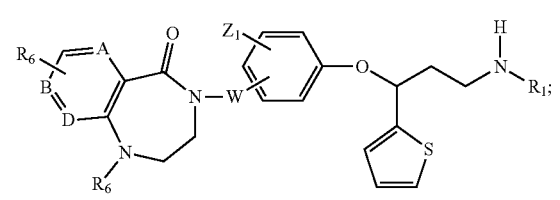
(If)

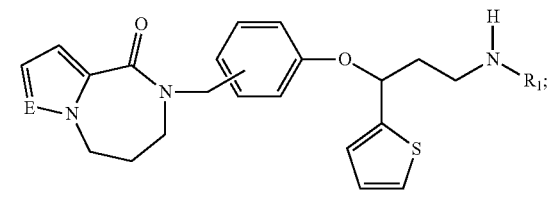
(Ig)

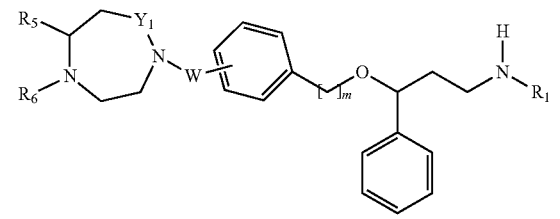
(Ih)

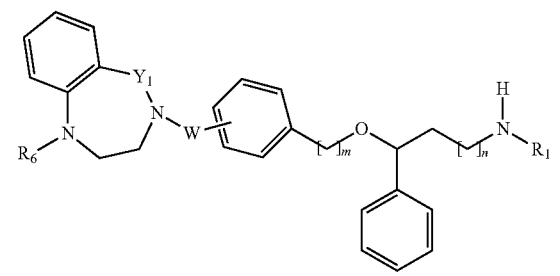
(Ii)

-continued

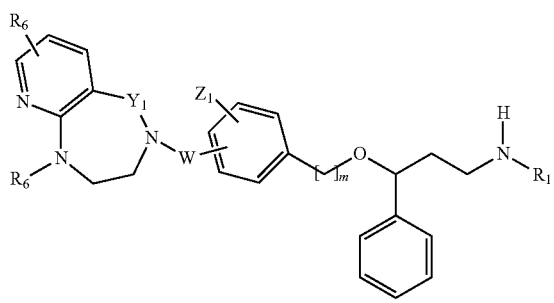
(Ij)

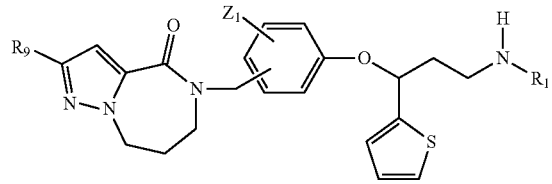
(Ik)

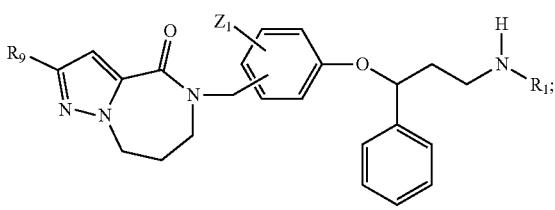
(Im)

wherein R$_1$, R$_5$, R$_6$, R$_8$, R$_9$, Y$_1$, Y$_2$, W, Z1, A, B, D, E n and m are as defined in claim 1.

17. The compound according to claim 1, which is selected from the group consisting of:
N-methyl-3-(3-((1-methyl-1,2,3,5-tetrahydro-4H-benzo[e][1,4]diazepin-4-yl)methyl)phenoxy)-3-(thiophen-2-yl)propan-1-amine;
(4-Methyl-1,4-diazepan-1-yl)(3-(3-(methylamino)-1-phenylpropoxy)phenyl)methanone;
N-methyl-3-((3-(4-methyl-1,4-diazepan-1-yl)benzyl)oxy)-3-phenylpropan-1-amine;
N-methyl-3-((3-(1-methyl-1,2,3,5-tetrahydro-4H-benzo[e][1,4]diazepin-4-yl)benzyl)oxy)-3-phenylpropan-1-amine;
N-methyl-3-((3-(4-methyl-1,4-diazepan-1-yl)benzyl)oxy)-3-(thiophen-2-yl)propan-1-amine;
8-(Ethylamino)-1-methyl-4-(3-((3-(methylamino)-1-phenylpropoxy)methyl)phenyl)-1,2,3,4-tetrahydro-5H-pyrido[2,3-e][1,4]diazepin-5-one;
1-Methyl-4-(3-((3-(methylamino)-1-phenylpropoxy)methyl)phenyl)-1,4-diazepan-5-one;
4-(3-((3-(Methylamino)-1-phenylpropoxy)methyl)phenyl)-1,4-diazepan-5-one;
1-Methyl-4-(3-(3-(methylamino)-1-(thiophen-2-yl)propoxy)phenyl)-1,4-diazepan-5-one;
(S)-8-(ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
(S)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
(R)-8-(ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;

1-Ethyl-4-(3-(3-(methylamino)-1-(thiophen-2-yl)propoxy)phenyl)-1,4-diazepan-5-one;
1-isopropyl-4-(3-(3-(methylamino)-1-(thiophen-2-yl)propoxy)phenyl)-1,4-diazepan-5-one;
(S)-1-methyl-4-(3-(3-(methylamino)-1-(thiophen-2-yl)propoxy)phenyl)-1,4-diazepan-5-one;
(S)-1,8-dimethyl-4-(3-(3-(methylamino)-1-(thiophen-2-yl)propoxy)phenyl)-1,2,3,4-tetrahydro-5H-pyrido[2,3-e][1,4]diazepin-5-one;
(S)-1-isopropyl-4-(3-(3-(methylamino)-1-(thiophen-2-yl)propoxy)phenyl)-1,4-diazepan-5-one;
(R)-1-isopropyl-4-(3-(3-(methylamino)-1-(thiophen-2-yl)propoxy)phenyl)-1,4-diazepan-5-one;
8-(Ethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
8-(Dimethylamino)-1-methyl-4-(3-(3-(methylamino)-1-(thiophen-2-yl)propoxy)phenyl)-1,2,3,4-tetrahydro-5H-pyrido[2,3-e][1,4]diazepin-5-one;
1-Methyl-4-(3-(3-(methylamino)-1-(thiophen-2-yl)propoxy)phenyl)-1,2,3,4-tetrahydro-5H-pyrido[2,3-e][1,4]diazepin-5-one;
1,8-Dimethyl-4-(3-(3-(methylamino)-1-(thiophen-2-yl)propoxy)phenyl)-1,2,3,4-tetrahydro-5H-pyrido[2,3-e][1,4]diazepin-5-one;
1-isopropyl-4-(3-(3-(methylamino)-1-(thiophen-3-yl)propoxy)phenyl)-1,4-diazepan-5-one;
(R)-1-isopropyl-4-(3-(3-(methylamino)-1-(thiophen-3-yl)propoxy)phenyl)-1,4-diazepan-5-one;
(S)-1-isopropyl-4-(3-(3-(methylamino)-1-(thiophen-3-yl)propoxy)phenyl)-1,4-diazepan-5-one;
1,8-Dimethyl-4-(3-(3-(methylamino)-1-(thiophen-3-yl)propoxy)phenyl)-1,2,3,4-tetrahydro-5H-pyrido[2,3-e][1,4]diazepin-5-one;
(S)-1,8-dimethyl-4-(3-(3-(methylamino)-1-(thiophen-3-yl)propoxy)phenyl)-1,2,3,4-tetrahydro-5H-pyrido[2,3-e][1,4]diazepin-5-one;
(S)-1-methyl-4-(3-(3-(methylamino)-1-(thiophen-2-yl)propoxy)phenyl)-8-(trifluoromethyl)-1,2,3,4-tetrahydro-5H-pyrido[2,3-e][1,4]diazepin-5-one;
(S)-8-methoxy-1-methyl-4-(3-(3-(methylamino)-1-(thiophen-2-yl)propoxy)phenyl)-1,2,3,4-tetrahydro-5H-pyrido[2,3-e][1,4]diazepin-5-one;
(S)-8-amino-1-methyl-4-(3-(3-(methylamino)-1-(thiophen-2-yl)propoxy)phenyl)-1,2,3,4-tetrahydro-5H-pyrido[2,3-e][1,4]diazepin-5-one;
1-Methyl-4-(3-((3-(methylamino)-1-(thiophen-2-yl)propoxy)methyl)phenyl)-1,4-diazepan-5-one;
(R)-7-((ethylamino)methyl)-1-methyl-4-(3-((S)-3-(methylamino)-1-(thiophen-2-yl)propoxy)phenyl)-1,4-diazepan-5-one;
(S)-1-methyl-4-(4-(3-(methylamino)-1-(thiophen-2-yl)propoxy)benzyl)-1,2,3,4-tetrahydro-5H-pyrido[2,3-e][1,4]diazepin-5-one;
(S)-1,8-dimethyl-4-(4-(3-(methylamino)-1-(thiophen-2-yl)propoxy)benzyl)-1,2,3,4-tetrahydro-5H-pyrido[2,3-e][1,4]diazepin-5-one;
(S)-8-(ethylamino)-1-methyl-4-(4-(3-(methylamino)-1-(thiophen-2-yl)propoxy)benzyl)-1,2,3,4-tetrahydro-5H-pyrido[2,3-e][1,4]diazepin-5-one;
(S)-1-methyl-4-(4-(3-(methylamino)-1-(thiophen-2-yl)propoxy)benzyl)-8-(trifluoromethyl)-1,2,3,4-tetrahydro-5H-pyrido[2,3-e][1,4]diazepin-5-one;
(S)-8-methoxy-1-methyl-4-(4-(3-(methylamino)-1-(thiophen-2-yl)propoxy)benzyl)-1,2,3,4-tetrahydro-5H-pyrido[2,3-e][1,4]diazepin-5-one;
(S)-1-methyl-4-(4-(3-(methylamino)-1-(thiophen-2-yl)propoxy)benzyl)-1,2,3,4-tetrahydro-5H-pyrido[3,4-e][1,4]diazepin-5-one;
(S)-1-methyl-4-(4-(3-(methylamino)-1-(thiophen-2-yl)propoxy)benzyl)-1,2,3,4-tetrahydro-5H-pyrido[3,2-e][1,4]diazepin-5-one;
(S)-1-methyl-4-(4-(3-(methylamino)-1-(thiophen-2-yl)propoxy)benzyl)-1,2,3,4-tetrahydro-5H-benzo[e][1,4]diazepin-5-one;
1-Methyl-4-(4-(3-(methylamino)-1-(thiophen-2-yl)propoxy)benzyl)-1,2,3,4-tetrahydro-5H-pyrido[2,3-e][1,4]diazepin-5-one;
1,8-Dimethyl-4-(4-(3-(methylamino)-1-(thiophen-2-yl)propoxy)benzyl)-1,2,3,4-tetrahydro-5H-pyrido[2,3-e][1,4]diazepin-5-one;
(S)-8-amino-1-methyl-4-(4-(3-(methylamino)-1-(thiophen-2-yl)propoxy)benzyl)-1,2,3,4-tetrahydro-5H-pyrido[2,3-e][1,4]diazepin-5-one;
(S)-5-(4-(3-(methylamino)-1-(thiophen-2-yl)propoxy)benzyl)-5,6,7,8-tetrahydro-4H-pyrazolo[1,5-a][1,4]diazepin-4-one;
(S)-2-(4-(3-(methylamino)-1-(thiophen-2-yl)propoxy)benzyl)-2,3,4,5-tetrahydro-1H-pyrrolo[1,2-a][1,4]diazepin-1-one;
(S)-4-(2-fluoro-4-(3-(methylamino)-1-(thiophen-2-yl)propoxy)benzyl)-1-methyl-1,2,3,4-tetrahydro-5H-pyrido[2,3-e][1,4]diazepin-5-one;
1,8-Dimethyl-4-(4-(3-(methylamino)-1-phenylpropoxy)benzyl)-1,2,3,4-tetrahydro-5H-pyrido[2,3-e][1,4]diazepin-5-one;
8-(Ethylamino)-1-methyl-4-(4-(3-(methylamino)-1-phenylpropoxy)benzyl)-1,2,3,4-tetrahydro-5H-pyrido[2,3-e][1,4]diazepin-5-one;
(S)-1-methyl-4-(2-methyl-4-(3-(methylamino)-1-phenylpropoxy)benzyl)-1,2,3,4-tetrahydro-5H-pyrido[2,3-e][1,4]diazepin-5-one;
4-(4-(1-(4-Fluorophenyl)-3-(methylamino)propoxy)benzyl)-1-methyl-1,2,3,4-tetrahydro-5H-pyrido[2,3-e][1,4]diazepin-5-one;
(S)-4-(2-fluoro-4-(3-(methylamino)-1-phenylpropoxy)benzyl)-1-methyl-1,2,3,4-tetrahydro-5H-pyrido[2,3-e][1,4]diazepin-5-one;
4-(4-(1-(3-Fluorophenyl)-3-(methylamino)propoxy)benzyl)-1-methyl-1,2,3,4-tetrahydro-5H-pyrido[2,3-e][1,4]diazepin-5-one;
4-(2-Fluoro-5-(1-(3-fluorophenyl)-3-(methylamino)propoxy)phenyl)-1-methyl-1,2,3,4-tetrahydro-5H-pyrido[2,3-e][1,4]diazepin-5-one;
(S)-4-(3-fluoro-5-(3-(methylamino)-1-(thiophen-2-yl)propoxy)phenyl)-1-methyl-1,2,3,4-tetrahydro-5H-pyrido[2,3-e][1,4]diazepin-5-one;
4-(3-Fluoro-5-(1-(3-fluorophenyl)-3-(methylamino)propoxy)phenyl)-1-methyl-1,2,3,4-tetrahydro-5H-pyrido[2,3-e][1,4]diazepin-5-one;
4-(2-Fluoro-4-(1-(3-fluorophenyl)-3-(methylamino)propoxy)phenyl)-1-methyl-1,2,3,4-tetrahydro-5H-pyrido[2,3-e][1,4]diazepin-5-one;
(S)-4-(2-chloro-4-(3-(methylamino)-1-(thiophen-2-yl)propoxy)phenyl)-1-methyl-1,2,3,4-tetrahydro-5H-pyrido[2,3-e][1,4]diazepin-5-one;
4-(2-Fluoro-4-(1-(2-fluorophenyl)-3-(methylamino)propoxy)benzyl)-1-methyl-1,2,3,4-tetrahydro-5H-pyrido[2,3-e][1,4]diazepin-5-one;
8-Amino-4-(2-fluoro-4-(1-(3-fluorophenyl)-3-(methylamino)propoxy)benzyl)-1-methyl-1,2,3,4-tetrahydro-5H-pyrido[2,3-e][1,4]diazepin-5-one;

(S)-4-(2-fluoro-4-(3-(methylamino)-1-phenylpropoxy)
benzyl)-8-methoxy-1-methyl-1,2,3,4-tetrahydro-5H-
pyrido[2,3-e][1,4]diazepin-5-one;
(S)-2-methoxy-5-(2-methyl-4-(3-(methylamino)-1-(thio-
phen-2-yl)propoxy)benzyl)-5,6,7,8-tetrahydro-4H-
pyrazolo[1,5-a][1,4]diazepin-4-one;
(S)-4-(2-fluoro-4-(1-(3-fluorophenyl)-3-(methylamino)
propoxy)benzyl)-1-methyl-1,2,3,4-tetrahydro-5H-
pyrido[2,3-e][1,4]diazepin-5-one;
(S)-8-amino-4-(2-fluoro-4-(3-(methylamino)-1-phenyl-
propoxy)benzyl)-1-methyl-1,2,3,4-tetrahydro-5H-
pyrido[2,3-e][1,4]diazepin-5-one;
(S)-8-amino-4-(2-fluoro-4-(3-(methylamino)-1-phenyl-
propoxy)benzyl)-1-methyl-1,2,3,4-tetrahydro-5H-
pyrido[2,3-e][1,4]diazepin-5-one;
(S)-5-(2-fluoro-4-(3-(methylamino)-1-phenylpropoxy)
benzyl)-2-methyl-5,6,7,8-tetrahydro-4H-pyrazolo[1,5-
a][1,4]diazepin-4-one;
(S)-4-(2-fluoro-4-(3-(methylamino)-1-phenylpropoxy)
benzyl)-7-methoxy-1-methyl-1,2,3,4-tetrahydro-5H-
pyrido[3,4-e][1,4]diazepin-5-one;
(S)-4-(2-chloro-4-(3-(methylamino)-1-phenylpropoxy)
benzyl)-1-methyl-1,2,3,4-tetrahydro-5H-pyrido[2,3-e]
[1,4]diazepin-5-one;
(S)-4-(2-fluoro-4-(3-(methylamino)-1-phenylpropoxy)
benzyl)-8-hydroxy-1-methyl-1,2,3,4-tetrahydro-5H-
pyrido[2,3-e][1,4]diazepin-5-one;
(S)-7-fluoro-4-(2-fluoro-4-(3-(methylamino)-1-phenyl-
propoxy)benzyl)-1-methyl-1,2,3,4-tetrahydro-5H-
pyrido[2,3-e][1,4]diazepin-5-one;
(S)-5-(2-fluoro-4-(3-(methylamino)-1-phenylpropoxy)
benzyl)-2-methoxy-5,6,7,8-tetrahydro-4H-pyrazolo[1,
5-a][1,4]diazepin-4-one;
(S)-5-(2-fluoro-4-(3-(methylamino)-1-phenylpropoxy)
benzyl)-5,6,7,8-tetrahydro-4H-pyrazolo[1,5-a][1,4]di-
azepin-4-one;
(S)-8-(ethylamino)-4-(2-fluoro-4-(1-(3-fluorophenyl)-3-
(methylamino)propoxy)benzyl)-1-methyl-1,2,3,4-tet-
rahydro-5H-pyrido[2,3-e][1,4]diazepin-5-one;
(S)-4-(2-chloro-4-(1-(3-fluorophenyl)-3-(methylamino)
propoxy)benzyl)-1-methyl-1,2,3,4-tetrahydro-5H-
pyrido[2,3-e][1,4]diazepin-5-one;
(R)-4-(4-(1-(3-fluorophenyl)-3-(methylamino)propoxy)
benzyl)-1-methyl-1,2,3,4-tetrahydro-5H-pyrido[2,3-e]
[1,4]diazepin-5-one;
(S)-4-(4-(1-(3-fluorophenyl)-3-(methylamino)propoxy)
benzyl)-1-methyl-1,2,3,4-tetrahydro-5H-pyrido[2,3-e]
[1,4]diazepin-5-one;
(S)-4-(2-fluoro-4-(1-(2-fluorophenyl)-3-(methylamino)
propoxy)benzyl)-1-methyl-1,2,3,4-tetrahydro-5H-
pyrido[2,3-e][1,4]diazepin-5-one and
(S)-8-amino-4-(2-fluoro-4-(1-(3-fluorophenyl)-3-(meth-
ylamino)propoxy)benzyl)-1-methyl-1,2,3,4-tetra-
hydro-5H-pyrido[2,3-e][1,4]diazepin-5-one;
or a pharmaceutically acceptable salt, prodrug or solvate
thereof.

18. A process for the preparation of the compound according to claim 1, wherein the compound is a compound of general formula (Ia):

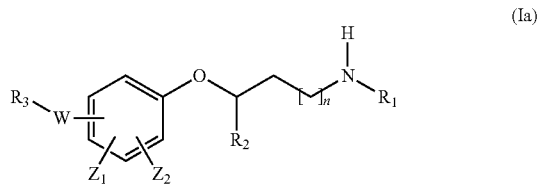
(Ia)

comprising:
a) reaction of a compound of formula (IIa):

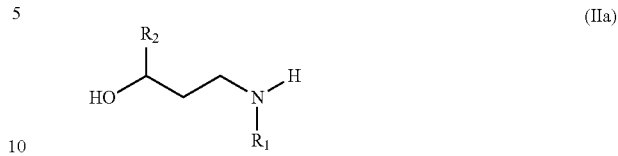
(IIa)

with a compound of formula (IIIa) or (IIIb):

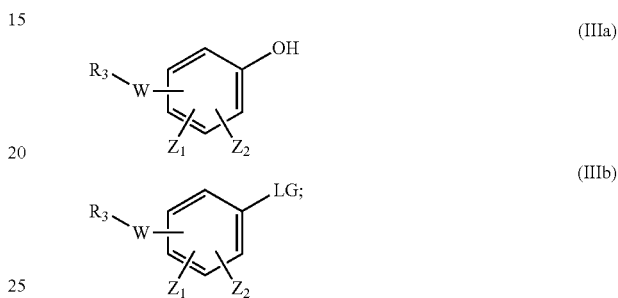
(IIIa)

(IIIb)

or
b) reaction of a compound of formula (IV)-LG:

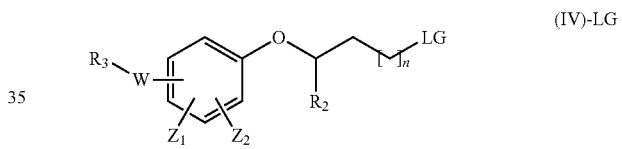
(IV)-LG with a compound of formula (VI):
$H_2NR_1$ (n) wherein $R_1$, $R_2$, $R_3$, W, $Z_1$, $Z_2$ and n are as defined in claim 1, and LG represents a leaving group.

19. A process for the preparation of the compound according to claim 1, wherein the compound is a compound of general formula (Ib):

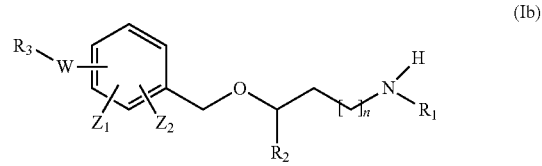
(Ib)

comprising:
a) reaction between a compound of formula (IIa):

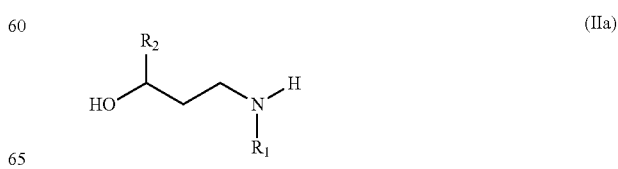
(IIa)

and a compound of formula (IIIc):

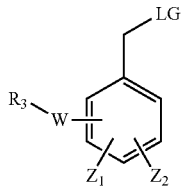

or;

b) deprotection of a compound of formula (V)-P:

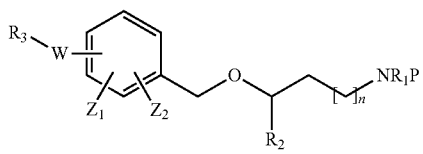

wherein $R_1$, $R_2$, $R_3$, W, $Z_1$, $Z_2$ and n are as defined in claim 1, LG represents a leaving group, and P represents a protecting group.

20. A process for the preparation of a compound of general formula (I) according to claim 1:

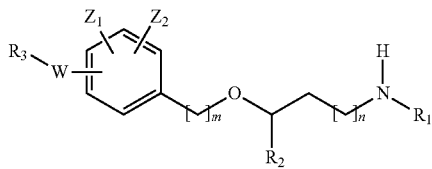

starting from a compound of formula (VII):

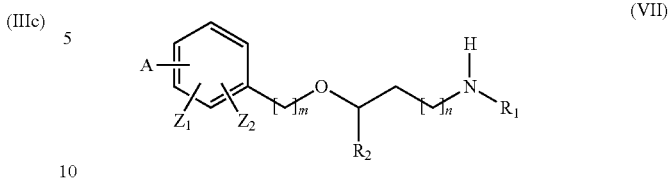

wherein $R_1$, $R_2$, $R_3$, W, $Z_1$, $Z_2$, m and n are as defined in claim 1, and wherein A represents an aldehyde, a carboxylic acid, or a leaving group or —$(CH_2)_p$-LG wherein LG represents a leaving group and p is 1 or 2, and wherein the process is dependent on the nature of A and W resulting in that the process comprises:
- a reductive amination reaction in the presence of a reductive agent, when A is an aldehyde and W is —$(CH_2)_p$—;
- reaction in the presence of a carboxylic acid activating reagent, when A is a carboxylic acid and W is a —C(O)— group;
- a coupling reaction in the presence of a metal catalyst, when A is a leaving group and W is a bond; or
- a reaction in the presence of a base, when A is —$(CH_2)_p$-LG group and W is a —$(CH_2)_p$— group.

21. A method for the treatment of pain in a subject in need thereof, comprising administration of an effective amount of the compound according to claim 1.

22. The method according to claim 21, wherein the disease or disorder pain is selected from the group consisting of medium to severe pain, visceral pain, chronic pain, and acute pain.

23. A pharmaceutical composition comprising the compound according to claim 1, or a pharmaceutically acceptable salt, stereoisomer, enantiomer, diastereomer, prodrug or solvate thereof, and at least a pharmaceutically acceptable carrier, additive, adjuvant or vehicle.

24. The compound according to claim 14, wherein $R_{2a}$ is F.

25. The method according to claim 21, wherein the pain is selected from the group consisting of visceral pain, cancer pain, migraine, inflammatory pain, and neuropathic pain.

* * * * *

UNITED STATES PATENT AND TRADEMARK OFFICE
CERTIFICATE OF CORRECTION

PATENT NO. : 11,401,270 B2
APPLICATION NO. : 16/755992
DATED : August 2, 2022
INVENTOR(S) : Carmen Almansa-Rosales and Félix Cuevas-Cordobés It is certified that error appears in the above-identified patent and that said Letters Patent is hereby corrected as shown below:

In the Claims

Claim 1, Column 170, Line 38:
"$R_9$" should read -- $R_8$ --.

Claim 13, Column 173, formula ($I_{1a}$), Line 20:
The second "m" should read -- n --.

Claim 18, Column 188, Line 41:
Delete "(n)".

Claim 22, Column 190, Line 32:
Delete "visceral pain".

Signed and Sealed this
Sixth Day of September, 2022

Katherine Kelly Vidal
*Director of the United States Patent and Trademark Office*